United States Patent
Sellar et al.

(10) Patent No.: US 11,426,405 B2
(45) Date of Patent: Aug. 30, 2022

(54) INHIBITION OF JAK-STAT SIGNALING INHIBITS FORMATION OF NEUTROPHIL EXTRACELLULAR TRAPS (NETS)

(71) Applicants: The Brigham and Women's Hospital, Inc., Boston, MA (US); Children's Medical Center Corporation, Boston, MA (US)

(72) Inventors: Rob Sellar, Newton, MA (US); Benjamin Ebert, Brookline, MA (US); Ofir Wolach, Boston, MA (US); Kimberly Martinod, Boston, MA (US); Denisa Wagner, Dover, MA (US)

(73) Assignees: The Brigham and Women's Hospital, Inc., Boston, MA (US); Children's Medical Center Corporation, Boston, MA (US)

( * ) Notice: Subject to any disclaimer, the term of this patent is extended or adjusted under 35 U.S.C. 154(b) by 492 days.

(21) Appl. No.: 16/209,698

(22) Filed: Dec. 4, 2018

(65) Prior Publication Data
US 2019/0167680 A1    Jun. 6, 2019

Related U.S. Application Data

(60) Provisional application No. 62/594,266, filed on Dec. 4, 2017.

(51) Int. Cl.
| | |
|---|---|
| *C12Q 1/68* | (2018.01) |
| *A61K 31/506* | (2006.01) |
| *A61P 9/10* | (2006.01) |
| *C12Q 1/6869* | (2018.01) |
| *C12Q 1/6876* | (2018.01) |
| *C12Q 1/48* | (2006.01) |
| *C12Q 1/6883* | (2018.01) |

(52) U.S. Cl.
CPC .............. *A61K 31/506* (2013.01); *A61P 9/10* (2018.01); *C12Q 1/485* (2013.01); *C12Q 1/6869* (2013.01); *C12Q 1/6876* (2013.01); *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

PUBLICATIONS

Tevet et al.; MAEDICA—A Journal of Clinical Medicine, vol. 10, 2015, pp. 27-32.*
Mesa et al; Nature Reviews, vol. 11, Feb. 2012, pp. 103-104.*
Musumeci et al; Current Medicinal Chemistry, vol. 26, 1806-1832, 2019.*

Barbui et al., "Myeloproliferative neoplasms and thrombosis," Blood, 2013, 122(13):2176-2184.
Barbui et al., "Thrombosis in primary myelofibrosis: incidence and risk factors," Blood, 2010, 115:778-782.
Barbui et al., "White blood cell counts and thrombosis in polycythemia vera: a subanalysis of the CYTO-PV study," Blood, 2015, 126(4):560-561.
Bamado et al., "At the Bedside: Neutrophil extracellular traps (NETs) as targets for biomarkers and therapies in autoimmune diseases," J. Leukoc. Biol., 2016, 99:265-278.
Brill et al., "Neutrophil extracellular traps promote deep vein thrombosis in mice," J. Thromb. Haemost., 2012, 10(1):136-144.
Brinkmann et al., "Neutrophil extracellular traps kill bacteria," Science, 303(5663):1532-1535.
Buxhofer-Ausch et al., "Leukocytosis as an important risk factor for arterial thrombosis in WHO-defined early/prefibrotic myelofibrosis: an international study of 264 patients," Am. J. Hematol., 2012, 87(7):669-672.
Campbell et al., "Correlation of blood counts with vascular complications in essential thrombocythemia: analysis of the prospective PT1 cohort," Blood, 2012, 120(7):1409-1411.
Carobbio et al., "Leukocytosis and risk stratification assessment in essential thrombocythemia," J. Clin. Oncol., Jun. 2008, 26(16):2732-2736.
Cedarvall and Olsson, "NETosis in cancer," Oncoscience, 2015. 2(11):900-901.
Demers et al., "Cancers predispose neutrophils to release extracellular DNA traps that contribute to cancer-associated thrombosis," Proc. Natl. Acad. Sci. USA, Aug. 2012, 109(32):13076-13081.
Double and Harrison, "Essential thrombocythaemia," Hematology, Mar. 2015, 20(2):119-120.
El-Sayed et al., "Intact Toll-like receptor 9 signaling in neutrophils modulates normal thrombogenesis in mice," J. Vasc. Surg., Nov. 2016, 64:1450-1458 e1451.
Falanga & Marchetti, "Thrombosis in myeloproliferative neoplasms," Semin Thromb Hemost, Mar. 2014, 40(3):348-358.
Fuchs et al., "Extracellular DNA traps promote thrombosis," Proc Natl Acad Sci USA, Sep. 2010, 107(36):15880-15885.
Genovese et al., "Clonal hematopoiesis and blood-cancer risk inferred from blood DNA sequence," N. Engl. J. Med., Dec. 2014, 371(26):2477-2487.
Gonzalez et al., "Induction and quantification of neutrophil extracellular traps," Methods Mol Biol., Jan. 2014, 1124:307-318.
He et al., "Neutrophil Extracellular Traps in Autoimmune Diseases," Chin Med J (Engl), Jul. 2018, 131(13):1513-1519.
Heuser et al., "Clonal Hematopoiesis of Indeterminate Potential," Dtsch. Arztebl. Int., May 2016, 113(18):317-322.
Hurtado-Nedelec et al., "Increased reactive oxygen species production and p47phox phosphorylation in neutrophils from myeloproliferative disorders patients with JAK2 (V617F) mutation," Haematologica, Oct. 2013, 98(10):1517-1524.

(Continued)

*Primary Examiner* — Jehanne S Sitton
(74) *Attorney, Agent, or Firm* — Fish & Richardson P.C.

(57) ABSTRACT

The methods described herein include methods for the treatment of subjects who have Clonal Hematopoiesis of Indeterminate Potential (CHIP) or a Philadelphia-negative myeloproliferative neoplasm (MPN), e.g., polycythaemia vera (PV) or essential thrombocythaemia (ET), using inhibitors of JAK-STAT signaling.

10 Claims, 36 Drawing Sheets
(29 of 36 Drawing Sheet(s) Filed in Color)
Specification includes a Sequence Listing.

(56) References Cited

PUBLICATIONS

Jaiswal et al., "Age-related clonal hematopoiesis associated with adverse outcomes," N. Engl. J. Med., Dec. 2014, 371(26):2488-2498.

Keohane et al., "The effects of JAK inhibitor therapy upon novel markers of thrombosis in myeloproliferative neoplasms," Haematologica, Sep. 2015, 100(9):e348-e350.

Klampfl et al., "Somatic mutations of calreticulin in myeloproliferative neoplasms," N. Engl. J. Med., Dec. 2013, 369:2379-2390.

Kushnir et al., "Persistent neutrophilia is a marker for an increased risk of venous thrombosis," J. Thromb. Thrombolysis, 42(4):545-551.

Lamrani et al., "Hemostatic disorders in a JAK2V617F-driven mouse model of myeloproliferative neoplasm," Blood 124, 1136-1145 (2014).

Landolfi et al., "Leukocytosis as a major thrombotic risk factor in patients with polycythemia vera," Blood, 2007, 109(6):2446-2452.

Lee et al., "Neutrophil extracellular traps (NETs) in autoimmune diseases: a comprehensive review," Autoimmun Rev., Nov. 2017, 16(11):1160-1173.

Leshner et al., "PAD4 mediated histone hypercitrullination induces heterochromatin decondensation and chromatin unfolding to form neutrophil extracellular trap-like structures," Front. Immunol., Oct. 2012, 3:307, 12 pages.

Lewis et al., "Inhibition of PAD4 activity is sufficient to disrupt mouse and human NET formation," Nat. Chem. Biol., Mar. 2015, 11(3):189-191.

Li et al., "PAD4 is essential for antibacterial innate immunity mediated by neutrophil extracellular traps," J. Exp. Med., Aug. 2010, 207, 1853-1862.

Martinod & Wagner, "Thrombosis: tangled up in NETs," Blood, 2014, 123(18):2768-2776.

Martinod et al., "Neutrophil elastase-deficient mice form neutrophil extracellular traps in an experimental model of deep vein thrombosis," J Thromb Haemost, Feb. 2016, 14(3):551-558.

Martinod et al., "Neutrophil histone modification by peptidylarginine deiminase 4 is critical for deep vein thrombosis in mice," Proc Natl Acad Sci USA, May 2013, 110(21):8674-8679.

McMullin et al., "A guideline for the diagnosis and management of polycythaemia vera. A British Society for Haematology Guideline," Br. J. Haematol., Nov. 2018, 16 pages.

Meng et al., "In Vivo Role of Neutrophil Extracellular Traps in Antiphospholipid Antibody-Mediated Venous Thrombosis," Arthritis Rheumatol, Mar. 2017, 69(3):655-667.

Mullally et al., "Physiological Jak2V617F expression causes a lethal myeloproliferative neoplasm with differential effects on hematopoietic stem and progenitor cells," Cancer Cell, Jun. 2010, 17(6):584-596.

Olsson and Cedarvall, "NETosis in Cancer—Platelet-Neutrophil Crosstalk Promotes Tumor-Associated Pathology," Front Immunol. 2016, 7:373, 8 pages.

Oyarzun et al., "Neutrophil extracellular trap formation and circulating nucleosomes in patients with chronic myeloproliferative neoplasms," Sci. Rep., 2016, 6:38738, 13 pages.

Quintas-Cardama et al., "Preclinical characterization of the selective JAK1/2 inhibitor INCB018424: therapeutic implications for the treatment of myeloproliferative neoplasms," Blood, Apr. 2010, 115(15):3109-3117.

Rampal et al., "Integrated genomic analysis illustrates the central role of JAK-STAT pathway activation in myeloproliferative neoplasm pathogenesis," Blood 123, e123-133 (2014).

Simon et al., "Extracellular DNA traps in allergic, infectious, and autoimmune diseases," Allergy, Feb. 2013, 68(4):409-416.

Steensma et al., "Clonal hematopoiesis of indeterminate potential and its distinction from myelodysplastic syndromes," Blood, Jul. 2015, 2:126(1):9-16.

Tefler and Barbui, "Polycythemia vera and essential thrombocythemia: 2015 update on diagnosis, risk-stratification and management," Am. J. Hematol., Feb. 2015, 90(2):162-173.

Vadher et al., "Life-threatening thrombotic and haemorrhagic problems associated with silent myeloproliferative disorders," Br. J. Haematol., 1993, 85:213-216 (1993).

Vannucchi & Guglielmelli, "JAK2 mutation-related disease and thrombosis," Semin Thromb Hemost, Apr. 2013, 39(5):496-506.

Vannucchi et al., "Ruxolitinib versus standard therapy for the treatment of polycythemia vera," N. Engl. J. Med., Jan. 2015, 372, 426-435.

Verstovsek et al., "A double-blind, placebo-controlled trial of ruxolitinib for myelofibrosis," N. Engl. J. Med., Mar. 2012, 366(9):799-807.

Wang et al., "Histone hypercitrullination mediates chromatin decondensation and neutrophil extracellular trap formation," J. Cell Biol., Jan. 2009, 184(2):205-213.

Wernig et al., "Expression of Jak2V617F causes a polycythemia vera-like disease with associated myelofibrosis in a murine bone marrow transplant model," Blood, Jun. 2006, 107(11):4274-4281.

Wong et al., "Diabetes primes neutrophils to undergo NETosis, which impairs wound healing," Nat Med, Jul. 2015, 21(7):815-819.

* cited by examiner

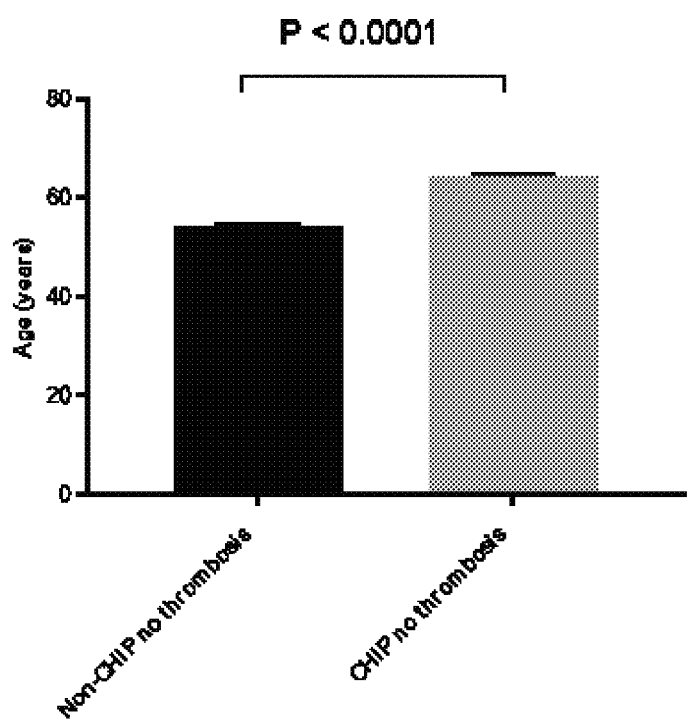
FIG. 15, continued

INHIBITION OF JAK-STAT SIGNALING INHIBITS FORMATION OF NEUTROPHIL EXTRACELLULAR TRAPS (NETS)

CLAIM OF PRIORITY

This application claims the benefit of U.S. Provisional Application Ser. No. 62/594,266, filed on Dec. 4, 2017. The entire contents of the foregoing are incorporated herein by reference.

FEDERALLY SPONSORED RESEARCH OR DEVELOPMENT

This invention was made with Government support under Grant No. HL082945 awarded by the National Institutes of Health. The Government has certain rights in the invention.

TECHNICAL FIELD

The methods described herein include methods for the treatment of subjects, e.g., normal subjects or subjects who have Clonal Hematopoiesis of Indeterminate Potential (CHIP) or a Philadelphia-negative myeloproliferative neoplasm (MPN), e.g., polycythaemia vera (PV) or essential thrombocythaemia (ET), using inhibitors of JAK-STAT signaling.

BACKGROUND

The Philadelphia chromosome-negative myeloproliferative neoplasms (MPNs) encompass a group of chronic, clonal stem-cell disorders with distinct disease phenotypes characterized by increased numbers of terminally differentiated blood cells. The majority of MPNs have a $JAK2^{V617F}$ somatic mutation, and most of the remaining cases have mutations in MPL or CALR that also activate the JAK-STAT signaling pathway (1). Thromboembolic complications are a major cause of morbidity and mortality, but the mechanistic basis for thrombophilia in these patients is not completely understood with several pathological processes implicated (2, 3).

SUMMARY

Provided herein are methods that include administering a JAK-STAT inhibitor to a subject to reduce NETosis. In one aspect, methods are provided for reducing risk of recurrence of a cardiovascular event in a subject who has had at least one cardiovascular event. The methods include identifying a subject who has had at least one cardiovascular event; determining the JAK2 genotype of the subject; selecting a subject who has a Jak2V617F genotype; and administering to the subject an effective amount of an inhibitor of JAK-STAT signaling.

Also provided are methods for reducing risk of occurrence or recurrence of a cardiovascular event in a subject, optionally a subject who has Clonal Hematopoiesis of Indeterminate Potential (CHIP), the method comprising administering to the subject an effective amount of an inhibitor of JAK-STAT signaling.

Also provided herein are methods for inhibiting formation of NETs in a subject, e.g., for reducing NETosis, or reducing the risk of NETosis-related conditions, comprising administering to the subject an effective amount of a JAK-STAT inhibitor.

In some embodiments, the subject is healthy, or has cancer, an autoimmune disease, Clonal Hematopoiesis of Indeterminate Potential (CHIP) or a Philadelphia-negative myeloproliferative neoplasm (MPN). In some embodiments, the MPN is polycythaemia vera (PV) or essential thrombocythaemia (ET). In some embodiments, the autoimmune disease is Antineutrophil cytoplasmic antibody (ANCA)-associated vasculitis (AAV), Systemic lupus erythematosus (SLE), Rheumatoid Arthritis (RA), psoriasis, Antiphospholipid syndrome (APS), multiple sclerosis (MS), dermatomyositis (DM), polymyositis (PM), and IgG4-related autoimmune pancreatitis (AIP), or a Drug-Induced Autoimmune Disease.

In some embodiments, the cardiovascular event is thrombosis or myocardial infarction (MI).

In some embodiments, the methods include determining the JAK2 genotype of the subject; and selecting a subject who has a Jak2V617F genotype. In some embodiments, determining the JAK2 genotype of the subject comprises determining a sequence of a portion of the subject's genome comprising a sequence encoding amino acid 617 of JAK2, and determining whether the sequence encodes a valine or a phenylalanine. In some embodiments, determining a sequence of a portion of the subject's genome comprises amplifying and/or sequencing a portion of the subject's genome comprising SEQ ID NO:1, and determining the identity of the nucleotide at position 26 of SEQ ID NO:1, and/or using a probe that hybridizes to the nucleotide at position 26 of SEQ ID NO:1.

In some embodiments, the methods include detecting NETosis in the subject, and administering an inhibitor or JAK-STAT signaling to a subject who has an amount of NETosis above a reference level (e.g., a level in a healthy subject or a disease reference who has a low level of NETosis). In some embodiments, the inhibitor of JAK-STAT signaling is selected from the group consisting of Tofacitinib (CP690,550); Baricitinib (INCB028050); Ruxolitinib (INCB018424); TG101348 (SAR302503); Lestaurtinib (CEP-701); AZD1480; R348; VX-509; GLPG0634; GSK2586184; AC-430; Pacritinib (SB1518); NS-018; CHZ868; INCB039110; Filgotinib (G-146034, GLPG-0634); Cerdulatinib (PRT062070); Gandotinib (LY-2784544); Momelotinib (GS-0387, CYT-387); PF-04965842); Upadacitinib (ABT-494); Peficitinib (ASP015K, JNJ-54781532); Fedratinib (SAR302503); and BMS-911543.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color.

Copies of this patent or patent application publication with color drawing(s) will be provided by the Office upon request and payment of the necessary fee.

Representative images of human neutrophils from healthy controls stimulated with PMA (10 nM) after 150 minutes of ex vivo pre-treatment with DMSO, ruxolitinb (300 nM), or GSK484 (10 μM, a PAD4 inhibitor). Scale bar=50 μm. (E) Lung tissue sections from mice expressing the $Jak2^{V617F}$ mutation as compared to $Jak2^{WT}$ mice. Scale bar=50 μm. (F) Charecterizing clot content in the lungs of $Jak2^{V617F}$ mice.

Hematoxylin and eosin (H&E) stain. Scale bar=200 μm. VWF—Von Willebrand factor. (G) Lung tissue sections from mice expressing the $Jak2^{V617F}$ mutation as compared to $Jak2^{WT}$ mice. Neutrophil infiltration and NETs are shown by neutrophil specific Ly6G (red) and $H3^{cit}$ (green) respectively. Scale bar=50 μm. (H) The percentages of mouse neutrophils with evidence of NET formation on morphological criteria (left) (n=9 for all genotype/treatment combinations) or $H3^{cit}$ positive staining (right) (n=6 for all genotype/treatment combinations) grouped by genotype after stimulation with 4 μM IO or DMSO for 2 hours. (I) Representative immunofluorescence images of mouse neutrophils derived from $Jak2^{WT}$ and $Jak2^{V617F}$ mice following stimulation with 4 μM IO or DMSO for 2 hours. DAPI in blue and $H3^{cit}$ in green. Scale bar=50 μm.

FIGS. 2A-F: $Jak2^{V617F}$ is associated with increased venous thrombosis tendency which is reversed with ruxolitinib. (A) Rates of thrombosis at 2 hours and 4 hours after surgical stenosis of the inferior vena cava (IVC) grouped according to genotype and in vivo treatment (vehicle or ruxolitinib 90 mg/Kg twice a day for 72 hours). 2 hours; $Jak2^{WT}$ vehicle n=8, $Jak2^{V617F}$ vehicle n=11, $Jak2^{V617F}$ ruxolitinib n=8. 4 hours; $Jak2^{WT}$ vehicle n=15, $Jak2^{V617F}$ vehicle n=14, $Jak2^{V617F}$ ruxolitinib n=14. (B) A representative image at 2 hours after IVC stenosis in a $Jak2^{WT}$ and a $Jak2^{V617F}$ mouse. (C). dsDNA plasma concentration in $Jak2^{WT}$ (n=13) and $Jak2^{V617F}$ (n=10) mice subjected to partial stenosis of the IVC. (D) Neutrophil infiltration and NET content of sections of thrombi harvested at 4 hours after IVC stenosis, as shown by neutrophil specific Ly6G (red) and $H3^{cit}$ (green) respectively. Scale bar=100 μm (E) The percentage of cells (DAPI) staining positively for $H3^{cit}$ in thrombi harvested at 4 hours after IVC stenosis.(F) The hematocrit (HCT), neutrophil count, and platelet count (PLT) in $Jak2^{V617F}$ mice after 72 hours of treatment with vehicle (n=36) or ruxolitinib (n=29) 90 mg/Kg twice a day.

Figure 3A:
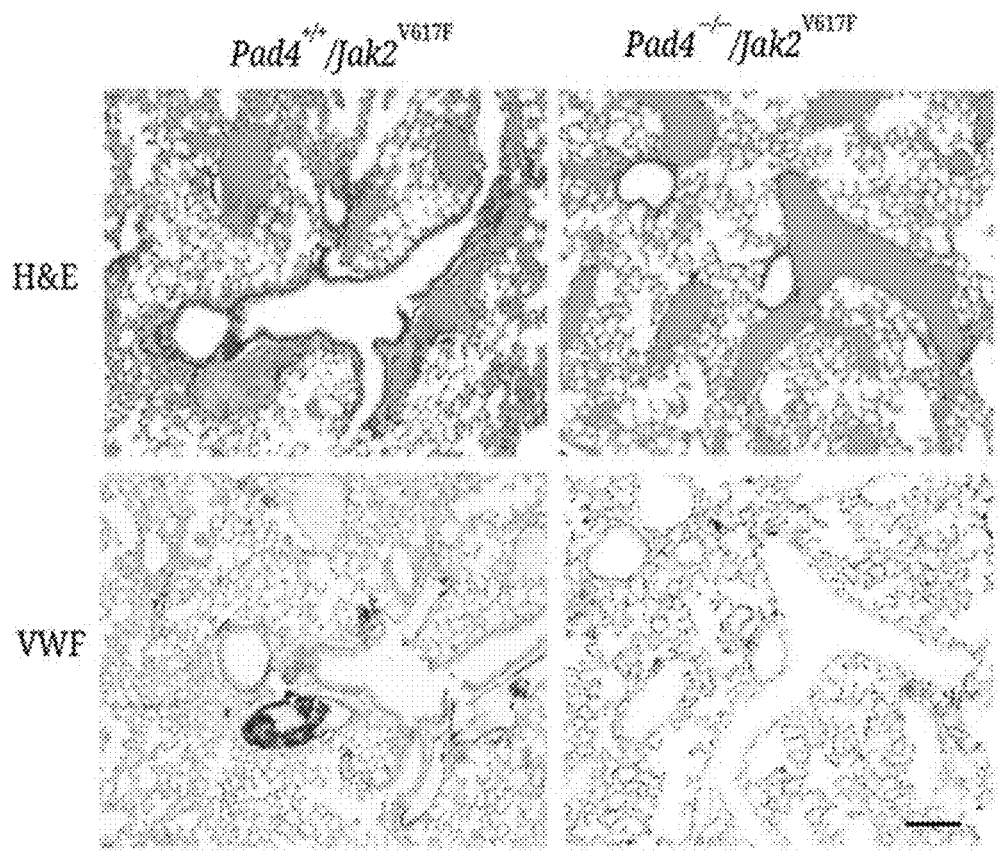
Figure 3B:
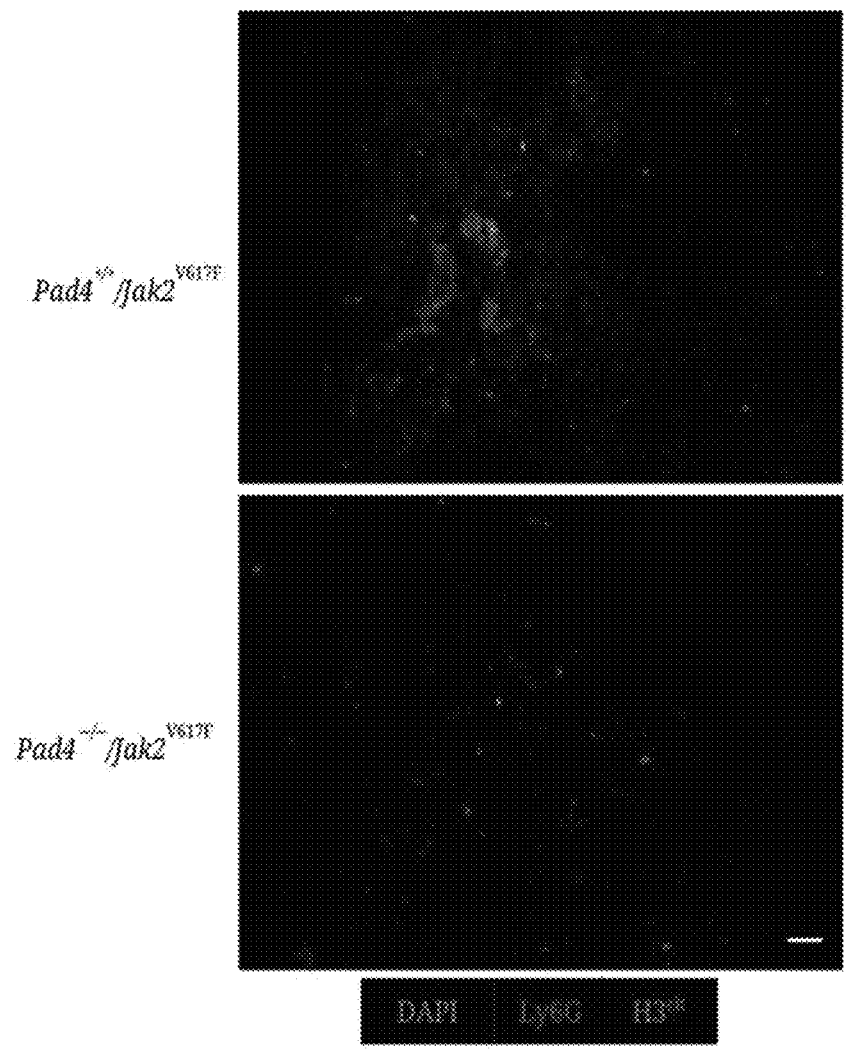
Figure 3C:
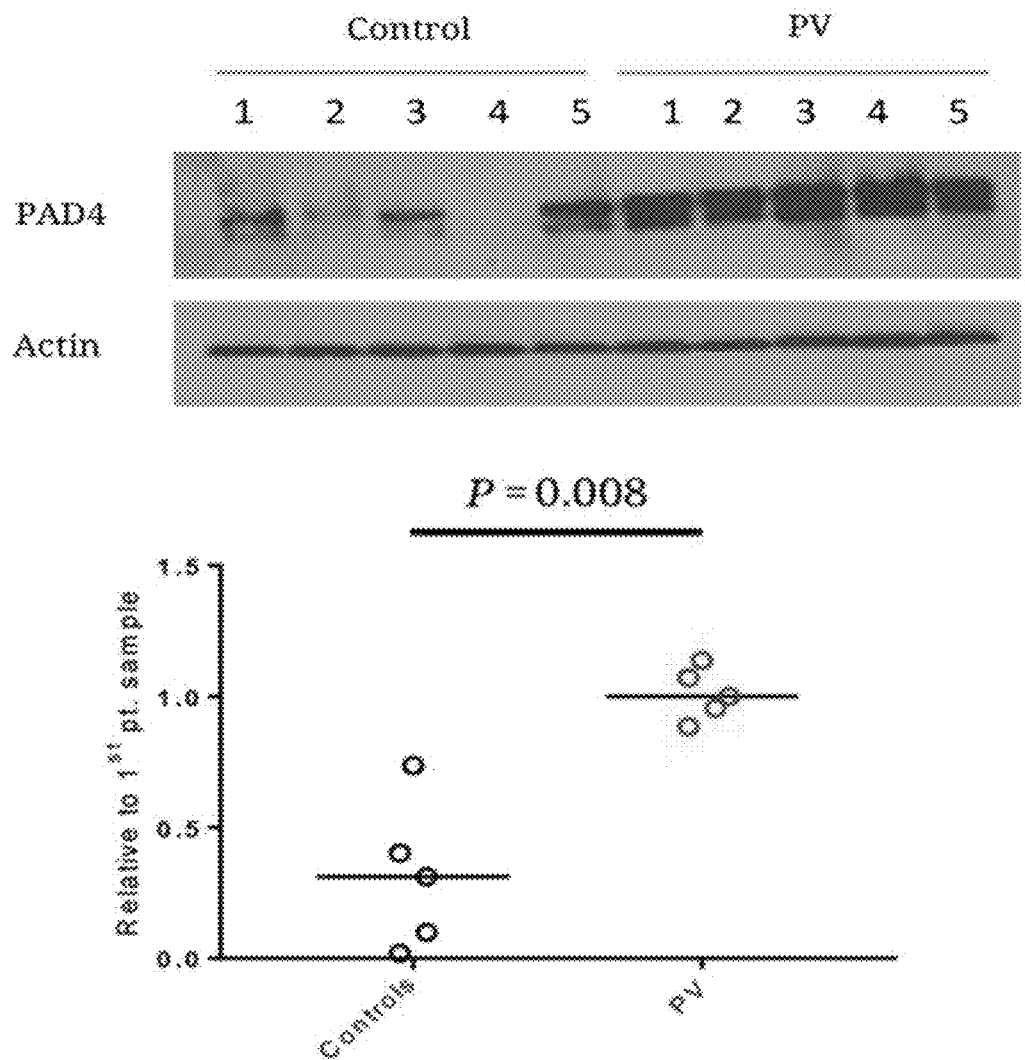

FIG. 3A-C: PAD4 is over expressed in MPNs and is essential for the NET-driven prothrombotic phenotype in $Jak2^{V617F}$-driven MPN mouse models. (A) Lung sections from mice 10 weeks after transplantation with $Pad4^{+/+}$ or $Pad4^{-/-}$ c-Kit positive cells transduced with $Jak2^{V617F}$ vector. Hematoxylin and eosin (H&E) stain. VWF—Von Willebrand factor. Scale bar=100 μm (B) Immunofluorescence studies of lung sections from mice 10 weeks after transplantation with $Pad4^{+/+}$ or $Pad4^{-/-}$ c-Kit cells transduced with $Jak2^{V617F}$ vector. Immunofluorescence studies demonstrate $H3^{cit}$ depositions in the background of hyper cellular lung section in $Pad4^{+/+}/Jak2^{V617F}$ mice as compared to $Pad4^{-/-}/Jak2^{V617F}$ mice. Neutrophil infiltration and NETs are shown by neutrophil specific Ly6G (red) and $H3^{cit}$ (green) respectively (C) PAD4 protein expression and quantification in isolated neutrophils from healthy controls and patients with polycythemia vera (PV) harboring the $JAK2^{V617F}$ mutation (actin used as loading control; representative image of 3 technical replicates; n=5 for both groups).

Figure 4A:
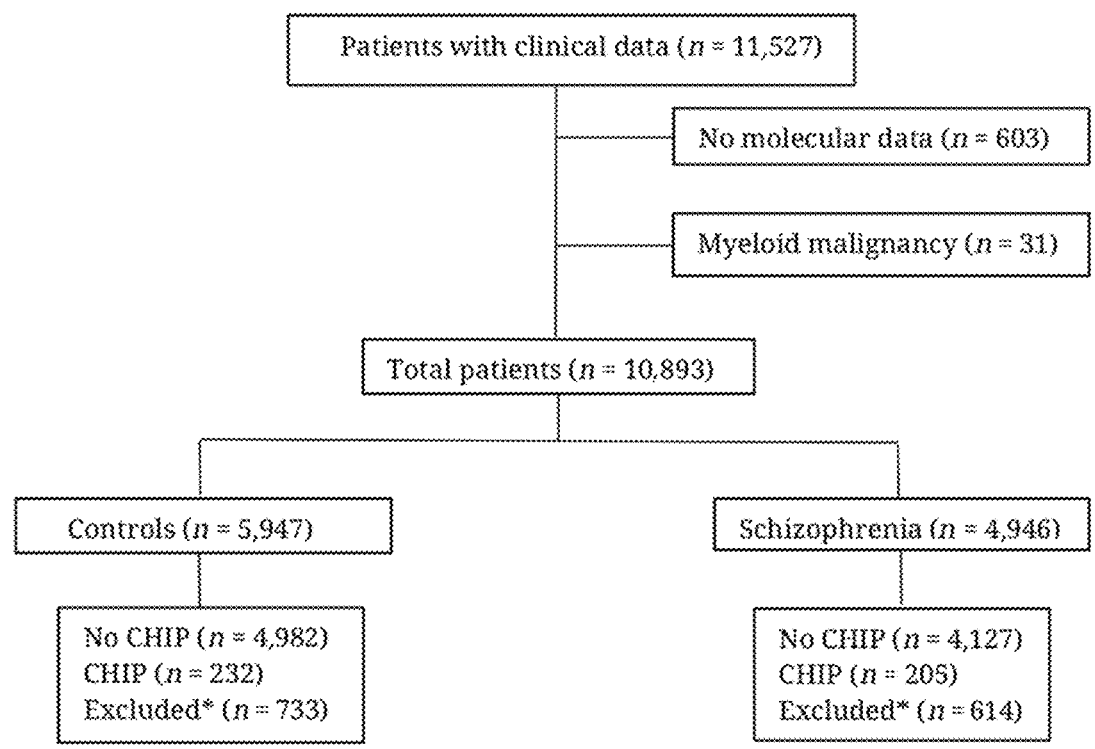
Figure 4B:
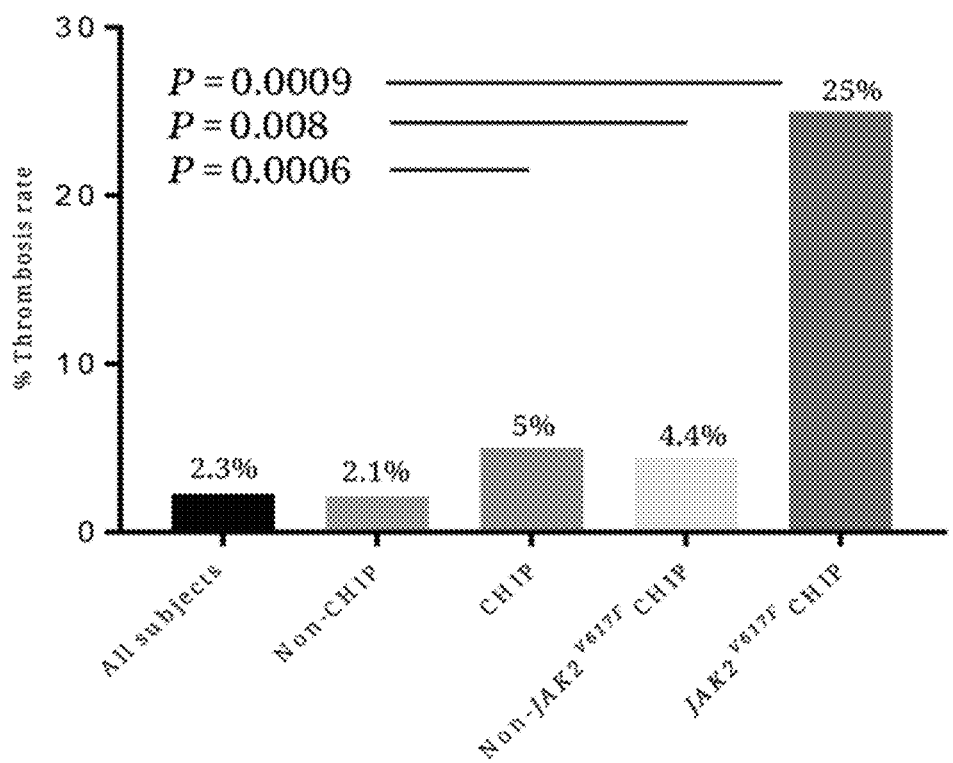
Figure 4C:
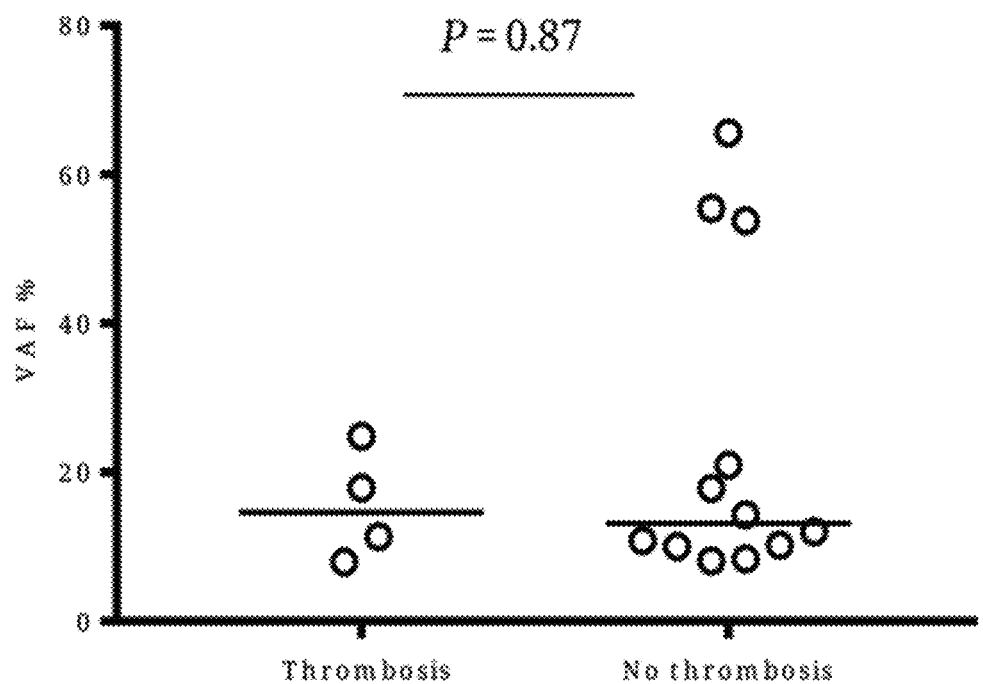

FIGS. 4A-C: $JAK2^{V617F}$ positive clonal hematopoiesis is associated with increase thrombosis rates. (A) CONSORT (Consolidated Standards of Reporting Trials) diagram of individuals in the population study. (B) Rates of venous thrombosis in patients with or without clonal hematopoiesis of indeterminate potential (CHIP) and/or $JAK2^{V617F}$ mutation. (C) Variant allele frequency (VAF) of individuals with $JAK2^{V617F}$ CHIP separated according to the incidence of venous thrombosis.

FIGS. 5A-D: Complementary studies of NET formation in neutrophils derived from MPN patients. (A) NET activation ratio in isolated neutrophils from healthy controls (n=7), patients with myelodysplastic syndrome (MDS) (n=4), and patients with myeloproliferative neoplasms (MPNs) (n=6). NET activation ratio represents the relative ratio of NET-associated elastase in resting and PMA-stimulated neutrophils. (B) Representative Wright-Giemsa staining of neutrophils after isolation from whole blood. Neutrophil purity is >90%. Scale bar=50 μm (C) Quantification of NETs as a percentage of total neutrophils in healthy controls (n=11) and patients with MPNs harboring $JAK2^{V617F}$ (n=10) after stimulation with 4 μM ionomycin (IO) or DMSO for 2 hours. Patients are in red and controls in black; empty squares denote patients with polycythemia vera (PV) and empty triangles denote patients with essential thrombocythemia (ET). (D) Representative Annexin V assay showing the percentage of early apoptotic neutrophils (in Q2) after 150 min of treatment with DMSO or ruxolitininb (300 nM).

Figure 6A:
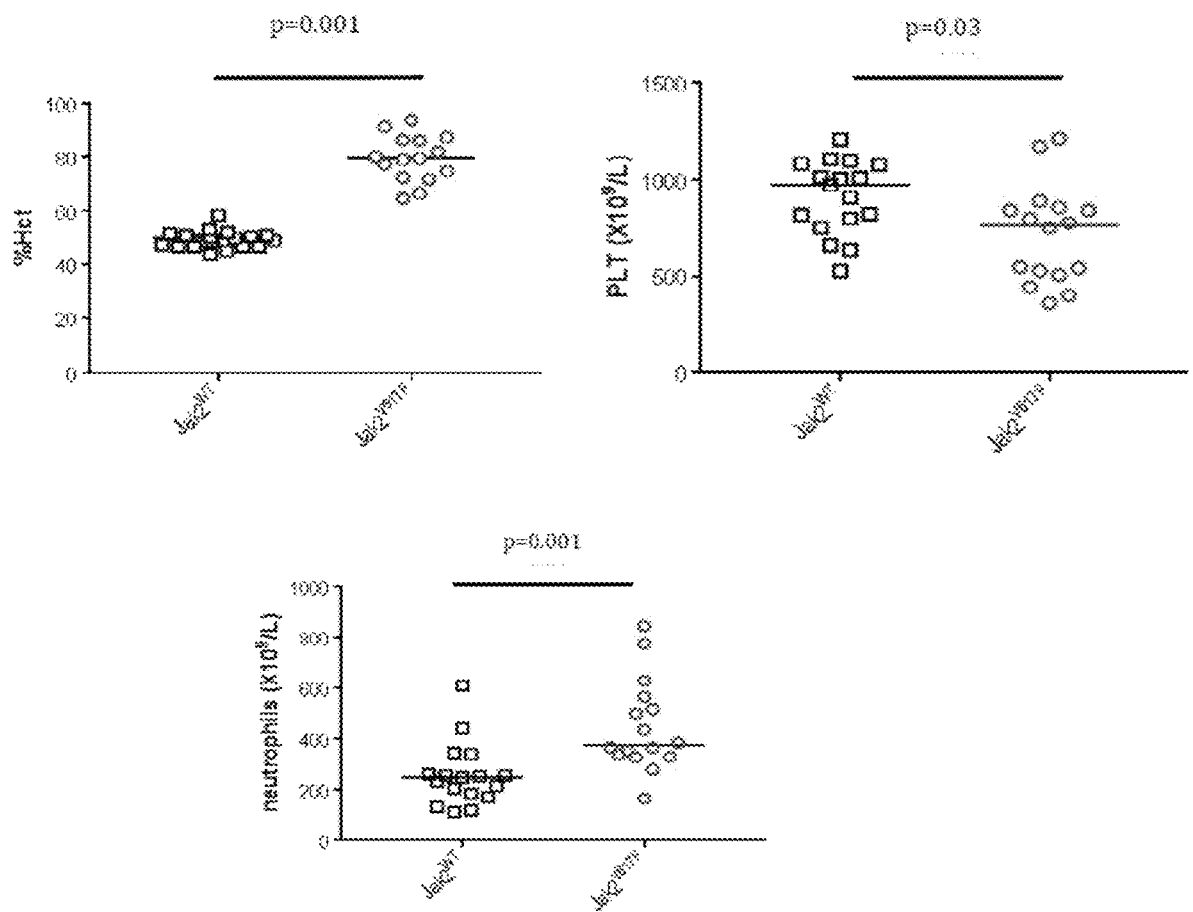
Figure 6B:
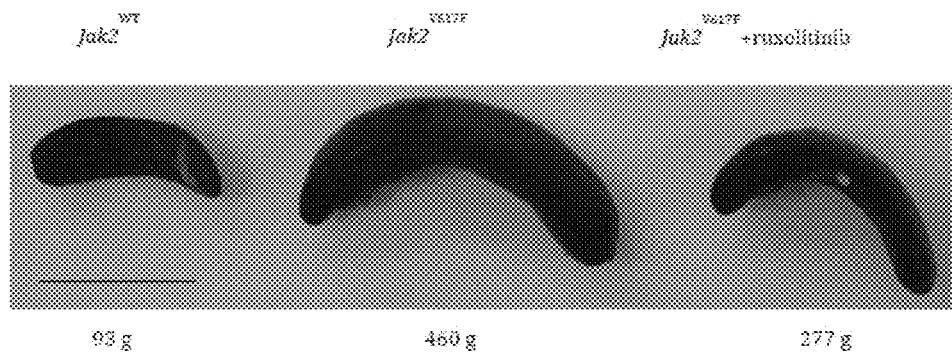

FIGS. 6A-B: $Jak2^{V617F}$-driven MPN mice demonstrate a phenotype reminiscent of Polycythemia-Vera. (A) Hematocrits (Hct) (n=15), platelet counts (PLT) (n=16), and neutrophil counts (n=16) of recipient mice engrafted with $Jak2^{V617F}$ or $Jak2^{WT}$ hematopoietic cells. (B) Spleens harvested from recipient mice engrafted with $Jak2^{V617F}$ or $Jak2^{WT}$ hematopoietic cells after 72 hours of treatment with either vehicle or ruxolitinib (90 mg/kg twice a day).

FIGS. 7A-D: Neutrophil, platelet, red blood cell and fibrin thrombi content. (A) Representative images of thrombi harvested from $Jak2^{WT}$ and $Jak2^{V617F}$ mice 4 hours after surgical stenosis of the inferior vena cava (IVC) stained for neutrophils (Ly6G in red) and DNA (DAPI, in blue). Vehicle and ruxolitinib indicates treatment received for 72 hours prior to surgery. Scale bar=100 μm (B) The percentage of neutrophils (LyG positive) in thrombi as a percentage of total cells (DAPI positive) (n=9). (C) Representative images of thrombi harvested from $Jak2^{WT}$ and $Jak2^{V617F}$ mice 4 hours after surgical stenosis of the inferior vena cava (IVC) stained for platelets (CD41, in red), DNA (DAPI, in blue) and $H3^{cit}$ (in green). Vehicle and Ruxolitinib indicates treatment received for 72 hours prior to surgery. Scale bar=100 μm (D) Martius Scarlet Blue trichrome staining demonstrates red blood cell content (yellow) and fibrin (red).

Figure 8A:
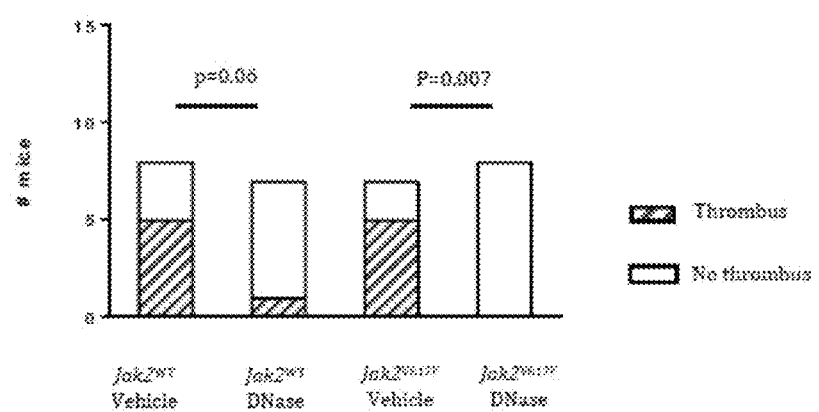
Figure 8B:
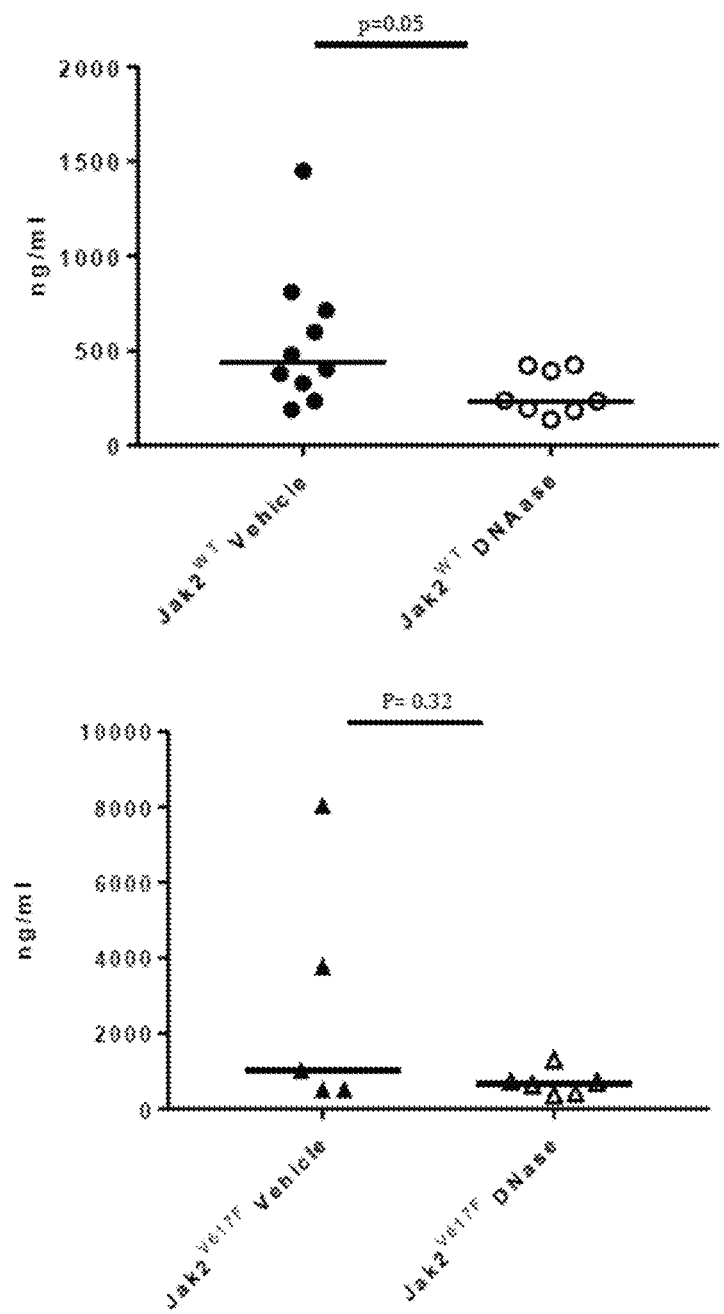
Figure 8C:
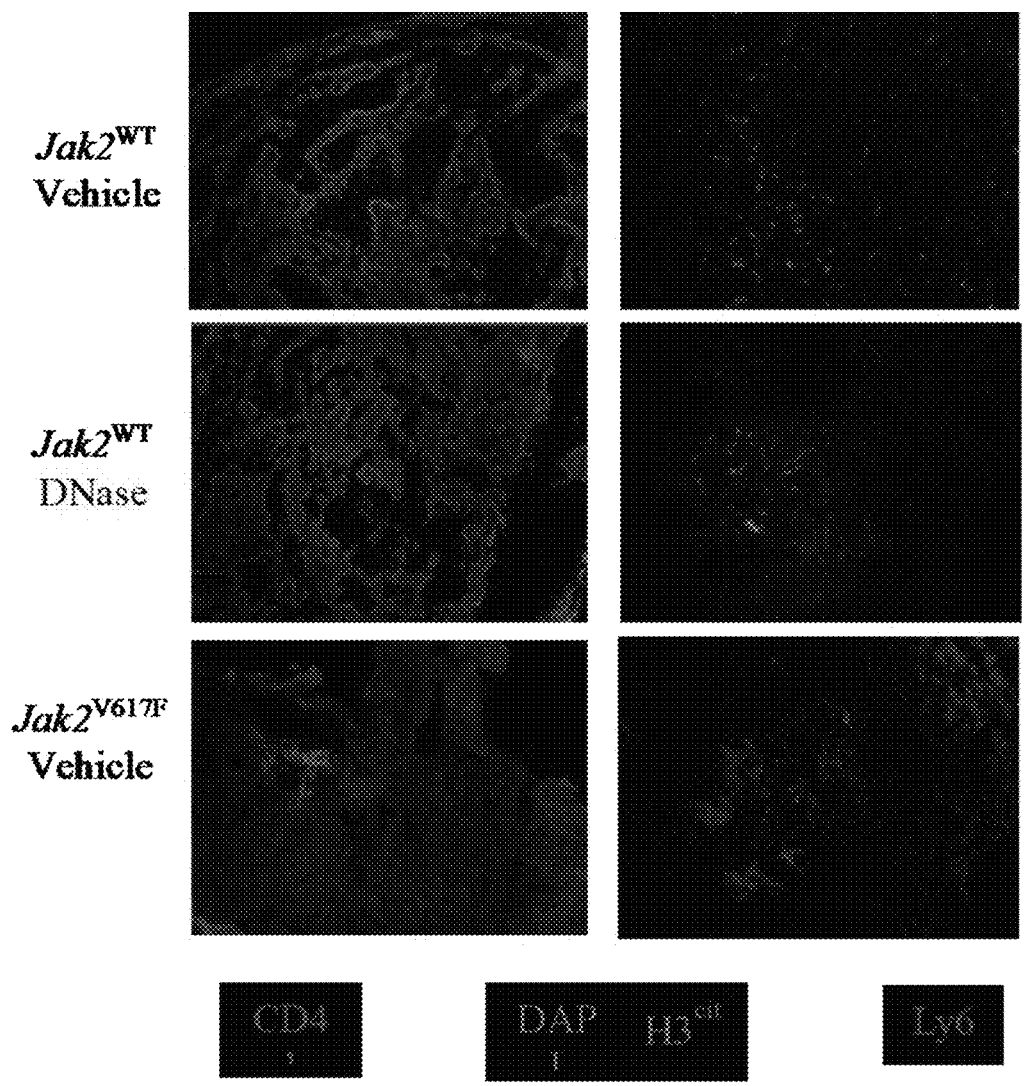

FIGS. 8A-C: The effect of DNase treatment on thrombosis rate in an inferior vena-cava partial ligation thrombosis model. (A) Rates of thrombosis at 2 hours and 4 hours after surgical stenosis of the inferior vena cava (IVC) according to genotype and treatment (vehicle or DNAse 50 µg intraperitoneally and 10 µg immediately after surgery). Jak2$^{WT}$ vehicle n=8, Jak2$^{WT}$ DNase n=7, Jak2$^{V617F}$ vehicle n=7, Jak2$^{V617F}$ DNase n=8. (B) Quantification of double-stranded DNA in plasma harvested 4 hours after partial ligation. Jak2$^{WT}$ vehicle n=10, Jak2$^{WT}$ DNase n=8, Jak2$^{V617F}$ vehicle n=5, Jak2$^{V617F}$ DNase n=6. (C) Representative images of thrombi harvested from the IVC after 4 hours of partial ligation showing nucleated cells (DAPI, blue), platelets (CD41, red, left panels), citrullinated H3 (green), and neutrophils (Ly6G red, right panels). Scale bar=100 µm.

Figure 9A:
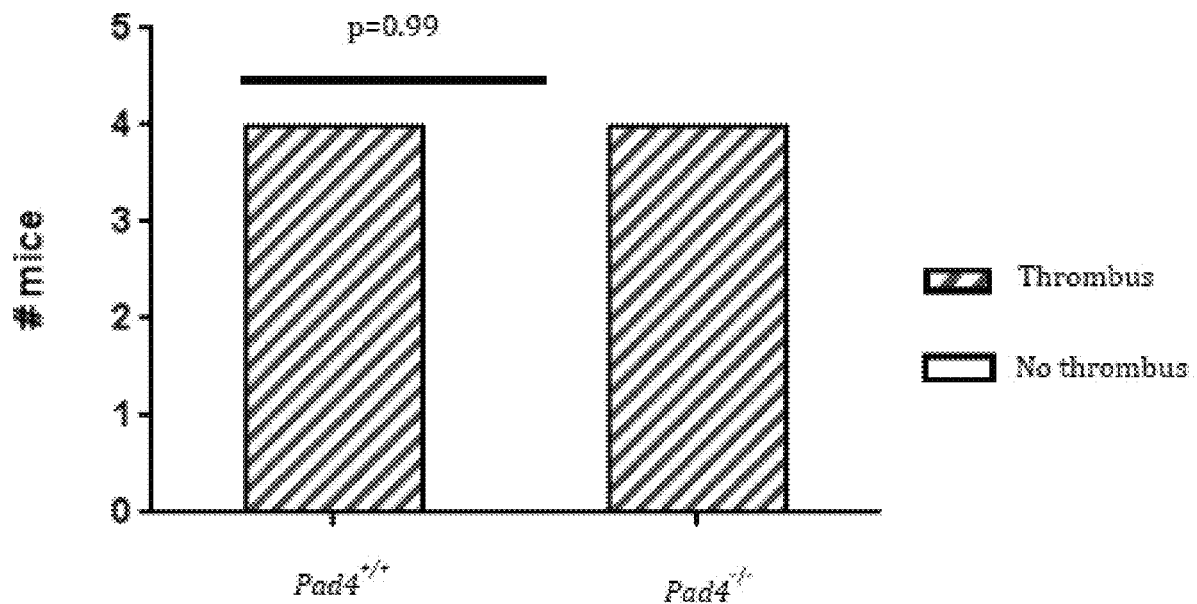
Figure 9B:
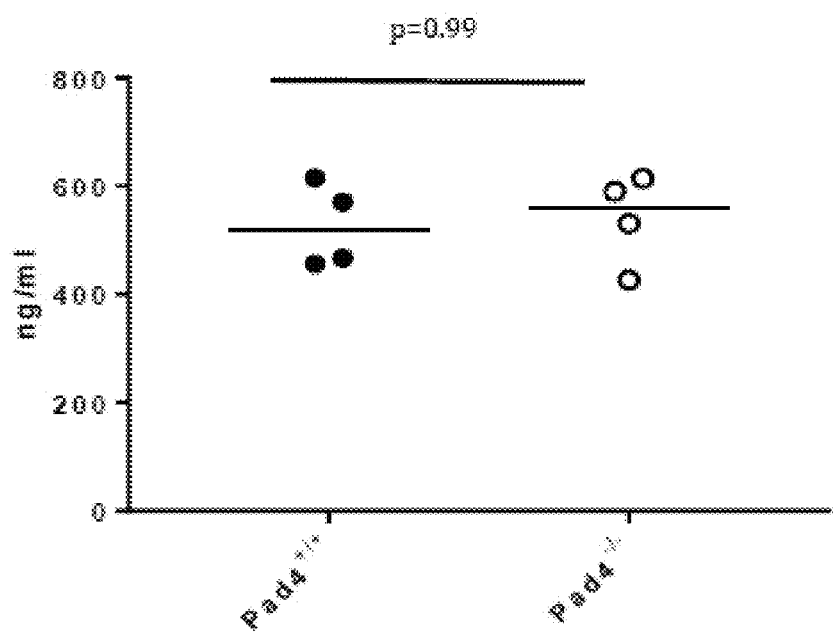
Figure 9C:
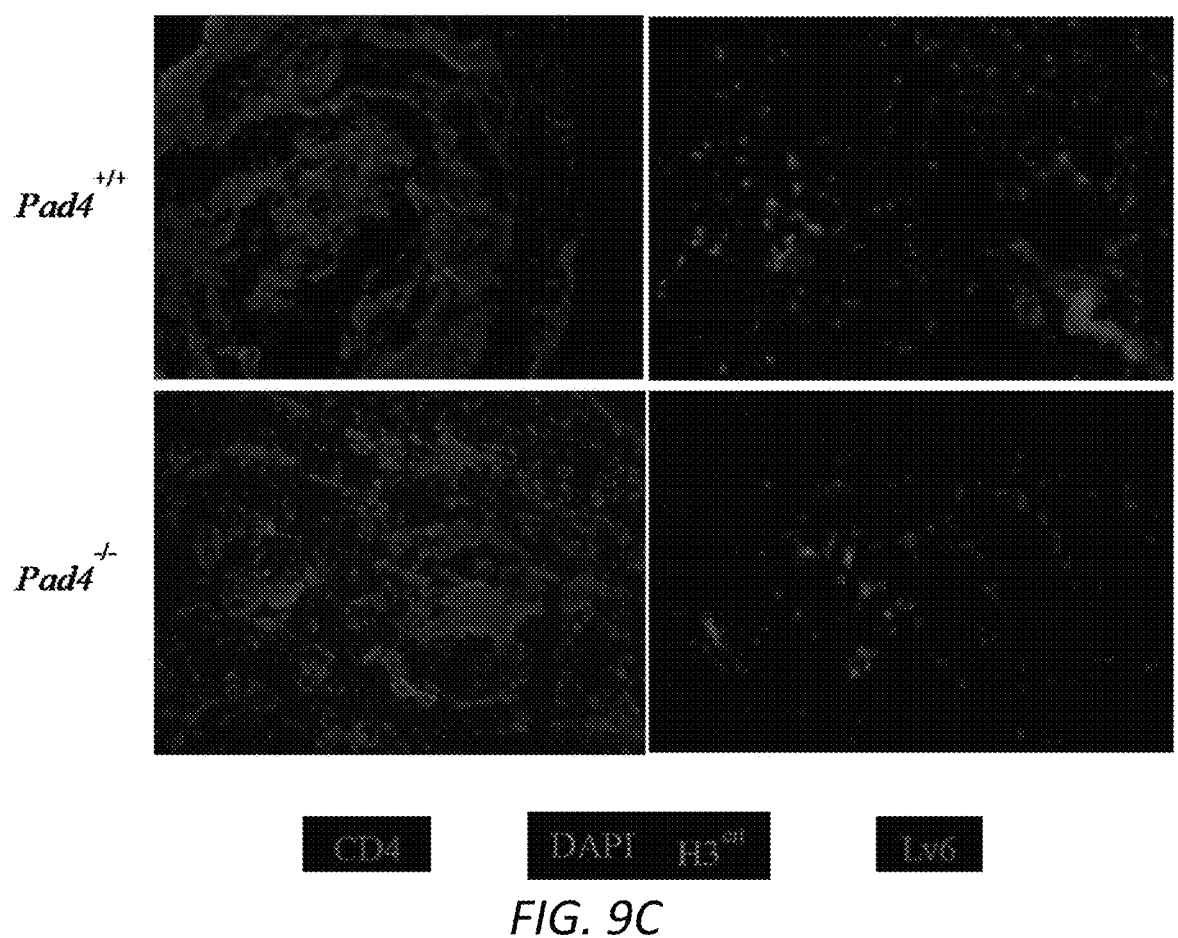

FIGS. 9A-C: Inferior vena-cava full ligation thrombosis model in Pad4$^{+/+}$ and Pad4$^{-/-}$ mice. (A) Rates of thrombosis in Pad4$^{+/+}$ (n=4) and Pad4$^{-/-}$ mice (n=4) 4 hours after full ligation of the inferior vena cava (IVC). (B) Quantification of double stranded DNA in plasma harvested after 4 hours in the same mice. (C) Representative images of thrombi harvested from the IVC after 4 hours of full ligation showing nucleated cells (DAPI, blue), platelets (CD41, red, left panels), citrullinated H3 (green), and neutrophils (Ly6G, red, right panels). Scale bar=100 µm.

Figure 10A:
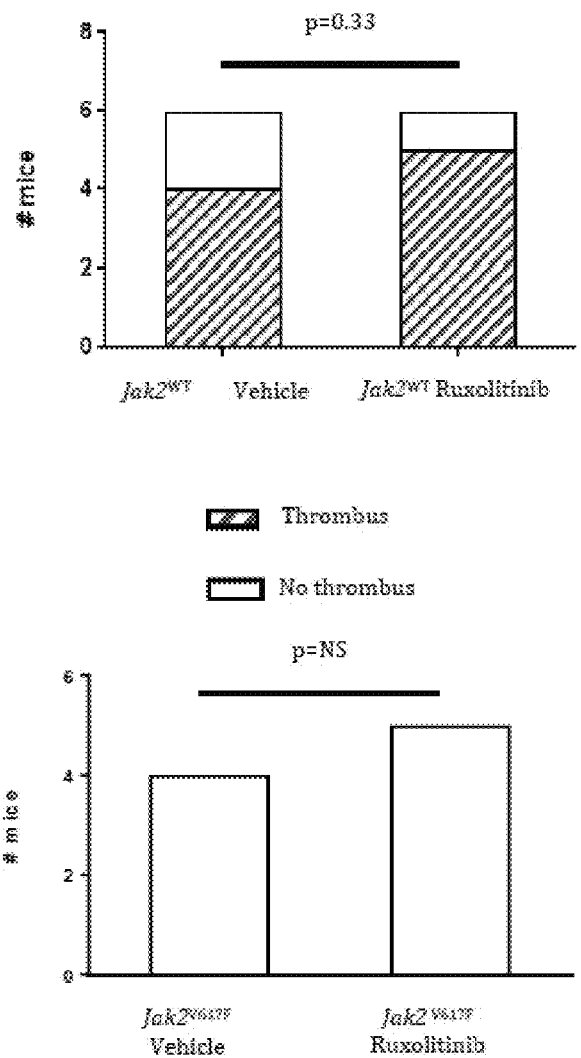
Figure 10B:
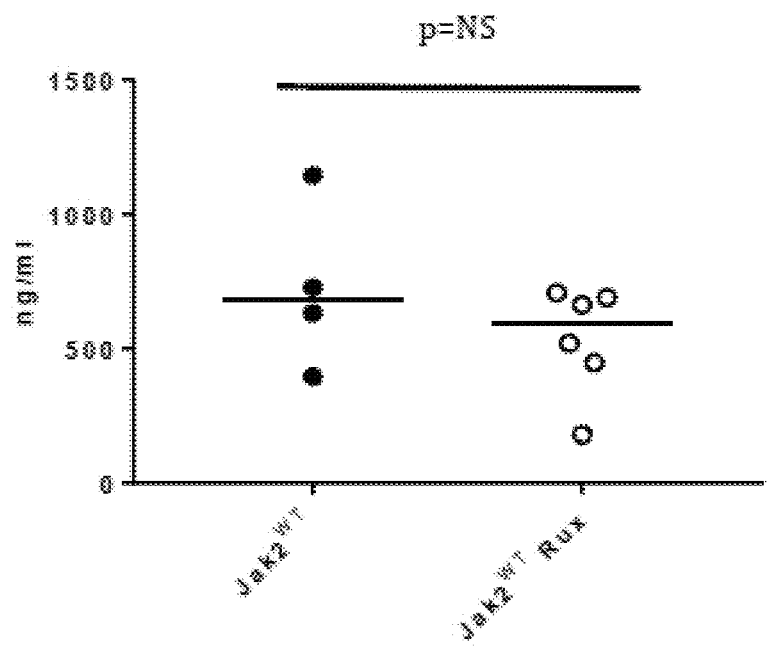
Figure 10C:
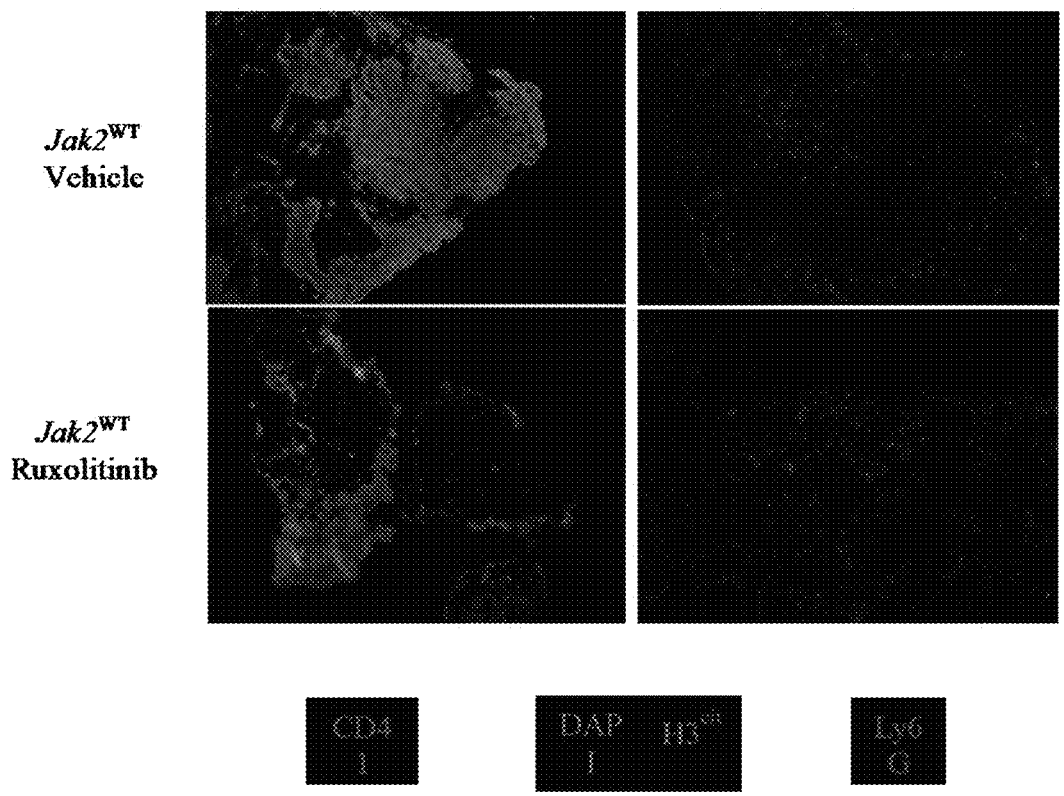

FIGS. 10A-C: Inferior vena-cava full ligation thrombosis model in Jak2$^{WT}$ and Jak2$^{V617F}$ with and without ruxolitinib treatment. (A) Rates of thrombosis in Jak2$^{WT}$ (n=6) and Jak2$^{V617F}$ (n=6) mice 4 hours after full ligation of the inferior vena cava (IVC). Mice had been treated for 72 hours treatment with either vehicle or ruxolitinib (90 mg/kg twice a day) prior to surgery. (B) Quantification of double stranded DNA in plasma harvested after 4 hours after ligation. (C) Representative images of thrombi harvested from the IVC after 4 hours of full ligation showing nucleated cells (DAPI, blue), platelets (CD41, red, left panels), citrullinated H3 (green), and neutrophils (Ly6G, red, right panels). Scale bar=100 µm.

Figure 11A:
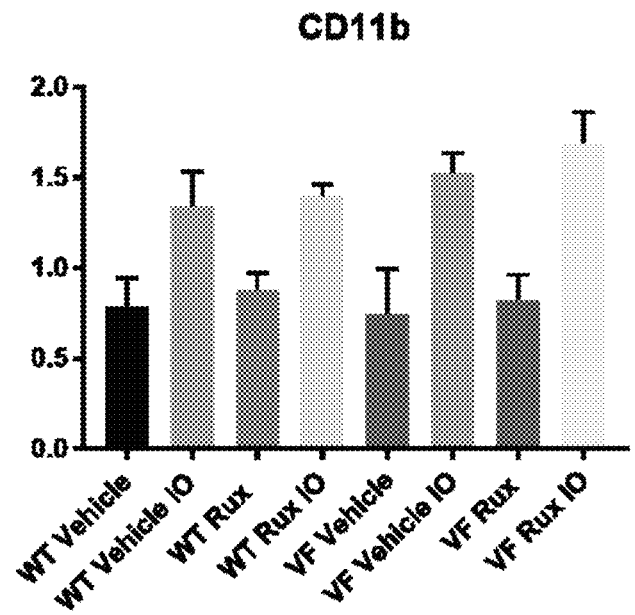
Figure 11B:
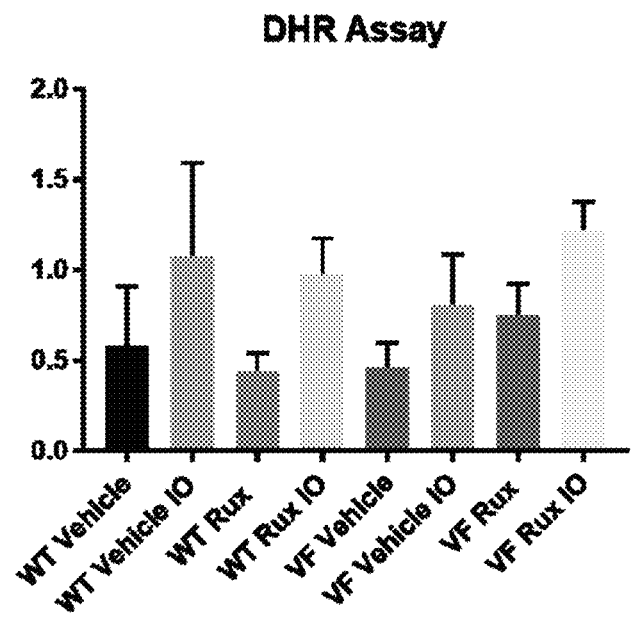

FIGS. 11A-B: Neutrophil activation and reactive oxygen species production in neutrophils from Jak2$^{WT}$ and Jak2$^{V617F}$ mice. Assessment of neutrophil activation (A) and reactive oxygen species production (B) in Jak2$^{WT}$ and Jak2$^{V617F}$ mice (n=8 per condition). These results represent the average from 4 mice per condition and results are normalized to the first result obtained in the Jak2$^{WT}$ vehicle condition.

Figure 12A:
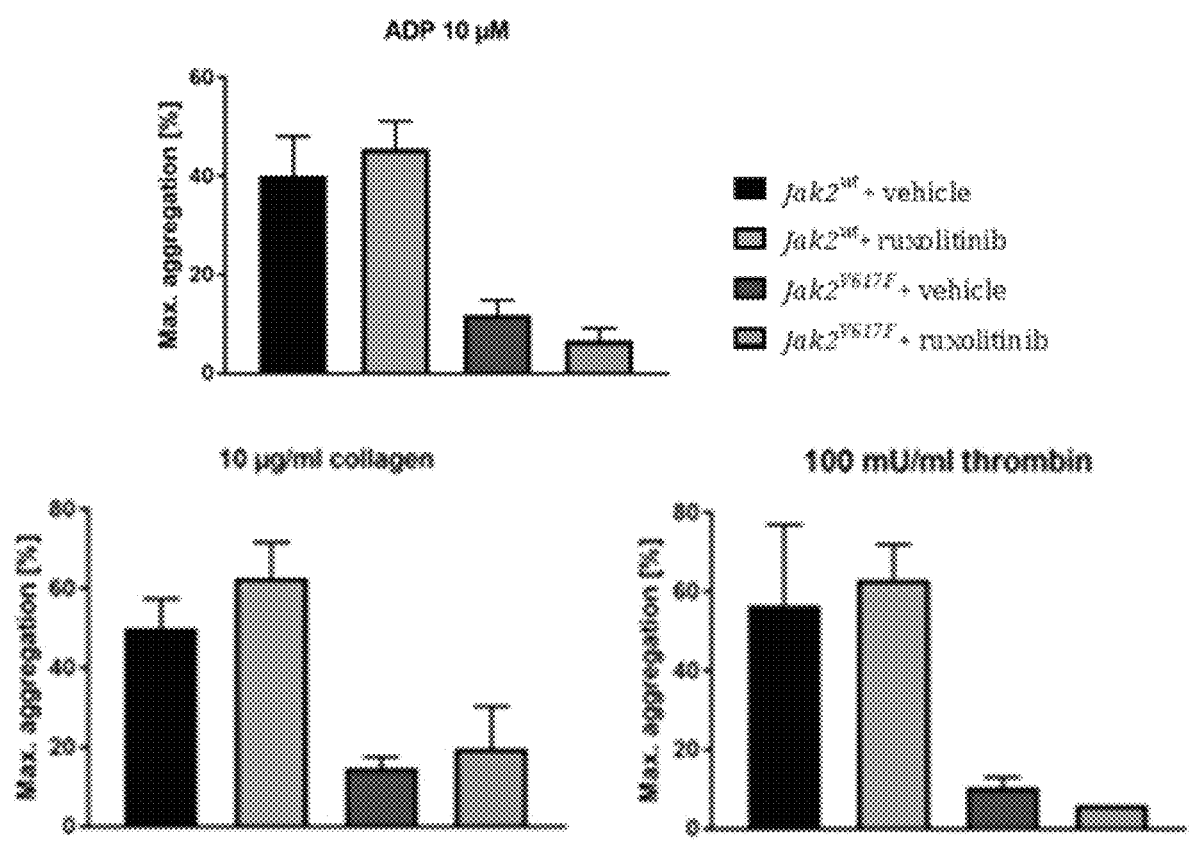
Figure 12B:
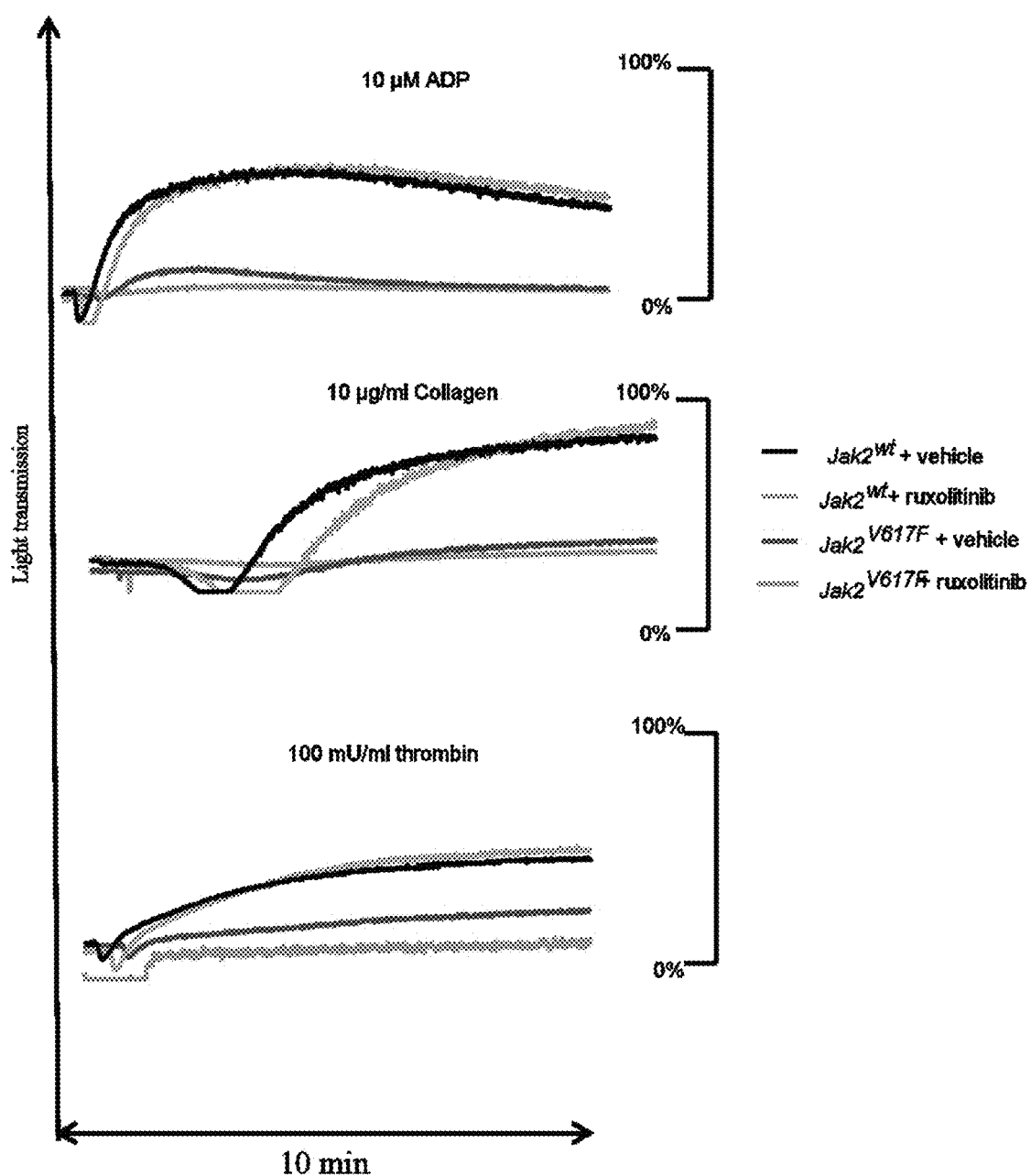
Figure 12C:
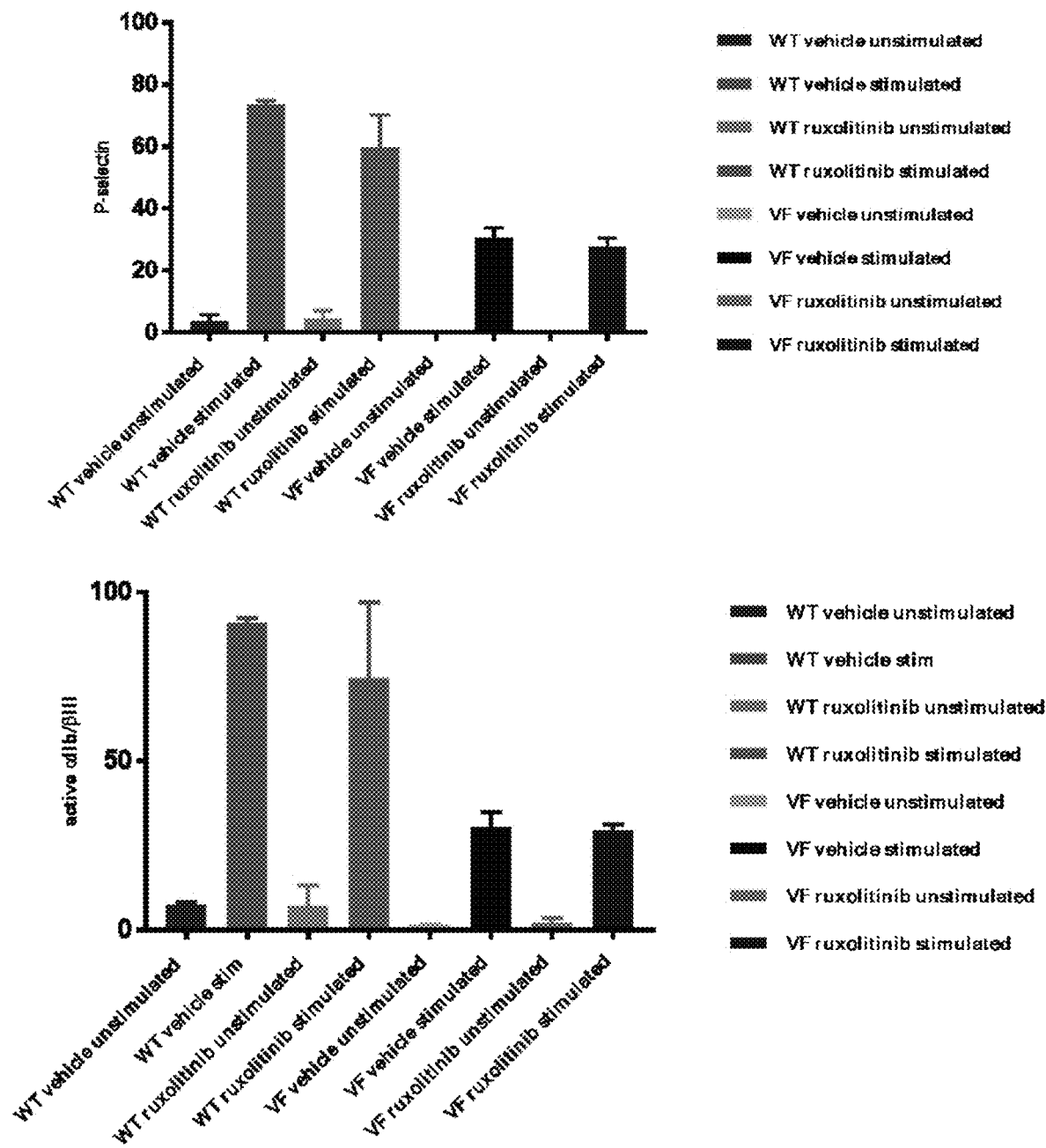

FIGS. 12A-C: Platelet function in Jak2$^{WT}$ and Jak2$^{V617F}$ mice. (A) Platelets aggregation studies in response to ADP, collagen or thrombin in platelets isolated from Jak2$^{WT}$ and Jak2$^{V617F}$ mice following 72 hours treatment with either vehicle or ruxolitinib (90 mg/kg twice a day. Data presented as mean±SEM (n=2-4 mice per condition) (B) Representative aggregometry traces. (C) Activation at baseline and after thrombin stimulation as assessed by flow cytometry with measurement of surface expression of P-selectin and αIIb/βIII (n=2 per condition).

Figure 13:
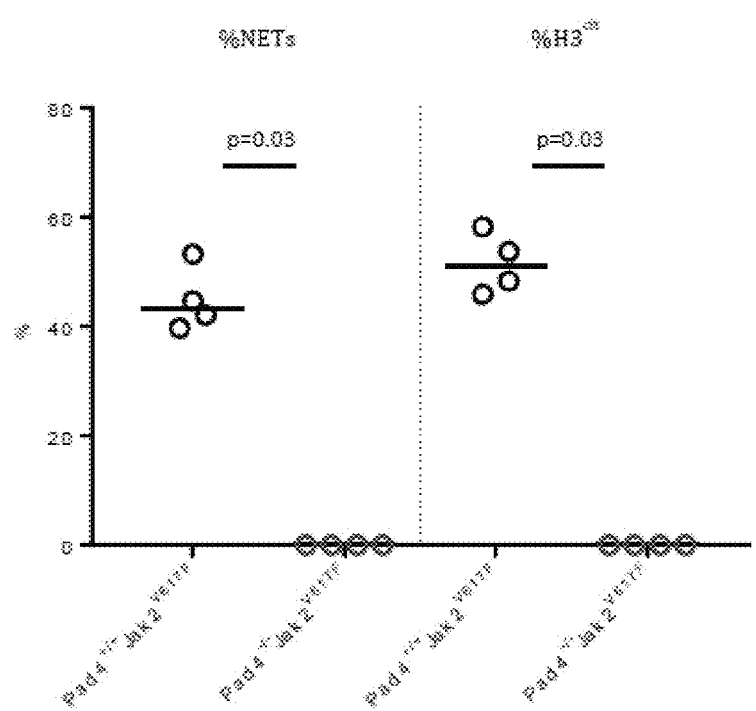

FIGS. 13: NET formation in neutrophils derived from mice engrafted with Jak2$^{V617F}$-expressing Pad4+/+ or Pad4−/− mice. The percentages of mouse neutrophils with evidence of NET formation on morphological criteria (left) (n=4 for all genotype/treatment combinations) or H3$^{cit}$ positive staining (right) (n=4 for all genotype/treatment combinations) grouped by genotype after stimulation with 4 µM IO or DMSO for 2 hours.

Figure 14:
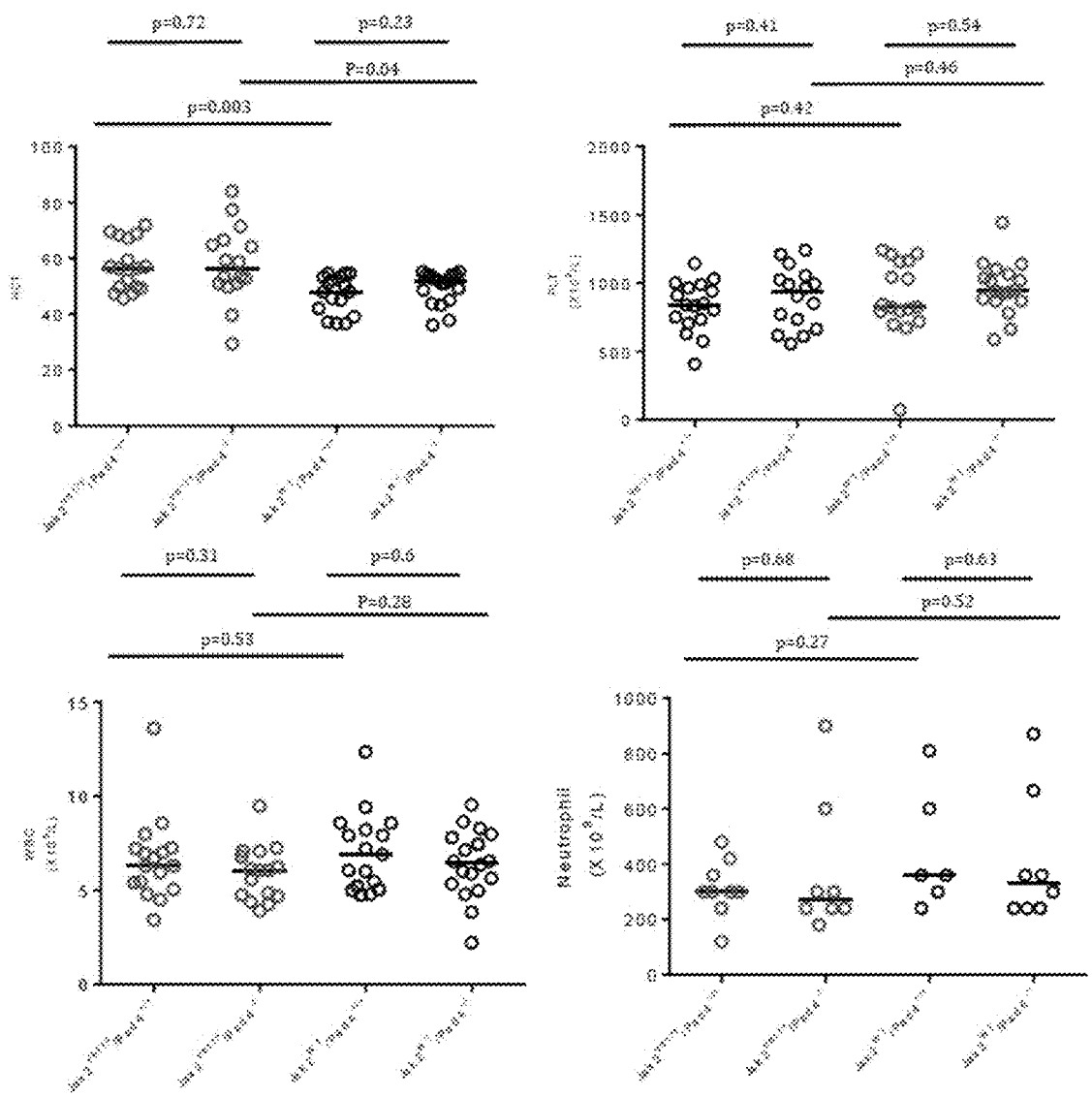

FIG. 14: Blood cell counts from Pad4 null mice (Pad4$^{-/-}$) and Pad4$^{+/+}$ controls transduced with Jak2$^{V617F}$ retrovirus and transplanted into lethally irradiated Jak2$^{WT}$ recipients. Jak2$^{V617F}$/Pad4$^{+/+}$ (n=17); Jak2$^{V617F}$/Pad4$^{-/-}$ (n=16); HCT—hematocrit; PLT—platelets; WBC—white blood cells.

Figure 15:
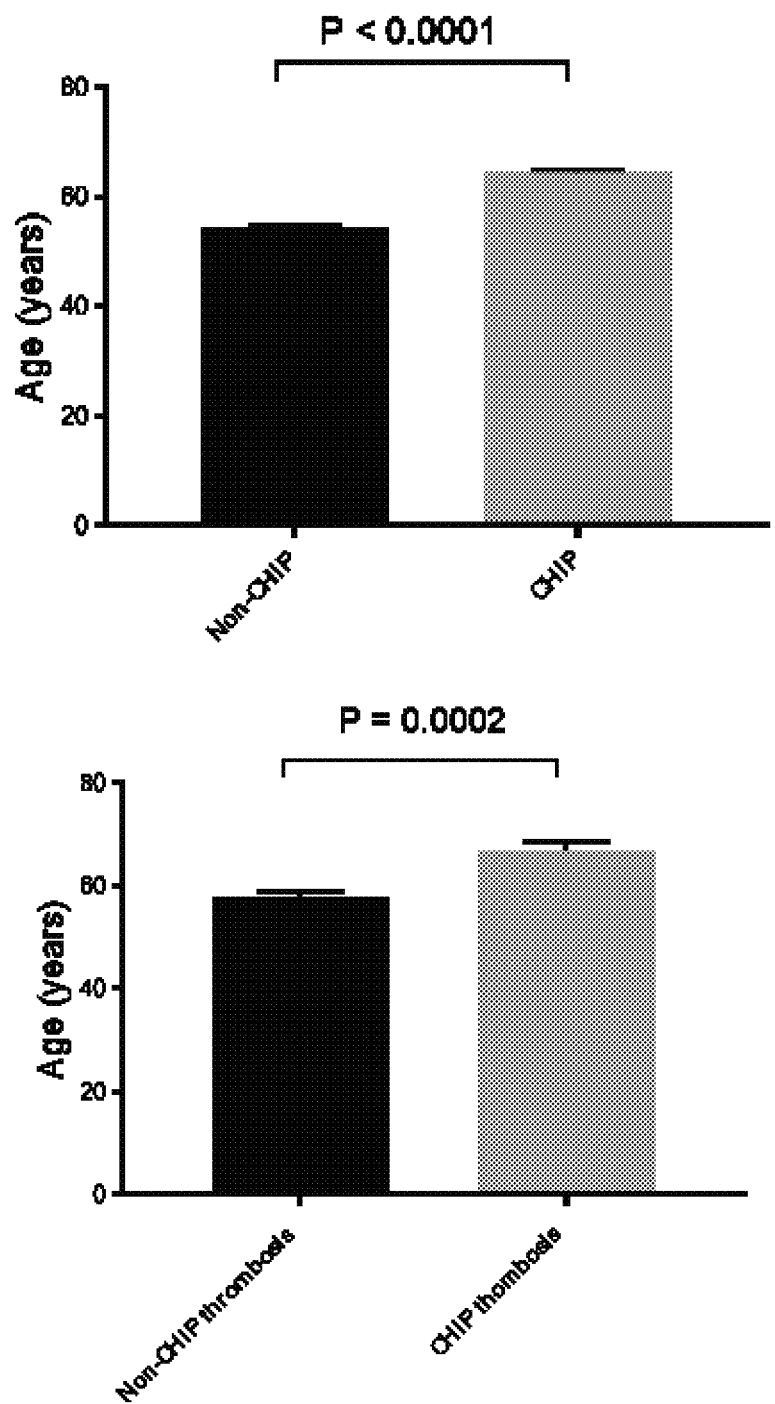

FIG. 15: Differences in age between persons with and without CHIP. (first graph) Median age for the whole CHIP and non-CHIP cohorts and for those with (second graph) and without (third graph) a venous thrombotic event.

DETAILED DESCRIPTION

NETosis is a form of neutrophil-specific cell death characterized by the release of large web-like structures referred to as neutrophil extracellular traps (NETs). NET formation, a component of innate immunity, has previously been linked to the pathogenesis of thrombosis (15). Without wishing to be bound by theory, this study offers a mechanism for the thrombotic tendency observed in certain conditions associated with NETosis including MPNs and other conditions described herein. As shown herein, JAK2$^{V617F}$ expression is associated with increased NET formation in response to neutrophil stimulation in MPN patients and in Jak2$^{V617F}$ mouse models. Although a previous study indicated that neutrophils from patients with MPN have impaired in vitro NET formation when stimulated with cytokines (33), the present results demonstrate increased NET formation in vitro in both Jak2$^{V617F}$ human and mouse neutrophils in response to ionomycin. Such apparently discrepant results may be the result of the different stimuli used, including the selective use of specific inflammatory cytokines in the previous study. In addition, the patient samples in the previous report indicated that circulating nucleosomes, one source of which is NETs, were significantly elevated in blood samples from individuals with MPNs, although the authors proposed that the nucleosomes are not NET derived in this setting. Moreover, the in vivo experiments performed herein found that increased NET formation was associated with increased thrombosis in Jak2$^{V617F}$ mice, and both NET formation and thrombosis were dependent on PAD4, an enzyme essential for citrullination of histones. Treatment with a JAK1/2 inhibitor abrogated NET formation in vitro and decreased thrombosis in Jak2$^{V617F}$ mice in vivo.

Ruxolitinib is currently FDA-approved for the treatment of intermediate and high-risk myelofibrosis and hydroxyurea-refractory PV (34, 35). In the RESPONSE trial, a large phase III study that led to the FDA approval of ruxolitinib for patients with PV not responding or intolerant to hydroxyurea, it is notable that there was a lower rate of thromboembolic events in the ruxolitinib-treated group (1.2 per 100 patient years with ruxolitinib v 2.8 for patients treated with other therapies) (34). See also Keohane et al., Haematologica. 2015 September; 100(9): e348-e350.

The present study focused on cardiovascular events, and on thrombotic events in particular, because NETs have been shown to be important for some types of myocardial infarction (MI). Because NETs are important for MI without the context of JAK2 mutations and we have shown that JAK-STAT inhibition can abrogate NETs in the cells of normal people, JAK-STAT inhibition could be used in any subject where NETs are part of the pathology. In the aggregate, our results suggest that JAK-STAT inhibition has a broader therapeutic utility in reducing NET formation and venous thrombosis, e.g., in patients with autoimmune diseases, cancer, MPNs including PV, and also in individuals with JAK2$^{V617F}$-mutant CHIP.

Methods of Treatment

The methods described herein include methods for the treatment of subjects, e.g., normal subjects, or subjects who have autoimmune diseases (e.g., Antineutrophil cytoplasmic antibody (ANCA)-associated vasculitis (AAV), Systemic lupus erythematosus (SLE), Rheumatoid Arthritis (RA), psoriasis, Antiphospholipid syndrome (APS), multiple sclerosis (MS), dermatomyositis (DM), polymyositis (PM), and IgG4-related autoimmune pancreatitis (AIP), or Drug-Induced Autoimmune Diseases, see He et al,. Chin Med J (Engl). 2018 Jul. 5; 131(13): 1513-1519; Lee et al., Autoimmun Rev. 2017 Nov.;16(11):1160-1173); atherosclerosis; cancer (see, e.g., Olsson and Cedarvall, Front Immunol. 2016; 7: 373; Cedarvall and Olsson, Oncoscience. 2015; 2(11): 900-901); Clonal Hematopoiesis of Indeterminate Potential (CHIP); or a Philadelphia-negative myeloproliferative neoplasm (MPN), e.g., polycythaemia vera (PV) or essential thrombocythaemia (ET). The methods can be used, e.g., for reducing NETosis, or reducing the risk of NETosis-related conditions, e.g., treating or reducing the risk of occurrence or reoccurrence of a cardiovascular event, e.g., thrombosis or myocardial infarction (MI). Generally, the methods include administering a therapeutically effective amount of an inhibitor of JAK-STAT signaling as described herein, to a subject who is in need of, or who has been determined to be in need of, such treatment. In some embodiments, the methods described herein include determining the subject's Jak2 Genotype, i.e., determining whether the subject has one or more JAK2V617F/I alleles, and selecting and treating subjects who do have one or more JAK2V617F/I alleles. In some embodiments, the subjects do not have one or more JAK2V617F/I alleles.

Methods for identifying subjects who have autoimmune diseases, cancer, CHIP or a Philadelphia-negative MPN, e.g., PV or ET, are known in the art. Based on information known in the art a skilled healthcare practitioner could readily make a diagnosis. See, e.g., McMullin et al., Br J Haematol. 2018 Nov. 27. doi: 10.1111/bjh.15648; Steensma et al., Blood. 2015 Jul. 2; 126(1):9-16; Heuser et al., Dtsch Arztebl Int. 2016 May 6; 113(18):317-22 Tefferi and Barbui, Am J Hematol. 2015 Feb.;90(2):162-73; Double and Harrison, Hematology. 2015 Mar;20(2):119-20.

In some embodiments, the methods can include detecting the presence of NETosis in a subject using methods known in the art and treating the subject as described herein.

JAK-STAT Inhibitors

A number of inhibitors or JAK-STAT signaling are known in the art, including Tofacitinib (CP690,550); Baricitinib (INCB028050); Ruxolitinib (INCB018424); TG101348 (SAR302503); Lestaurtinib (CEP-701); AZD1480; R348; VX-509; GLPG0634; GSK2586184; AC-430; Pacritinib (SB1518); NS-018; CHZ868; INCB039110; Filgotinib (G-146034, GLPG-0634); Cerdulatinib (PRT062070); Gandotinib (LY-2784544); Momelotinib (GS-0387, CYT-387); PF-04965842); Upadacitinib (ABT-494); Peficitinib (ASP015K, JNJ-54781532); Fedratinib (SAR302503); and BMS-911543; see, e.g., Furumoto and Gadina, BioDrugs. 2013 Oct.; 27(5): 431-438; Bose and Verstovsek, Blood. 2017 Jul. 13; 130(2): 115-125. In some embodiments, the inhibitor is or is not methotrexate.

JAK2 Genotyping

In some embodiments, the methods described herein include determining the subject's Jak2 Genotype, i.e., determining whether the subject has one or more JAK2V617F alleles.

As used herein, an "allele" is one of a pair or series of genetic variants of a polymorphism at a specific genomic location.

As used herein, "genotype" refers to the diploid combination of alleles for a given genetic polymorphism. A homozygous subject carries two copies of the same allele and a heterozygous subject carries two different alleles.

As used herein, a "haplotype" is one or a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more genetic markers in a given chromosomal region in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells;

individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2× SSC wash for 10 minutes at 45° C. followed by a 2× SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, "determining the identity of an allele" includes obtaining information regarding the identity, presence or absence of one or more specific alleles in a subject. Determining the identity of an allele can, but need not, include obtaining a sample comprising DNA from a subject, and/or assessing the identity, presence or absence of one or more genetic markers in the sample. The individual or organization who determines the identity of the allele need not actually carry out the physical analysis of a sample from a subject; the methods can include using information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

In some embodiments, to determine the identity of an allele or presence/absence of an allele or genotype described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for vitamin D deficiency if the subject has vitamin D deficiency. The presence or absence of the allele or genotype in a patient may be ascertained by using any of the methods described herein.

Methods of Determining the Identity of an Allele or Obtaining a Genotype

The methods described herein include determining the JAK2 genotype of a subject. In some embodiments, a JAK2 genotype is determined by detecting the identity of both alleles of the JAK2V617F single nucleotide polymorphism in the JAK2 gene (rs77375493) in a subject. Thus the methods can include obtaining and analyzing a sample from a subject. The mRNA sequence of JAK2 is available in GenBank at NM_004972.3. The SNP, plus flanking sequences, is shown in the following table A:

TABLE A

| JAK2 SNP rs77375493 | |
|---|---|
| SEQUENCE | SEQ ID NO: |
| TTTGGTTTTAAATTATGGAGTATGT[A/G/T]TCTGTGGAGACGAGAGTAAGTAAAA | 1 |

The reference sequence includes a G at position 26 of SEQ ID NO:1; a T at that position encodes the V617F pathogenic allele. An A at that position encodes the V617I allele. In some embodiments of the methods described herein, the presence of either the V617F or V617I genotype is used to identify or select subjects.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine or expectorant. The sample itself will typically consist of nucleated cells (e.g., blood or buccal cells) or tissue removed from the subject. The subject can be an adult or child. Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The absence or presence of an allele as described herein can be determined using methods known in the art. For example, gel electrophoresis, capillary electrophoresis, size exclusion chromatography, sequencing, and/or arrays can be used to detect the presence or absence of the allele or genotype. Amplification ofe nucleic acids, where desirable, can be accomplished using methods known in the art, e.g., PCR. In one example, a sample (e.g., a sample comprising genomic DNA), is obtained from a subject. The DNA in the sample is then examined to identify or detect the presence of an allele or genotype as described herein. The allele or genotype can be identified or determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

Other methods of nucleic acid analysis can include direct manual sequencing (Church and Gilbert, Proc. Natl. Acad. Sci. USA 81:1991-1995 (1988); Sanger et al., Proc. Natl. Acad. Sci. USA 74:5463-5467 (1977); Beavis et al., U.S. Pat. No. 5,288,644); automated fluorescent sequencing; next generation sequencing; single-stranded conformation polymorphism assays (SSCP) (Schafer et al., Nat. Biotechnol. 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)); denaturing high performance liquid chromatography (DHPLC, Underhill et al., Genome Res. 7:996-1005 (1997)); infrared matrix-assisted laser desorption/ionization (IR-MALDI) mass spectrometry (WO 99/57318); mobility shift analysis (Orita et al., Proc. Natl. Acad. Sci. USA 86:2766-2770 (1989)); restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, and combinations of such methods. See, e.g., Gerber et al., U.S. Patent Publication No. 2004/0014095 which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderbom et al., Genome Research 10(8):1249-1258 (2000)). Additional methods include, for example, PCR amplification in combination with denaturing high performance liquid chromatography (dHPLC) (Underhill et al., Genome Research 7(10):996-1005 (1997)).

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. PCR refers to procedures in which target nucleic acid (e.g., genomic DNA) is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. See e.g., PCR Primer: A Laboratory Manual, Dieffenbach and Dveksler, (Eds.); McPherson et al., PCR Basics: From Background to Bench (Springer Verlag, 2000); Mattila et al., Nucleic Acids Res., 19:4967 (1991); Eckert et al., PCR Methods and Applications, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, Genomics 4:560 (1989), Landegren et al., Science 241:1077 (1988), transcription amplification (Kwoh et al., Proc. Natl. Acad. Sci. USA 86:1173 (1989)), self-sustained sequence replication (Guatelli et al., Proc. Nat. Acad. Sci. USA 87:1874 (1990)), and nucleic acid based sequence amplification (NASBA). Guidelines for selecting primers for PCR amplification are well known in the art. See, e.g., McPherson et al., PCR Basics: From Background to Bench, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction.

Real-time quantitative PCR can also be used to determine copy number. Quantitative PCR permits both detection and quantification of specific DNA sequence in a sample as an absolute number of copies or as a relative amount when normalized to DNA input or other normalizing genes. A key feature of quantitative PCR is that the amplified DNA product is quantified in real-time as it accumulates in the reaction after each amplification cycle. Methods of quantification can include the use of fluorescent dyes that intercalate with double-stranded DNA, and modified DNA oligonucleotide probes that fluoresce when hybridized with a complementary DNA. Methods of quantification can include determining the intensity of fluorescence for fluorescently tagged molecular probes attached to a solid surface such as a microarray.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., Bioconjugate Chemistry, The American Chemical Society, 5:1 (1994)). The PNA probe can be designed to specifically hybridize to a nucleic acid comprising a polymorphic variant conferring susceptibility to or indicative of the presence of a given JAK2 genotype.

In some cases, allele-specific oligonucleotides can also be used to detect the presence of a polymorphic variant. For example, polymorphic variants can be detected by performing allele-specific hybridization or allele-specific restriction digests. Allele specific hybridization is an example of a method that can be used to detect sequence variants, including complete genotypes of a subject (e.g., a mammal such as a human). See Stoneking et al., Am. J. Hum. Genet. 48:370-382 (1991); and Prince et al., Genome Res. 11:152-162 (2001). An "allele-specific oligonucleotide" (also referred to herein as an "allele-specific oligonucleotide probe") is an oligonucleotide that is specific for particular a polymorphism can be prepared using standard methods (see Ausubel et al., Current Protocols in Molecular Biology, supra). Allele-specific oligonucleotide probes typically can be approximately 10-50 base pairs, preferably approximately 15-30 base pairs, that specifically hybridizes to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al., Nature (London) 324:163-166 (1986).

In some embodiments, allele-specific restriction digest analysis can be used to detect the existence of a polymorphic variant of a polymorphism, if alternate polymorphic variants of the polymorphism result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see Ausubel et al., Current Protocols in Molecular Biology, supra). The digestion pattern of the relevant DNA fragment indicates the presence or absence of a particular polymorphic variant of the polymorphism and is therefore indicative of the presence of a specific VDBP genotype. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., Genome Research 9(5):492-498 (1999)). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., Current Protocols in Molecular Biology, supra), and the blot contacted with the oligonucleotide probe. The presence of specific hybridization of the probe to the DNA is then detected. Specific hybridization of an allele-specific oligonucleotide probe (specific for a polymorphic variant shown in Table A) to DNA from the subject is indicative of the presence of a given VDBP genpotype.

The methods typically include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

Additional methods of nucleic acid analysis to detect polymorphisms and/or polymorphic variants can include, e.g., microarray analysis. In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about 1×106 nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

The probe can be a test probe such as a probe that can be used to detect polymorphisms in a region described herein (e.g., polymorphisms as described herein). For example, the probe can hybridize to an allele described herein, e.g., in Table A.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits. Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem. 73(1):6-22 (1998); Wheeless et al., Cytometry 17:319-326 (1994); and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.). Fluorescently labeled probes can be viewed with a fluorescence microscope and an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as 32P and 3H. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

In another aspect, this document features arrays that include a substrate having a plurality of addressable areas, and methods of using them. At least one area of the plurality includes a nucleic acid probe that binds specifically to a sequence comprising a polymorphism listed in Table A, and can be used to detect the absence or presence of said polymorphism, e.g., one or more SNPs, microsatellites, minisatellites, or indels, as described herein, to determine or identify an allele or genotype. For example, the array can include one or more nucleic acid probes that can be used to detect a polymorphism listed in Table A. In some embodiments, the probes are nucleic acid capture probes.

Generally, microarray hybridization is performed by hybridizing a nucleic acid of interest (e.g., a nucleic acid encompassing a polymorphic site) with the array and detecting hybridization using nucleic acid probes. In some cases, the nucleic acid of interest is amplified prior to hybridization. Hybridization and detecting are generally carried out according to standard methods. See, e.g., Published PCT Application Nos. WO 92/10092 and WO 95/11995, and U.S. Pat. No. 5,424,186. For example, the array can be scanned to determine the position on the array to which the nucleic acid hybridizes. The hybridization data obtained from the scan is typically in the form of fluorescence intensities as a function of location on the array.

Arrays can be formed on substrates fabricated with materials such as paper, glass, plastic (e.g., polypropylene, nylon, or polystyrene), polyacrylamide, nitrocellulose, silicon, optical fiber, or any other suitable solid or semisolid support, and can be configured in a planar (e.g., glass plates, silicon chips) or three dimensional (e.g., pins, fibers, beads, particles, microtiter wells, capillaries) configuration. Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide hybridization probes capable of specifically hybridizing to different polymorphic variants. Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Oligonucleotide probes forming an array may be attached to a substrate by any number of techniques, including, without limitation, (i) in situ synthesis (e.g., high-density oligonucleotide arrays) using photolithographic techniques; (ii) spotting/printing at medium to low density on glass, nylon or nitrocellulose; (iii) by masking, and (iv) by dot-blotting on a nylon or nitrocellulose hybridization membrane. Oligonucleotides can be immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Alternatively, oligonucleotides can be non-covalently immobilized on a substrate by hybridization to anchors, by means of magnetic beads, or in a fluid phase such as in microtiter wells or capillaries. Immobilized oligonucleotide probes are typically about 20 nucleotides in length, but can vary from about 10 nucleotides to about 1000 nucleotides in length.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments. General descriptions of using oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments.

The methods described herein can include providing an array as described herein; contacting the array with a sample (e.g., a portion of genomic DNA that includes at least a portion of a human chromosome), and detecting binding of a nucleic acid from the sample to the array. Optionally, the method includes amplifying nucleic acid from the sample, e.g., genomic DNA that includes a portion of a human chromosome described herein prior to or during contact with the array.

In some aspects, the methods described herein can include using an array that can ascertain differential expression patterns or copy numbers of one or more genes in samples from normal and affected individuals (see, e.g., Redon et al., Nature 444(7118):444-54 (2006)). For example, arrays of probes to a marker described herein can be used to measure polymorphisms between DNA from a subject having a specific JAK2 genotype, and control DNA, e.g., DNA obtained from an individual that does not that JAK2 genotype. Since the clones on the array contain sequence tags, their positions on the array are accurately known relative to the genomic sequence. Methods for array production, hybridization, and analysis are described, e.g., in Snijders et al., Nat. Genetics 29:263-264 (2001); Klein et al., Proc. Natl Acad. Sci. USA 96:4494-4499 (1999); Albertson et al., Breast Cancer Research and Treatment 78:289-298 (2003); and Snijders et al., "BAC microarray based comparative genomic hybridization," in: Zhao et al. (eds), Bacterial Artificial Chromosomes: Methods and Protocols, Methods in Molecular Biology, Humana Press, 2002.

In another aspect, this document provides methods of determining the absence or presence of a JAK2 genotype as described herein, using an array described above. The methods can include providing a two dimensional array having a plurality of addresses, each address of the plurality being positionally distinguishable from each other address of the plurality having a unique nucleic acid capture probe, contacting the array with a sample from a test subject, and analyzing the binding of the sample to determine the JAK2 genotype in the subject. In the case of a nucleic acid hybridization, binding with a capture probe at an address of the plurality, can be detected by any method known in the art, e.g., by detection of a signal generated from a label attached to the nucleic acid.

EXAMPLES

The invention is further described in the following examples, which do not limit the scope of the invention described in the claims.

Example 1

Increased Neutrophil Extracellular Trap Formation Promotes Thrombosis in Myeloproliferative Neoplasms An increased white blood cell count has been associated with an increased risk of thrombosis in MPN (4-9), and neutrophils from patients with MPNs display a number of features of enhanced activation (3, 10-13).

On stimulation, normal neutrophils can expel extracellular strands of decondensed DNA in complex with histones and other neutrophil granular proteins to produce neutrophil extracellular traps (NETs) (14). These structures have the ability to ensnare microorganisms and have also been implicated in the pathogenesis of autoimmunity and thrombosis (15, 16). We examined whether NET formation may be implicated in the enhanced thrombotic tendency seen in MPNs.

Materials and Methods

The following materials and methods were used in this Example.

Study Design

The aim of this study was to assess whether neutrophils harboring a $JAK2^{V617F}$ mutation had an increased propensity to form neutrophil extracellular traps and whether this was linked to an increased incidence of venous thrombosis. In addition, we sought to assess whether NETosis and subsequent thrombosis could be abrogated using clinically available inhibitors of JAK-STAT signaling.

We performed ex vivo assessment of mouse and human neutrophils with either JAK2$^{WT}$ or JAK2$^{V617F}$ with and without ruxolitinib treatment. NET formation was quantified before and after neutrophil stimulation using DAPI to detect morphological changes and immunofluorescence (IF) to detect citrullinated histone 3) (H3$^{cit}$) expression in the cells. Two different in vivo models of thrombosis (partial ligation and full ligation of the mouse IVC) were used to assess rates of thrombosis (at 4 hours unless otherwise stated) in both Jak2$^{WT}$ and Jak2$^{V617F}$ background. The impact of treatment with either ruxolitinib or DNase on the rate of thrombosis and on the composition of thrombi was also assessed in the partial ligation (NET dependent) model. A potential role for PAD4, a protein required for NETosis, was assessed in patient samples and in a Jak2$^{V617F}$/Pad4 null mouse model. Finally, we assessed the incidence of significant venous thrombosis in individuals without a known myeloid disorder with JAK2$^{V617F}$ clonal hematopoiesis.

In all studies mice were randomly assigned between control and treatment groups. The assessment and quantification of immunohistochemistry and IF staining were performed blinded to the genetic and treatment conditions. Experiments were done in triplicates. Sample sizes were based on previous studies assessing thrombosis rates between genetic/treatment groups using the same thrombosis models (36). No outliers were excluded.

Human Blood Samples.

Blood was drawn from patients with myeloproliferative neoplasms (MPNs) and myelodysplastic syndromes (MDS) who were seen at the Dana-Farber Cancer Institute and from age-matched normal controls. Whole blood was collected into ethylenediaminetetraacetic acid (EDTA)-coated tubes. Patients and controls were excluded if they had conditions that are known or suspected to affect NET formation such as active infection, active cancer (37), history of an autoimmune disease (38), treatment with immunosuppressive or anti-inflammatory drugs or history of diabetes (29). In addition, patients with recent history of infection, trauma or surgery (3 months before blood draw) were excluded. Therapy with acetylsalicylic acid (aspirin), hydroxyurea or anagrelide was allowed. All patients and controls gave their written consent and all blood samples were acquired according to protocols approved by the Dana-Farber Cancer Institute and Brigham and Women's Hospital Institutional Review Board.

Human Neutrophil Isolation and NET Formation Assay.

Neutrophil isolation and NET formation were carried out as previously described (39). Briefly, blood was drawn from patients and normal controls into EDTA-coated tubes and was processed within 3 hours. Red blood cells were first sedimented with Hetastarch (6% hydroxyethyl starch, HES) in 0.9% NaCl solution at 1:4 v/v dilution at 37° C. and then was re-suspended in RPMI1640 (Corning) supplemented with 2% fetal bovine serum (FBS, Omega Scientific). The supernatant was harvested and neutrophils were isolated using Percoll Plus (GE Healthcare) as previously described (39). Purity of cells was >95% as determined by Wright-Giemsa staining (FIG. 5B). For the screening NET assay, NET-bound neutrophil elastase was quantified using an available commercial kit according to manufacturer's instructions (Cayman chemical). For the validation immunofluorescence assay, neutrophils were resuspended in 2% heat-inactivated FBS and plated at 15,000 cells per well in 96-well optical-bottom plates in triplicates (Nunc MicroWell 96-Well Optical-Bottom Plates, ThermoFisher Scientific). Cells were then stimulated with ionomycin at 4 µM (Sigma-Aldrich) or PMA at 10 and 100nM (Sigma-Aldrich) for 2.5 hours. Cells were then instantly fixed in 2% paraformaldehyde (PFA) and stained as described below.

Mouse Neutrophil Isolation and NET Formation Assay.

We used a previously published VavCre/Jak2$^{V617F}$ murine model that results in constitutive heterozygous expression of the Jak2$^{V617F}$ activating mutation (18). Peripheral blood was collected from 10 to 12-week-old mice via the retroorbital venous plexus and was processed within 2 hours. Red blood cells were first sedimented with Hetastarch (6% hydroxyethyl starch, HES) in 0.9% NaCl solution at 1:4 v/v dilution at 37° C. Next, supernatant was collected and subjected to brief hypotonic lysis with sterile water. Neutrophils were isolated by negative selection with magnetic beads according to manufacturer's instructions (Neutrophil Isolation Kit, mouse, Miltenyi Biotec) and resuspended in 2% heat-inactivated FBS. Purity of cells was >95% as determined by Wright-Giemsa staining (FIG. 5B). Neutrophils were plated at 10-15,000 cells per well in 96-well optical-bottom plates in triplicates (Nunc MicroWell 96-Well Optical-Bottom Plates, ThermoFisher Scientific). Cells were then stimulated with ionomycin 4 µM (Sigma-Aldrich) or PMA 10 and 100 nM (Sigma-Aldrich) for 2.5 hours. Cells were then instantly fixed in 2% PFA and stained as described below.

Immunostaining, Fluorescence Microscopy and NET Quantification.

Fixed cells were processed as detailed above. Immunostaining, fluorescence microscopy and NET quantification procedures were similar for human and mouse specimens. Samples were washed with PBS and permeabilized (0.1% Triton X-100, 0.1% sodium citrate) for 10 min at 4° C. Samples were blocked with 3% BSA for 90 min at 37° C., rinsed, and then incubated overnight at 4° C. or for 1 hour at 37° C. in antibody dilution buffer containing 0.3% BSA, 0.1% Tween-20, and either rabbit antihistone H3 (citrulline 2, 8, 17) (0.3 µg/mL, ab5103; Abcam), rat anti-CD41 [MWReg30 clone (recognizes integrin alpha2b), Biolegend catalog number 133901] or rat anti-Ly6G (0.5 µg/mL, clone 1A8; Biolegend). After 3 washes, samples were incubated for 2 hours at room temperature in antibody dilution buffer containing Alexa Fluor-conjugated secondary antibodies in 0.3% BSA in PBS: goat anti-rat IgG (Alexa555, 2 µg/mL) or donkey anti-rabbit IgG (Alexa488, 1.5 µg/mL). DNA was counterstained with 1 µg/mL DAPI, and slides were coverslipped with Fluoromount gel (Electron Microscopy Sciences).

Images were acquired on an Axiovert 200M wide-field fluorescence microscope (Zeiss) coupled to an AxioCam MR3 monochromatic CCD camera (Zeiss) using a Zeiss Plan-Neofluar 20×/0.4 Con Ph2 objective lens with the Zeiss AxioVision software (version 4.6.3.0). Neutrophils positive for citrullinated histone H3 (H3$^{cit}$) were determined by thresholding analysis using ImageJ software (National Institutes of Health, USA).

Morphologic quantification of NETs was performed based on morphological criteria that included nuclear delobulation and swelling and/or observed extension of web-like DNA strands. Percentages of H3$^{cit}$ cells and NETs were determined from five or six non-overlapping fields per well and the average was taken from duplicates or triplicates for each condition in every experiment. Exposure time for H3$^{cit}$ and DNA were identical for all treatments within the same experiment.

Results are expressed as percent NETs of DAPI positive neutrophils. NET quantification was assessed independently by 2 investigators blinded to the results (OW and RS). Results obtained by the first investigator were independently verified by a second investigator blinded to the results obtained by the first investigator and to the conditions.

Organ Harvest and Staining.

Mice were sacrificed and injected immediately post-mortem via the trachea with a 50:50 mixture of 10% neutral buffered formalin and optimal cutting temperature (OCT) compound (Sakura Finetech). Lungs were then removed and preserved in 10% neutral buffered formalin solution for at least 24 hours before being processed for staining. Organs were embedded in paraffin, sectioned, rehydrated and stained at the pathology research core facility at Harvard Medical School in Boston, Mass.

Lung tissue to be used for immunofluorescence was prepared for harvest in a similar manner as above but was embedded in OTC and snap frozen immediately after harvest. 10-μm cryosections were then produced for staining. The Martius Scarlet Blue (MSB; trichrome) stains were performed on frozen sections fixed in Bouin's solution at 56° C. for 1 hour and stained with a MSB kit per manufacturer's instructions (Atom Scientific).

Immunofluorescence of Thrombus and Lung Cryosections

Sections were allowed to come to room temperature, before rinsing in PBS with 0.1% Tween 20 (PBST). Sections were blocked for 1 hour at room temperature with 10% FBS in PBST in a humidified chamber. Sections were incubated in the same chamber overnight at 4° C. with the primary antibodies described above against Ly6G and H3$^{cit}$ in 10% FBS in PBST. Slides were rinsed in PBST before incubating with the secondary antibody under the same conditions as used for the primary antibody (goat anti-rat Ig (IgG) (Alexa555, 1.5 μg/mL) or donkey anti-rabbit IgG (Alexa647, 1.5 μg/mL). After a further wash in PBST sections were stained with DAPI and mounted as described above. Sections were visualized using AxioImager D1 (Carl Zeiss Microscopy) and images taken using Axiocam MRc Camera (Carl Zeiss Microscopy). Zen software 2.3 (version 13) was used to analyze images. For the final images used in the figures, Alexa647 was represented using green.

Venous Stenosis Model.

After bone marrow harvest, c-Kit positive marrow cells were obtained from VavCre/Jak2$^{V617F}$ KI mice using CD117 Microbeads according to manufacturer's instructions (Miltenyi Bitotec). After being resuspended in Hank's Balanced Salt Solution (Life Tehnologies) were injected into sub-lethally irradiated wild type (WT) recipients (8-week old female CD45.1-positive B6.SJL (Jackson Laboratory) recipients; 350,000 per animal) resulting in constitutive heterozygous expression of the mutation in hematopoietic cells only. Successful engraftment was checked using donor chimerism as assessed by relative abundance of either CD45.1-PE clone A20 or CD45.2-FITC clone 104 (eBioscience) expressing hematopoietic cells and a phenotype reminiscent of PV was documented (FIG. 6A-B).

Mice were anesthetized with 3.5%, isoflurane and isoflurane was maintained at 2% in 100% oxygen. A midline laparotomy was performed, and the inferior vena cava was exposed. Any side branches between the renal and iliac veins were ligated with 7/0 polypropylene suture. A 30-G spacer was placed parallel to the inferior vena cava, and 7/0 polypropylene suture was used to partially ligate the inferior vena cava (IVC) to ~10% of its original diameter. The spacer was removed, and the mouse was sutured and allowed to recover. In the full ligation model, side branches were ligated as before. In addition, posterior branches were cauterized before the IVC was fully ligated with 7/0 polypropylene suture. At the designated post-ligation time points (2 and 4 hours), mice were anesthetized with isoflurane and blood was collected via the retroorbital sinus plexus. After the mice were sacrificed the IVC was exposed to allow for collection of the thrombi formed within the IVC. Thrombi were embedded in OCT and snap frozen for cryosectioning. All mice were given buprenorphine (0.03 μg/mL, vol/vol) (0.1 mg/kg) s.c. as an analgesic immediately before surgery.

Pad4 Null Jak2$^{V617F}$ Model.

The previously published Jak2 $^{V617F}$ MSCV-IRES-GFP vector (27) was used to generate ecotropic retrovirus using packaging plasmid (Ecopak), TransIT-LT1 Transfection Reagent (Mirus Bio LLC), and the human embryonic kidney-cell line 293T using standard methods. Briefly, 293T cells were cultured in Dulbecco's Modified Eagle's Medium (DMEM, Corning) supplemented with 10% FBS and 1% Penicillin/Streptomycin/Glutamine (PSG, Life Technologies). A total of 1.5 million cells were plated on a 10 cm plate. When cells were at 60-80% confluency, a transfection cocktail of 1 ml reduced serum medium (Opti_MEM, Life Technologies), 45 μl TransIT-LT1 Transfection Reagent, 10 μg of MSCV-IRES-GFP vector, and 10 μg of Ecopak vector, was added to the plate. Media containing the transfection mixture was removed after 12 hours. Fresh DMEM with 10% FBS and 1% PSG was added. After 36 hours the media (containing retrovirus) was harvested and filtered (22 μM). Bone marrow from Pad4 null mice and Pad4 wild type controls was harvested and c-Kit cell isolated using CD117 Microbeads as described above. Cells were cultured in Serum-Free Expansion Medium (StemSpan SFEM, Stem Cell Technologies) with 50 ng/ml recombinant murine thrombopoietin (TPO, PeproTech) 50 ng/ml recombinant murine stem cell factor (SCF, PeproTech), and 1% PSG for 48 hours. Cells were then transduced with fresh retrovirus using RetroNectin (Takara Bio Inc.) according to the manufacturer's instructions. After 24 hours, cells were resuspended in HBSS before transplantation of 350,000 cells by retro orbital injection into lethally irradiated 8-week old female CD45.1-positive B6.SJL (Jackson Laboratory) recipients. At 8 weeks post-transplant, expression of viral construct was confirmed by assessing GFP using BD FACSCanto II (BD Biosciences) and hematocrit assessed in animals following retroorbital bleed. The lungs from mice in the context of either Pad4$^{-/-}$ or Pad4$^{+/+}$ were harvested and processed for IHC and IF as described above.

Western Blot Analysis.

After collection of human neutrophils, the samples were snap frozen and homogenized in RIPA buffer supplemented with protease inhibitor cocktails (Sigma) on ice. After centrifugation at 20,000 g for 20 min at 4° C., equal amount of protein per sample were resolved on Criterion 4-15% Tris-HCl gels (BioRad) and electroblotted on Immobilon-P PVDF membranes (Merck Millipore), which were then incubated with primary antibodies (rabbit polyclonal anti-H3Cit, 1:1,000, Abcam, cat. no. ab5103; mouse monoclonal anti-human PAD4, 1:1,000, Abcam, cat. no. ab128086) at 4° C. overnight and subsequently with appropriate HRP-conjugated secondary antibodies [1:15,000, donkey anti-rabbit IgG (H+L)-HRP conjugate (GE Healthcare)] for 1 hour at room temperature. The blots were developed with Super-Signal West Dura Extended Duration Substrate enhanced chemiluminescence substrate (Thermo Scientific). Equal loading was confirmed using an HRP conjugated monoclonal antibody against human β-actin (mAbcam 8226).

Treatment with Ruxolitinib.

For ex-vivo experiments ruxolitinib (Selleckchem) was used at a concentration of 300 nM for 150 min. For in-vivo experiments mice were gavaged with 90 mg/kg of ruxolitinib or vehicle (5% Dimethylacetamide, DMAC, Sigma-Aldrich) twice daily for 3 days (6 doses) as previously described (40). For the ex-vivo NET inhibition assay we used a PAD4 inhibitor (GSK 484 at 10 µM) as a negative control (Cayman chemical).

Treatment with DNase.

DNase 1 (Pulmozyme, Genentech) was diluted in sterile saline and injected immediately after surgery (50 µg intraperitoneally and 10 µg intravenously via tail vein). Control mice were injected with the DNAase vehicle buffer (8.77 mg/mL sodium chloride and 0.15 mg/mL calcium chloride) diluted in sterile saline. Mice were assessed for thrombosis at 4 hours.

Analysis of Mouse Plasma.

Plasma dsDNA was analyzed using the Quant-iT Picogreen assay (Invitrogen) according to manufacturer's instructions.

Platelet and Neutrophil Functions.

Mouse blood was collected in tubes containing 0.2 µg/mL enoxaparin (Sanofi-Aventis). Platelet-rich plasma (PRP) was collected after two centrifugation steps at 300×g for 7 min at RT. ADP-induced aggregation was monitored in PRP, whereas responses after stimulation with thrombin or collagen were analyzed in washed platelet suspensions. For this, PRP was pelleted at 700×g in the presence of prostacyclin ($PGI_2$) (0.1 µg/mL) and apyrase (0.02 U/mL). Platelet pellets were washed twice in modified Tyrode-HEPES buffer (134 mM NaCl, 0.34 mM $Na_2HPO_4$, 2.9 mM KCl, 12 mM $NaHCO_3$, 5 mM HEPES, 1 mM $MgCl_2$, 5 mM glucose, 0.35% BSA, pH 7.4) containing $PGI_2$ and apyrase. Platelet suspensions (150 µL with $5\times10^5$ platelets/µL) in Tyrode-HEPES buffer containing 2 mM $CaCl_2$ were stimulated with the indicated agonists and light transmission was recorded on a Chronolog platelet aggregometer.

For the assessment of CD11b induction, whole blood from $Jak2^{WT}$ or $Jak2^{V617F}$ mice that had been treated for 72 hours with either ruxolitinib or vehicle was processed as above to isolate neutrophils. After 20 minutes of stimulation with 4 µM ionomycin, neutrophils were stained with anti-mouse Ly6G APC antibody clone 1A8 (BioLegend) and anti-mouse CD11b FITC clone M1/70 (Invitrogen) and analyzed by flow cytometry (BD FACSCanto II). CD11 b expression was quantified as the MFI of FITC in LyG-positive single cells. Reactive oxygen species were quantified after 20 minutes of stimulation with 4 µM, ionomycin, before staining with DHR dihydrorhodamine-123 (Invitrogen) and anti-mouse Ly6G APC antibody clone 1A8 (BioLegend) at 4° C. on ice. ROS concentrations were determined as the MFI of FITC for Ly6-positive single cells.

Case-Control Cohort.

Schizophrenic patients and controls from a case-control cohort were assessed, to including only patients with both molecular and clinical data. Clinical data were assessed using the ICD10 codes for different categories of major venous thrombosis and for myeloid disease including MPN, MDS, and AML. ICD10 codes and the corresponding diagnosis are shown in Table D. Individuals were regarded as being in one of two clinical groups; ever or never having had a venous thrombosis. Because previous data from this cohort suggested an effect of smoking on increased vascular events, and there were higher rates of smoking in the cohort of patients with schizophrenia, the schizophrenic patients and control cases were also assessed separately. Whole-exome sequencing, and the identification of mutations and their variant allele frequency, has been described previously (31).

TABLE D

| ICD-10 codes used to identify thrombosis in the case-control cohort | | |
|---|---|---|
| ICD10 Main Code | Sub-code | Diagnosis |
| I81 | | Portal vein thrombosis |
| I82 | | Acute and chronic embolism/thrombosis of veins |
| K64 | | Perianal vein thrombosis |
| N48 | | Thrombosis of superficial vein of the penis |
| I80 | | Phlebitis/thrombophlebitis |
| K75 | | Portal vein phlebitis |
| K55 | | Mesenteric vein thrombosis |
| G95 | G95.1 | Intraspinal thrombosis |
| I27 | I27.82 | Chronic PE |
| Z86 | Z86.711 | Personal history of PE |
| Z86 | Z86.718 | Personal history of other thrombosis |
| D46 | | Myelodysplasia |
| D45 | | Polycythemia |
| D47 | D47.1 | Myelofibrosis |
| D47 | D47.3 | Essential thrombocythemia |
| C92 | | Myeloid leukemia |

Statistics.

Data are presented as means ±SEM unless otherwise noted and were analyzed using a two-tailed Mann-Whitney U test. For murine data, thrombus frequencies were analyzed using Fisher's exact test. For human population data differences in thrombosis incidence were assessed using Fisher's exact test with Bonferroni correction for testing of multiple hypotheses. Differences in age were assessed using Mann-Whitney U test. All analyses were performed using GraphPad Prism software (Version 5.0). Results were considered significant at p<0.05. Nominal p-values were used unless otherwise specified.

Figure 1A:
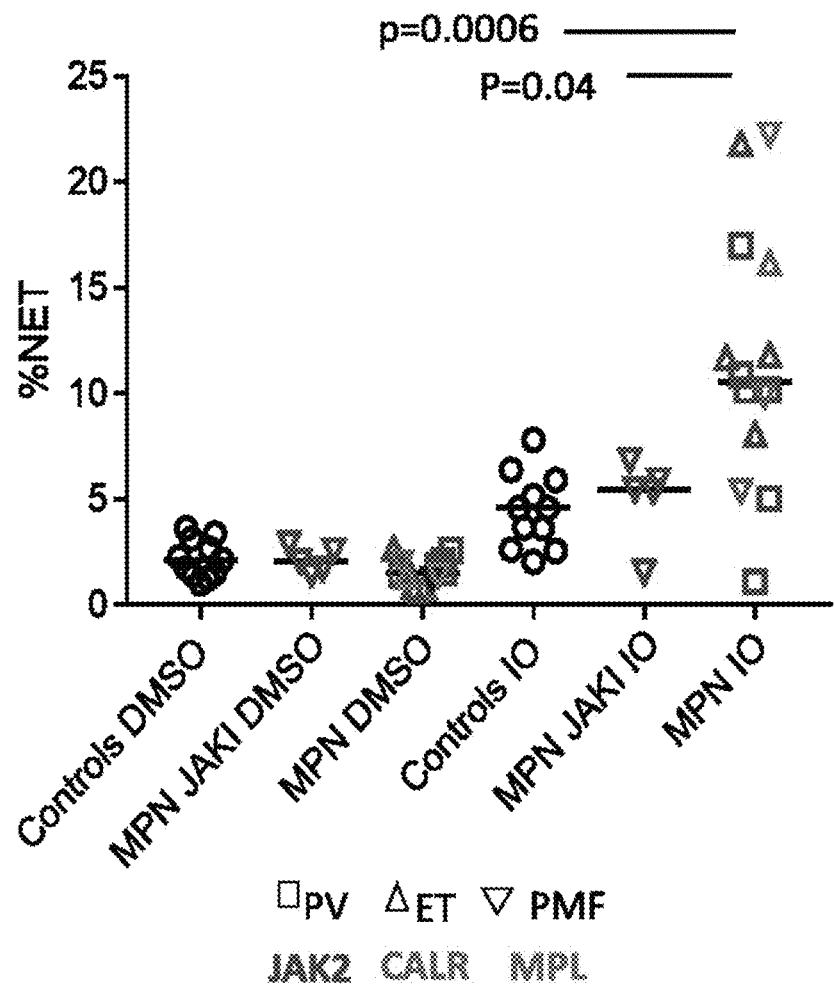
FIGS. 1A-I: Neutrophils derived from patients with MPNs are associated with an increase in NET formation and a prothrombotic, NET-rich phenotype (A) NET formation in patients with myeloproliferative neoplasms (MPN) (receiving a JAK inhibitor n=5, receiving other therapy n=14) compared to healthy controls (n=11) when stimulated with 4 μM ionomycin (IO) or DMSO for 2 hours. Patients receiving a JAK inhibitor are indicated by JAKI. Individual values and median (B) Representative immunofluorescence images of human neutrophils after simulation with 4 μM IO or DMSO for 2 hours. DAPI in blue and citrullinated histone H3 ($H3^{cit}$) in green. Scale bar=50 μm. (C) The percentages of human neutrophils with evidence of NET formation after stimulation with PMA (10 nM) with and without ruxolitinib pre-treatment (n=4). Neutrophils are derived from controls. (D)
Figure 1B:
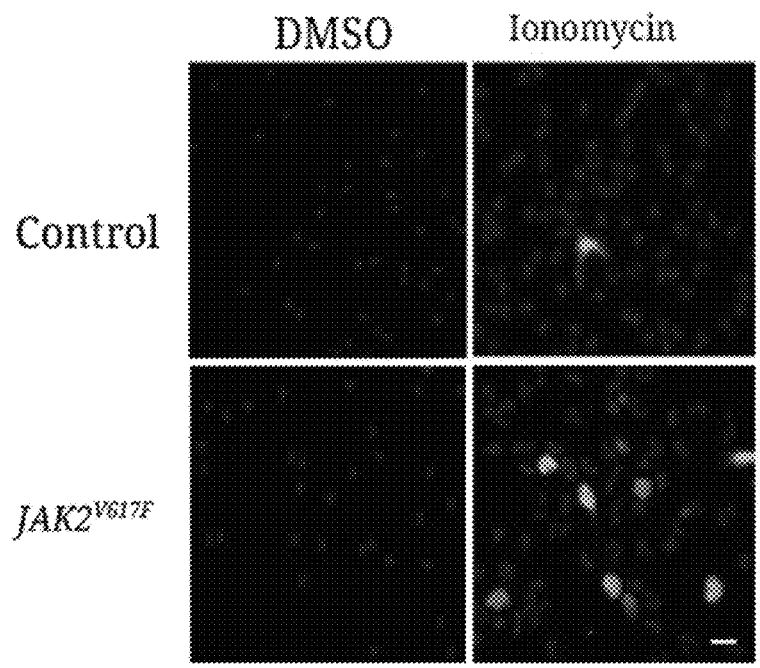
Figure 1C:
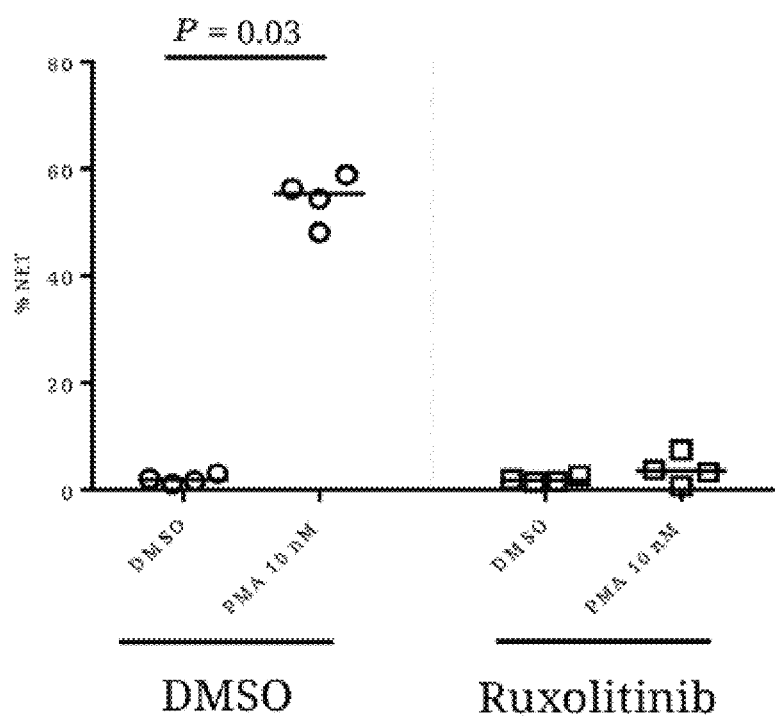
Figure 1D:
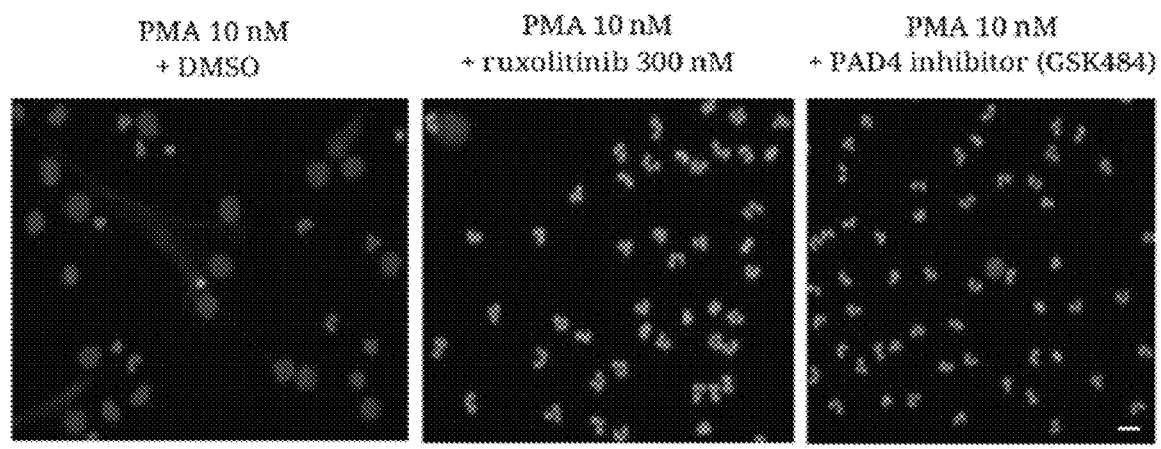
Figure 5A:
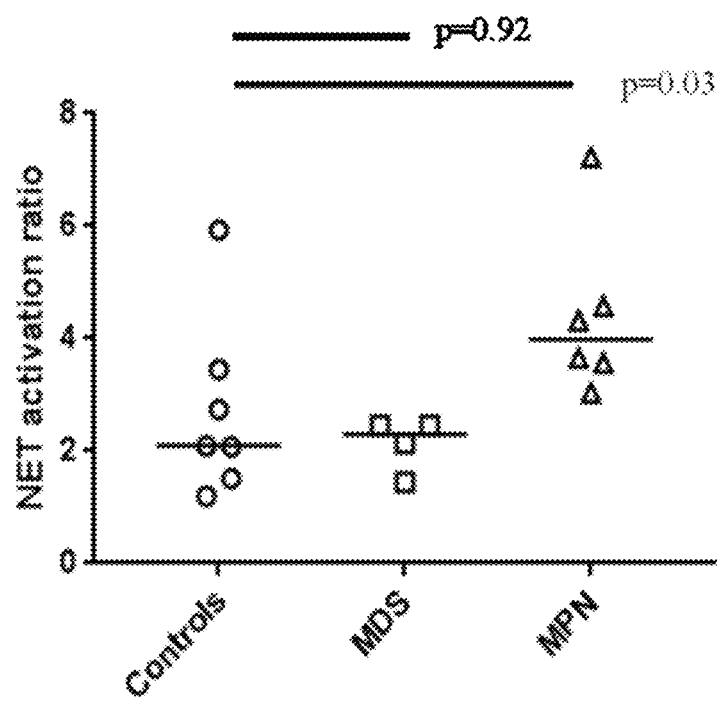
Figure 5B:
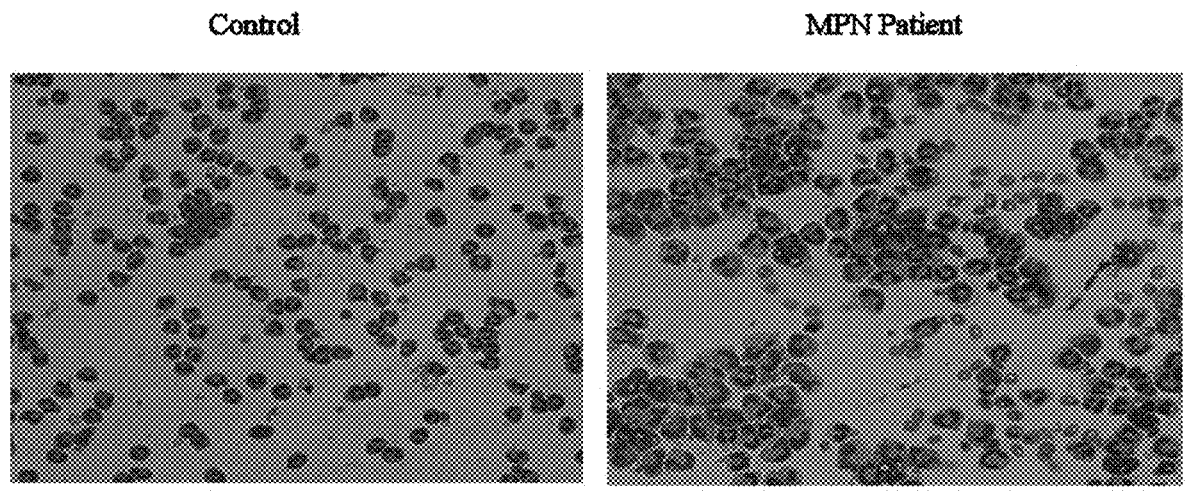
Figure 5C:
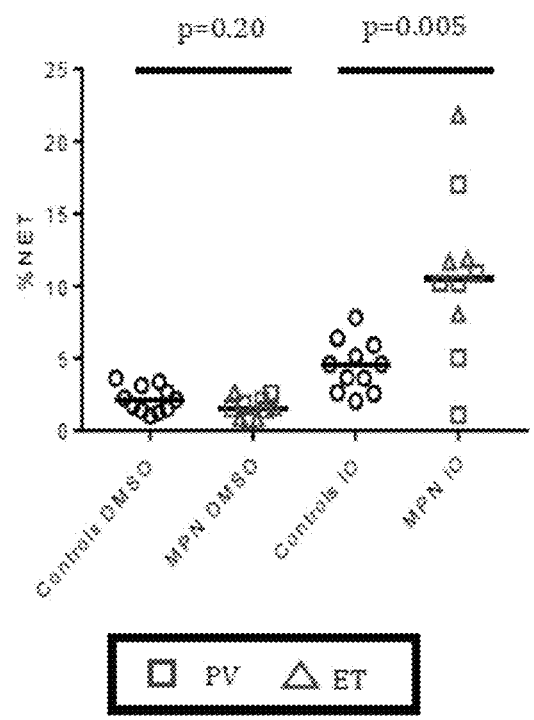
Figure 5D:
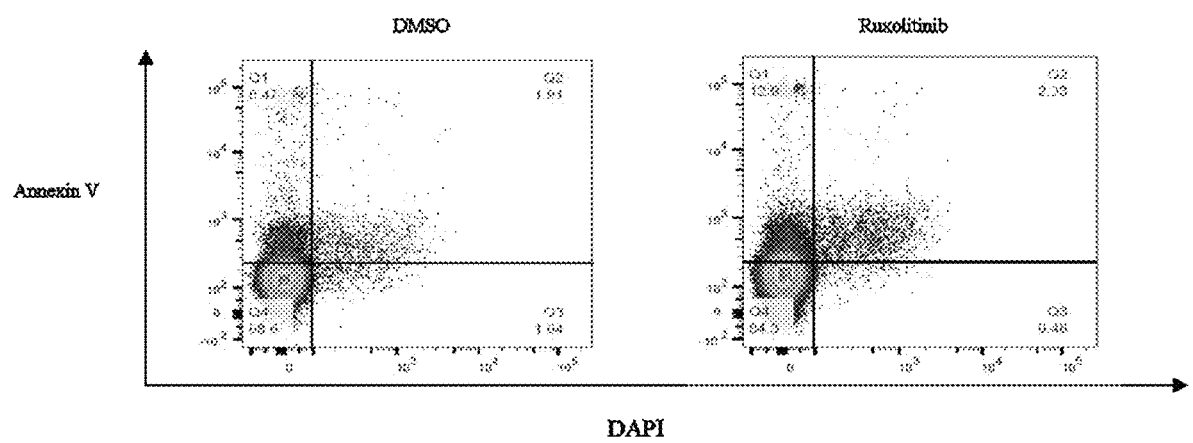

Neutrophils Derived From Patients with MPNs are Associated with an Increase In NET Formation that is Blunted by Ruxolitinib We observed an increase in NET formation in neutrophils from patients with MPNs compared to those from patients with myelodysplastic syndrome (MDS) as well as age-matched controls in an unbiased screen assessing various neutrophil functions including chemotaxis, phagocytosis and oxidative burst (FIGS. 5A and 5B). To further investigate this finding, we quantified NET formation in a larger cohort of MPN patients and controls. We stimulated isolated neutrophils with ionomycin, a calcium ionophore. NET formation was assessed quantitatively in neutrophils by identifying typical morphological changes and citrullinated histone 3 ($H3^{cit}$) expression, which is an established and widely used marker of NET formation, as described previously (17). Stimulated neutrophils from patients with MPNs, including those with $JAK2^{V617F}$, had a significant increase in NET formation (p=0.0006; FIGS. 1A and 1B, FIG. 5C; Tables A-C). Patients receiving a JAK1/2 inhibitor had reduced NET formation, similar to that of healthy controls (FIG. 1A). Similarly, NET formation was decreased in normal neutrophils incubated in vitro with ruxolitinib (FIGS. 1C and 1D). Due to limited patient numbers receiving hydroxyurea, and no patients receiving interferon, the effects of these therapies on NET formation could not be assessed.

TABLE A

Patient characteristics (not treated with JAK-inhibitors)

| UPN | Age/gender | Diagnosis | Thrombosis risk | WBC (×10⁹/L) | Therapy | Mutation* | Allele burden | % NET formation |
|---|---|---|---|---|---|---|---|---|
| 11 | 20/M | PV | Low | 12 | ASA | JAK2 V617F | 32% | 17% |
| 18 | 49/F | PV | Low | 16.34 | ASA | JAK2 V617F SF3B1 K666N | 44% 18% | 10.8% |
| 46 | 60/F | PV | High | 53.68 | ASA Hydrea | JAK2 V617F | 97% | 11.7% |
| 55 | 46/M | PV | Low | 15.2 | ASA | JAK2 V617F | 70% | 10.2% |
| 63 | 63/F | PV | High | 13.98 | ASA Hydrea | JAK2 V617F DMMT3A R729Q TET2 Q916* | 50% 50% 50% | 10.2% |
| 74 | 51/F | PV | Low | 19.17 | ASA | JAK2 V617F TET2 Q749fs* | 79% 54% | 1.1% |
| 75 | 68/M | PV/MF | High | 44 | ASA | JAK2 V617F | 48% | 5% |
| 45 | 57/F | ET | Low | 6.98 | ASA | MPL W515K | 34% | 16.2% |
| 69 | 29/F | ET | Low | 18.01 | ASA | JAK2 V617F | NA | 11.8% |
| 76 | 68/F | ET | High | 8.37 | ASA Hydrea | JAK2 V617F | NA | 21.8% |
| 85 | 68/F | ET | High | 9.31 | ASA Hydrea | JAK2 V617F | NA | 8.1% |
| 5 | 47/F | PMF | NA | 5.99 | ASA EPO | CALR | 49% | 9.9% |
| 23 | 65/F | PMF | NA | 15.69 | ASA | CALR ASXL1 R693fs* ASXL1 p753fs* | 47% 19% 14% | 5.4% |
| 29 | 47/F | PMF | NA | 21.78 | ASA EPO | MPL W515K | 44% | 22.3% |

*Data shown based on clinically available molecular studies performed

TABLE B

Patient characteristics (JAK inhibitor-treated)

| UPN | Age/gender | Diagnosis | Thrombosis risk | WBC (×10⁹/L) | Therapy | Mutation* | Allele burden | % NET formation |
|---|---|---|---|---|---|---|---|---|
| 78 | 58/M | PMF | NA | 6.18 | NS-018 | JAK2 V617F CBL Y371N U2AF1 S34Y | 42% 5% 18% | 6.9% |
| 68 | 83/M | PV | NA | 48.55 | ASA Ruxolitinib | JAK2 V617F TET2 N1000fs* TET2 R1261H TP53 G245D TP53 H214R | 96% 48% 45% 4% 3% | 1.5% |
| 64 | 65/F | PMF | NA | 39.58 | Ruxolitinib Hydrea | JAK2 V617F | 99% | 5.9% |
| 82 | 54/M | PMF | NA | 13.77 | ASA Ruxolitinib | JAK2 V617F | NA | 5.4% |

TABLE B-continued

Patient characteristics (JAK inhibitor-treated)

| UPN | Age/gender | Diagnosis | Thrombosis risk | WBC (×10$^9$/L) | Therapy | Mutation* | Allele burden | % NET formation |
|---|---|---|---|---|---|---|---|---|
| 86 | 74/F | PMF | NA | 10.52 | Ruxolitinib | JAK2 V617F | 94% | 5.5% |
|  |  |  |  |  |  | ASXL1 E635fs* | 14% |  |
|  |  |  |  |  |  | ASXL1 R634fs* | 15% |  |
|  |  |  |  |  |  | SH2B3 E61fs* | 14% |  |

*Data shown based on clinically available molecular studies performed

TABLE C

Comparing NET formation between groups

| Conditions (respective N) | P value* |
|---|---|
| Controls vs. Pts (11, 14) | P = 0.001 |
| Controls vs. PV# (11, 5) | P = 0.064 |
| Controls vs. ET (11, 5) | P = 0.0005 |
| Controls vs. MF# (11, 3) | P = 0.04 |
| PV vs. ET# (5, 5) | P = 0.31 |
| PV vs. MF# (5, 3) | P = 0.99 |
| ET vs. MF# (5, 3) | P = 0.79 |
| Male vs. female (3, 11) | P = 0.77 |
| Over 60 yearsold vs. under 60 years old (6, 8) | P = 0.36 |
| High-risk features vs. non-high-risk features$ (5, 6) | P = 0.70 |
| WBC over 15 × 10$^9$/L vs. less than 15 × 10$^9$/L (7, 7) | P = 0.80 |
| PLT over 400 × 10$^9$/L vs. less than 400 × 10$^9$/L (3, 11) | P = 0.99 |
| HCT over 45% vs. less than 45% (5, 9) | P = 0.44 |
| aHydroxyurea treated vs. non-Hydrea treated (5, 9) | P = 0.80 |
| JAK2 inhibition vs. none (5, 14) | P = 0.04 |
| JAK2 vs. CALR (10, 2) | P = 0.33 |
| JAK2 vs. MPL (10, 2) | P = 0.11 |
| MPL vs. CALR (2, 2) | P = 0.33 |
| JAK2 allele burden >50% vs. <50%& (3, 5) | P = 0.48 |

Figure 1E:
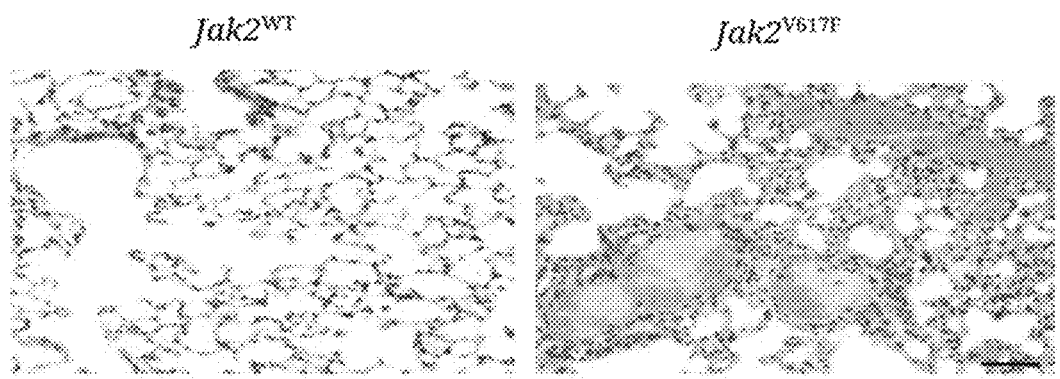
Figure 1F:
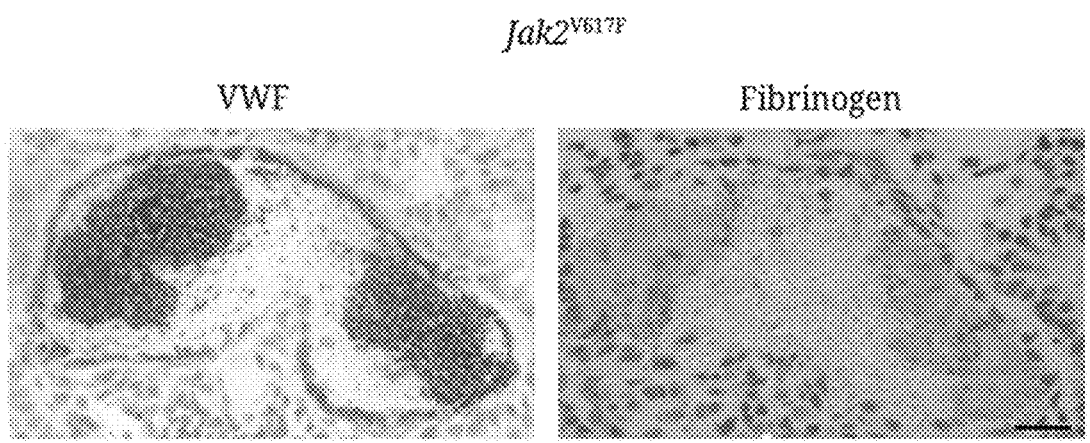
Figure 1G:
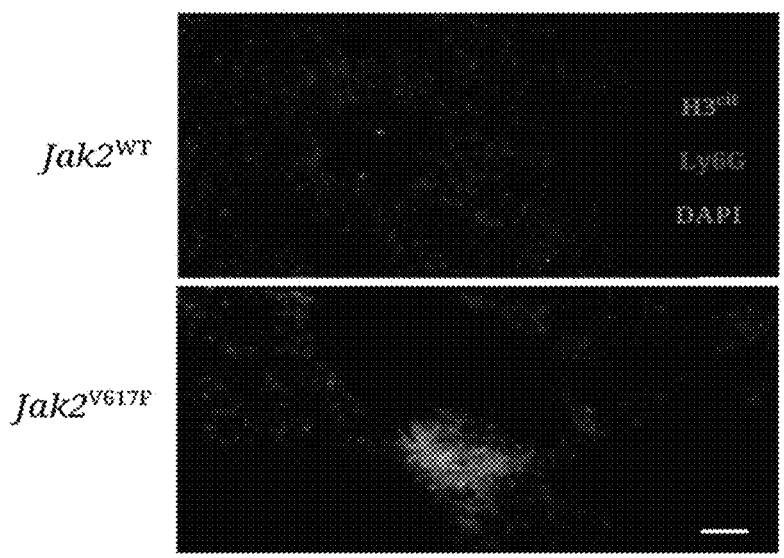

*Mann-Whitney test for non-parametric values
Excluding patient who had features of PV transforming to MF (UPN 75)
$High-risk for thrombosis defined as age > 60 and/or prior thrombosis; patients with available data analyzed
&Patients with available data analyzed Jak2$^{V617F}$-Driven MPN Mouse Models have a NET-Rich, Prothrombotic Phenotype To validate our findings from primary MPN samples in a genetically-controlled, in vivo experimental model, we used an established conditional knock-in murine model for the Jak2$^{V617F}$ allele (18). Jak2$^{V617F/WT}$; Vav-Cre mice, with to heterozygous expression of the Jak2$^{V617F}$ allele in hematopoietic cells (abbreviated as Jak2$^{V617F}$) develop an MPN phenotype reminiscent of human polycythemia vera (PV) and have a shortened lifespan (18). We first determined whether Jak2$^{V617F}$ mice develop spontaneous pulmonary thrombosis using immunohistochemical assessment of lung sections. We found increased thrombosis in Jak2$^{V617F}$ mice, whereas Jak2$^{WT}$ mice had no evidence of spontaneous thrombosis in the lungs (FIGS. 1E and 1F).

Figure 1H:
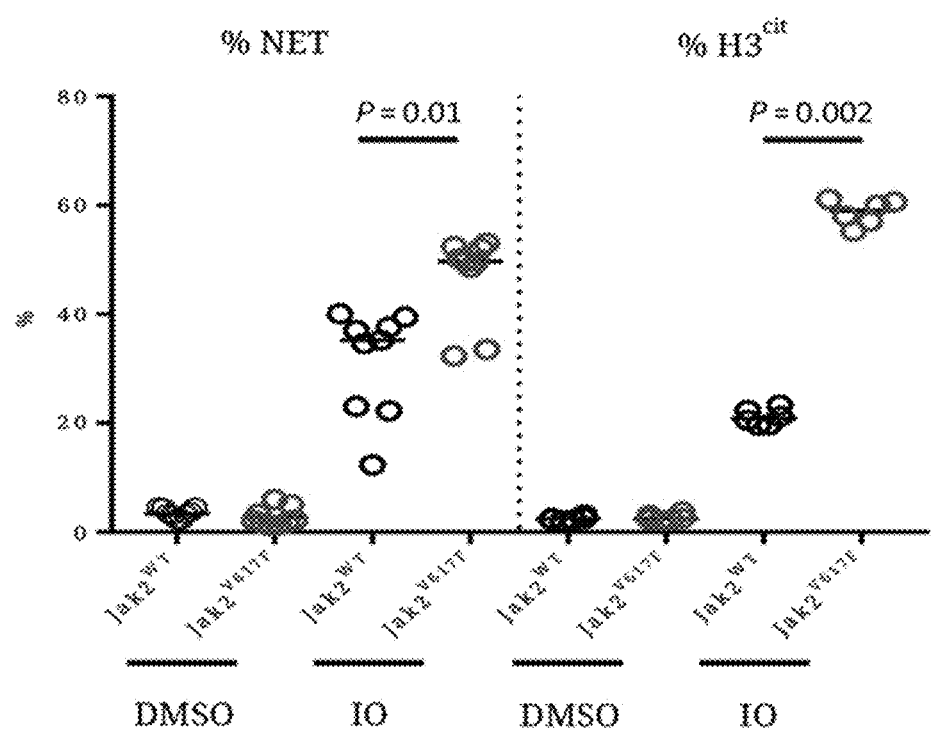
Figure 1I:
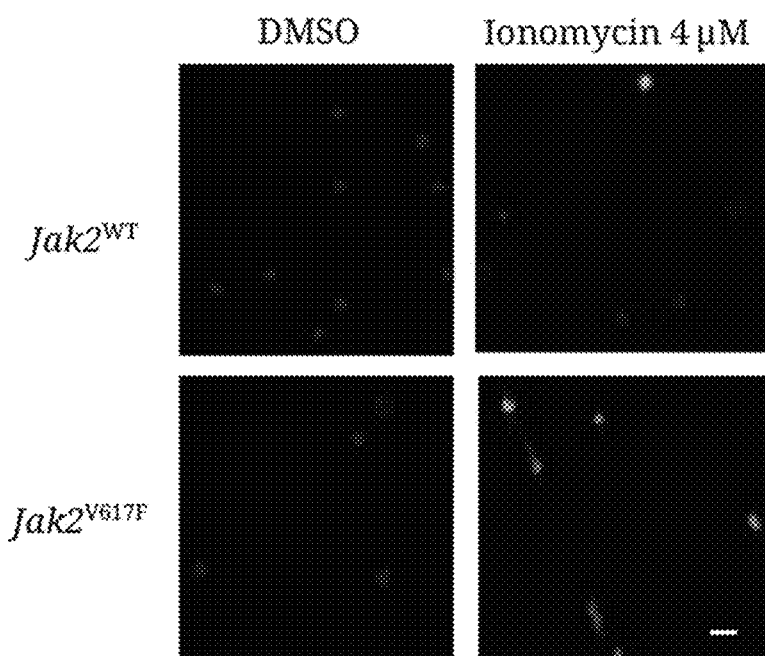

To determine whether the pathologic thrombosis was associated with NET formation, we used immunofluorescence (IF) to assess neutrophil infiltration and expression of citrullinated H3 (H3$^{cit}$), an established marker of NET formation. We found an increase in H3$^{cit}$ expression in the lungs of Jak2$^{V617F}$ mice (1G). Furthermore, neutrophils isolated from the peripheral blood of Jak2$^{V617F}$ mice had a significant increase in NET formation upon stimulation with ionomycin (p=0.01; FIGS. 1H and 1I).

Ruxolitinib Reduces the Rate of Induced Venous Thrombosis in Jak2$^{V617F}$-Driven MPN Mouse Models.

To interrogate the propensity for acute thrombosis in Jak2$^{V617F}$ mice, we assessed thrombosis after experimental stenosis of the inferior vena cava, an established model for determining predisposition to venous thrombosis that has previously been shown to be NET-dependent (19). To ensure that the observed effects were a result of cell-intrinsic properties of Jak2$^{V617F}$-expressing neutrophils, we isolated c-Kit positive cells from Jak2$^{V617F}$ mice and transplanted them into sub-lethally irradiated Jak2$^{WT}$ recipient mice. As expected, recipient mice developed a PV-like phenotype with high hematocrit (HCT) and enlarged spleens (FIG. 6A-B). Recipient mice were then treated for 72 hours with ruxolitinib or vehicle.

Figure 2A:
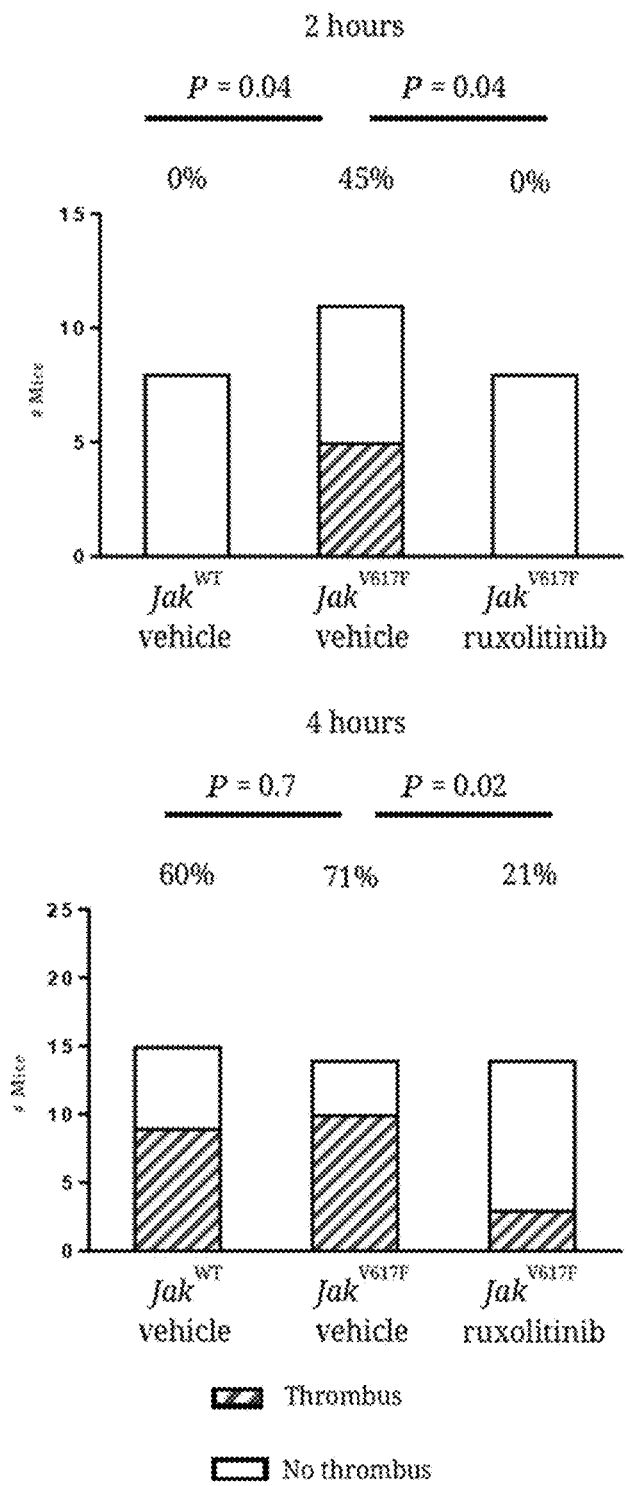
Figure 2B:
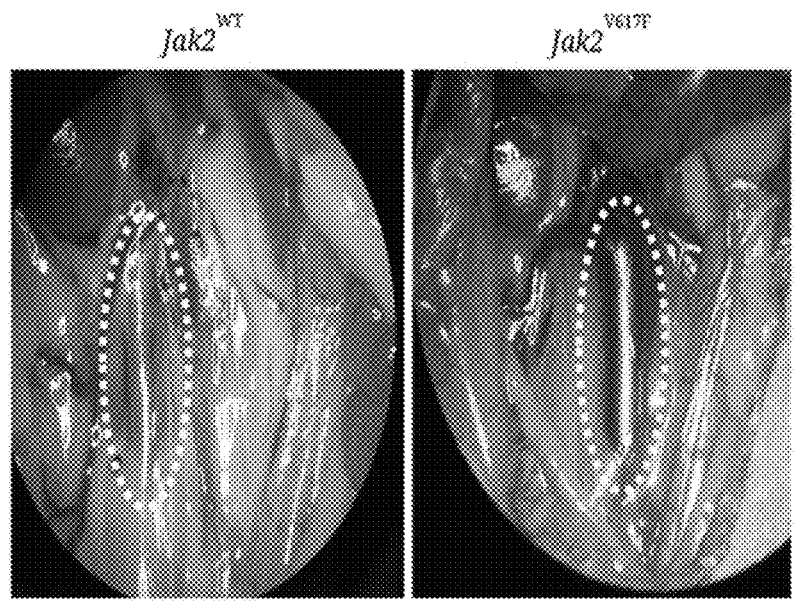
Figure 2C:
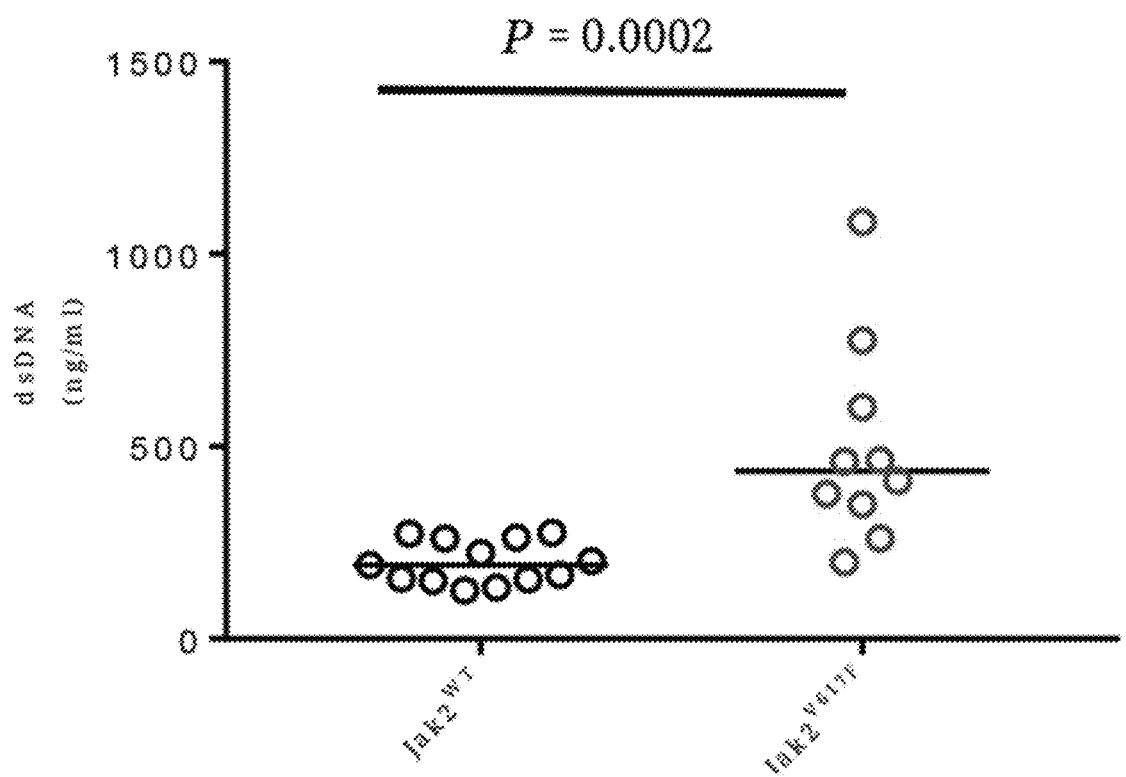
Figure 2D:
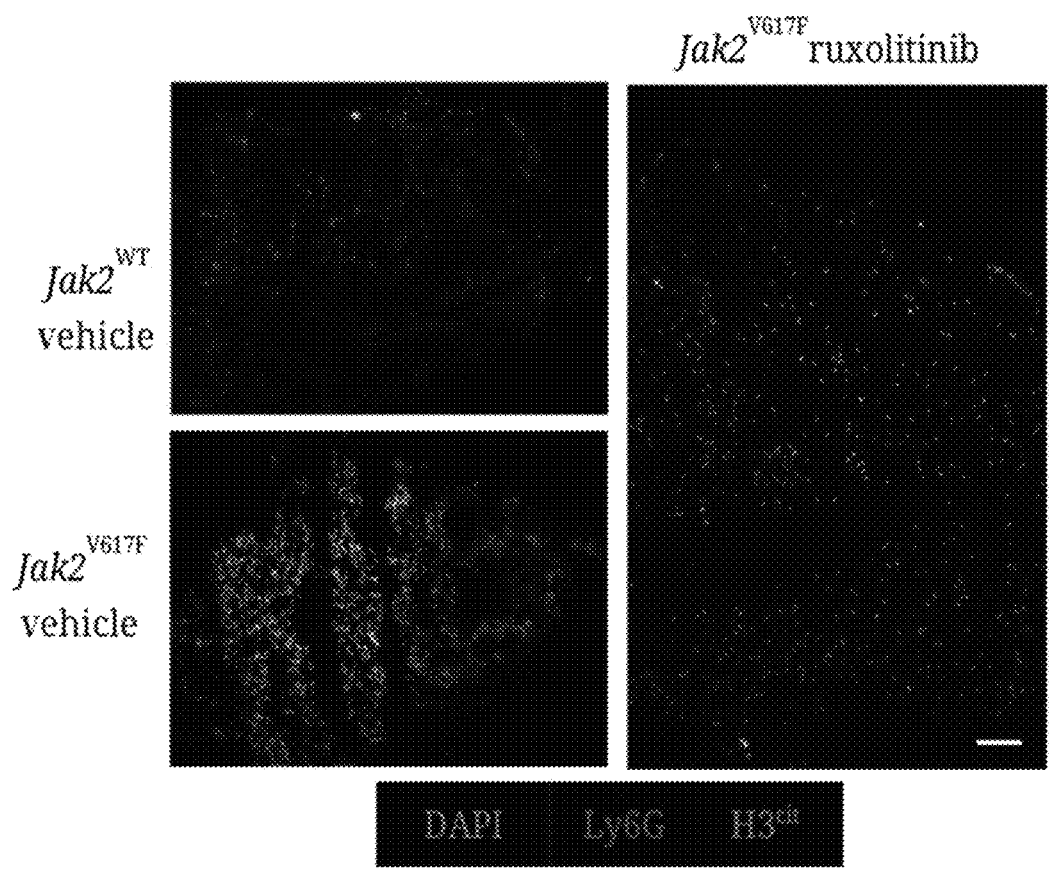
Figure 2E:
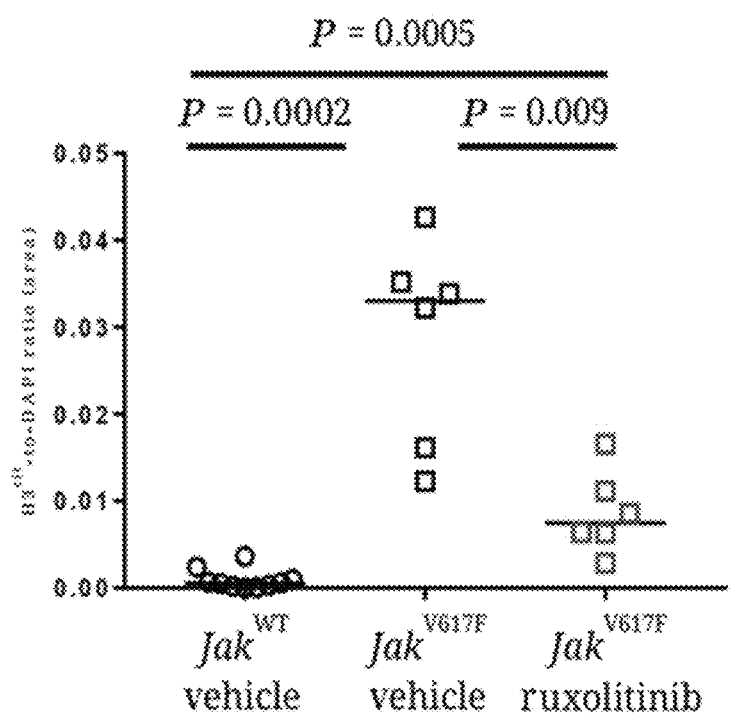
Figure 7A:
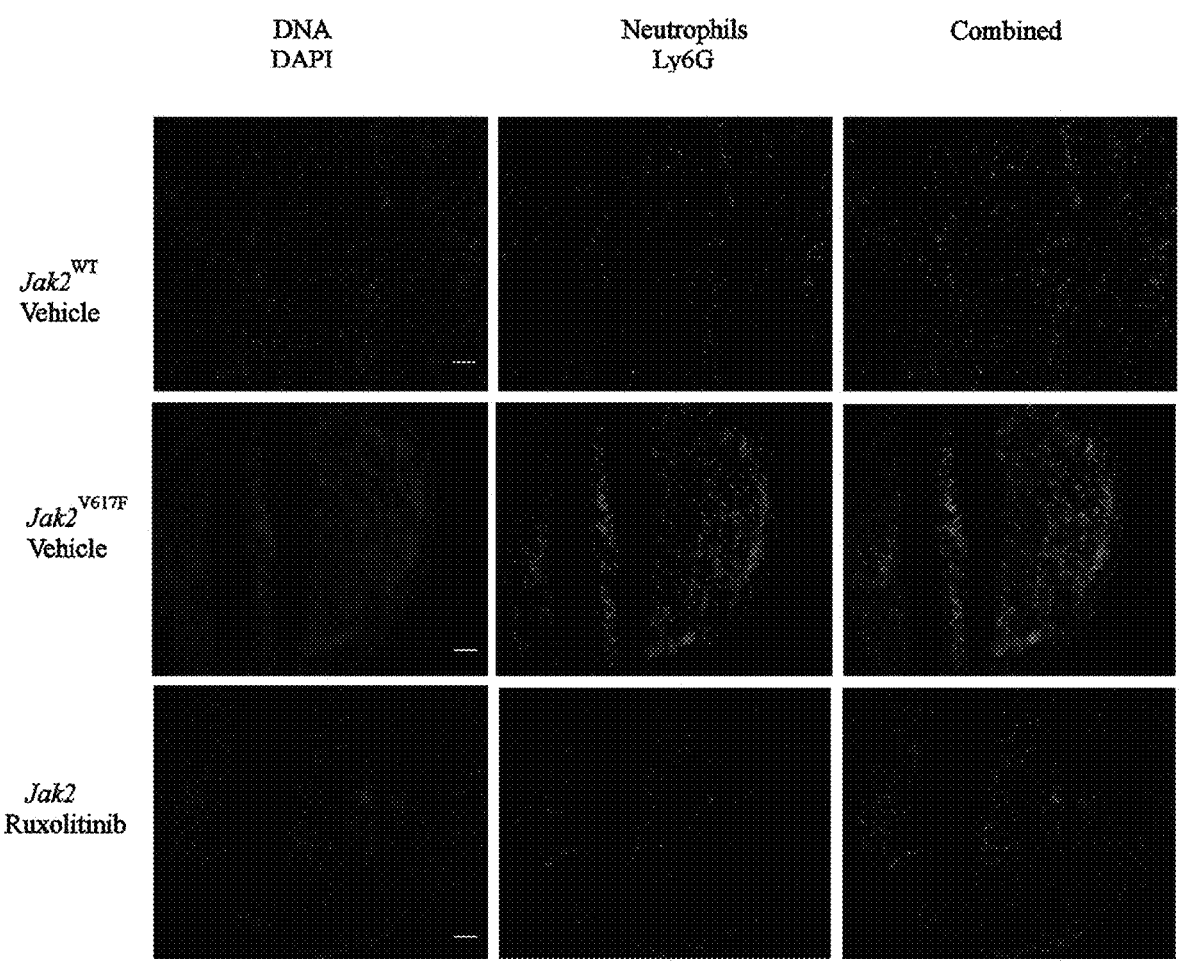
Figure 7B:
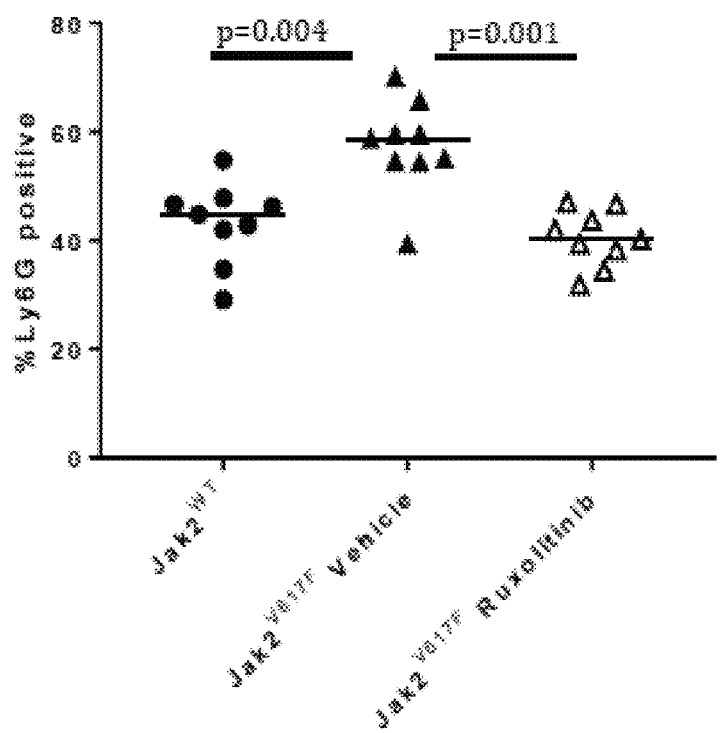
Figure 7C:
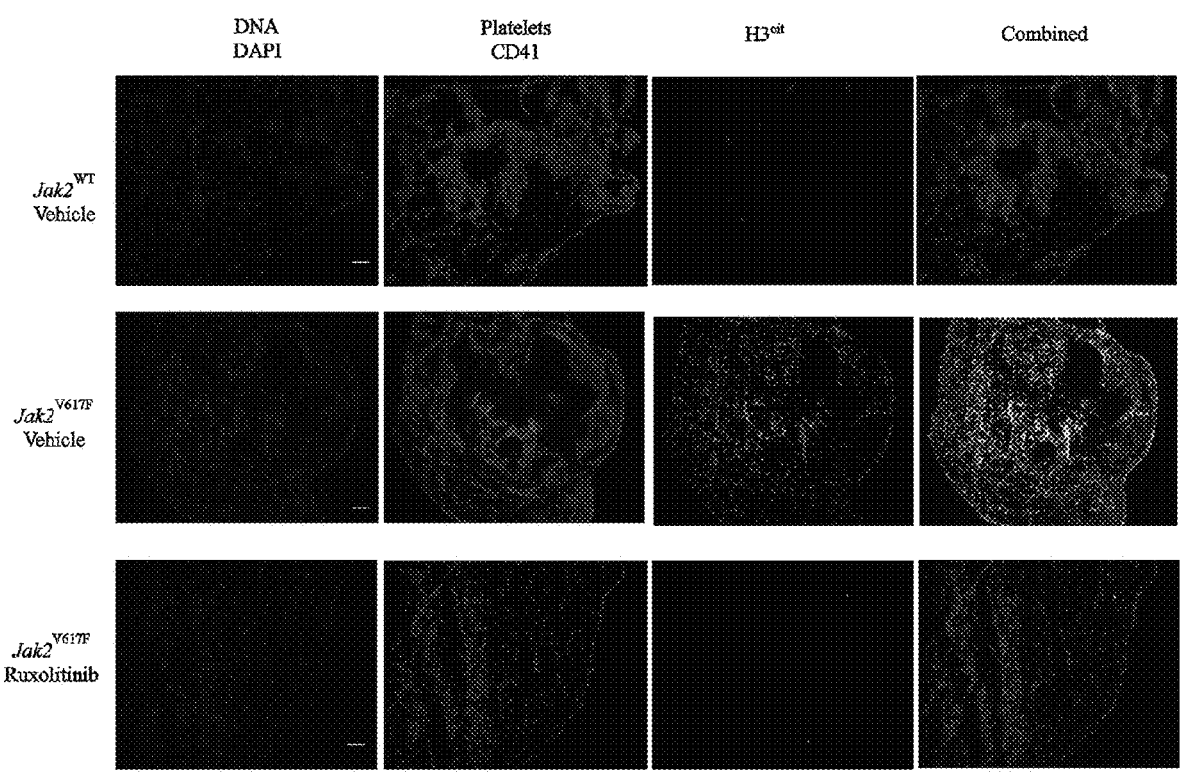
Figure 7D:
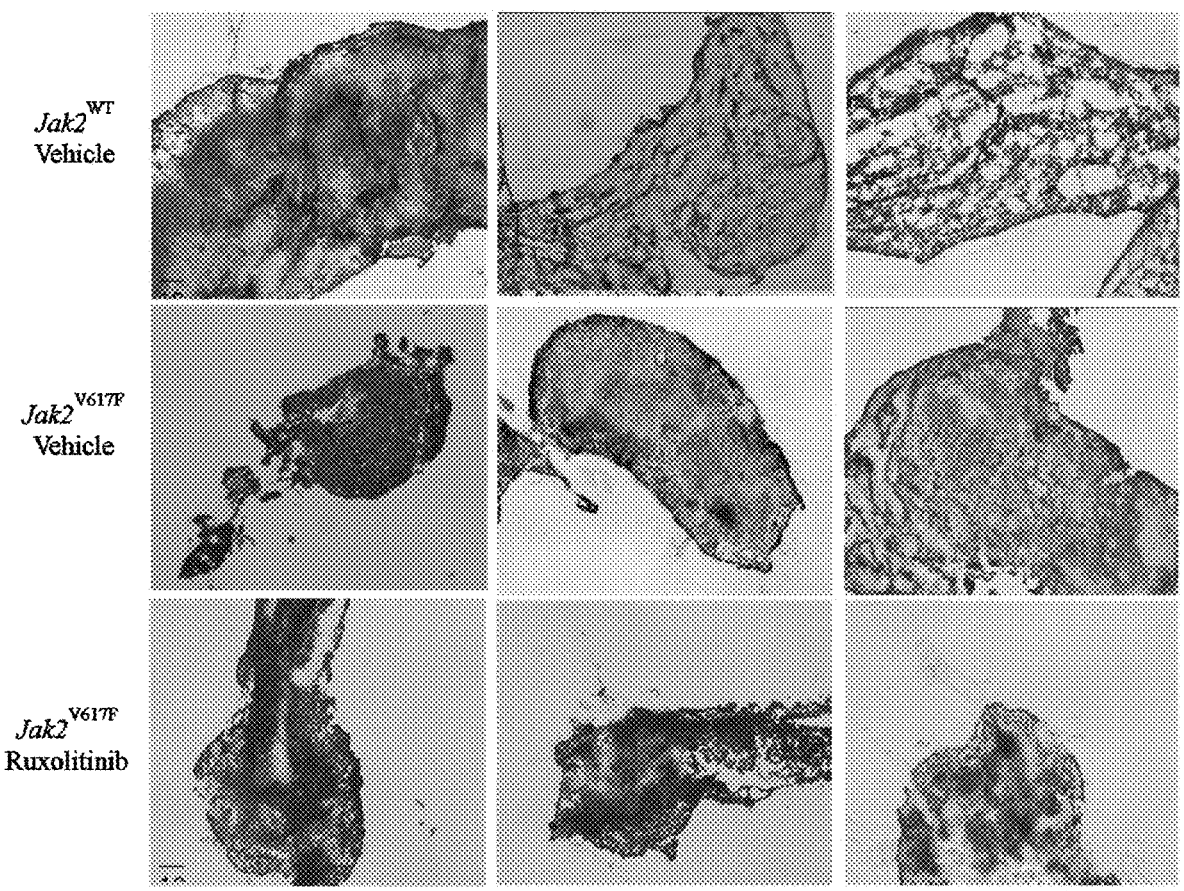

Mice engrafted with Jak2$^{V617F}$-expressing hematopoietic cells had a marked predisposition to thrombosis. At 2 hours after partial ligation of the inferior vena cava (IVC), 45% of Jak2$^{V617F}$ vehicle-treated mice developed thrombosis while none of the Jak2$^{WT}$ mice had evidence of thrombosis (p=0.04; FIGS. 2A and 2B). Plasma concentrations of dsDNA, a marker of NET activity, were increased in Jak2$^{V617F}$ as compared to Jak2$^{WT}$ mice (FIG. 2C) At 4 hours, thrombosis rates were not significantly different in the Jak2$^{V617F}$ as compared to Jak2$^{WT}$ mice (71% vs. 60%, respectively; p=0.7). The thrombi seen in the Jak2$^{V617F}$ mice had an increase in H3$^{cit}$ and neutrophil content as compared to Jak2$^{WT}$ mice (FIGS. 2D and 2E; FIG. 7B). No qualitative differences were noted in the amount or pattern of platelet staining, fibrin or RBC content between Jak2$^{WT}$ and Jak2$^{V617F}$ mice (FIG. 7A-D).

Figure 2F:
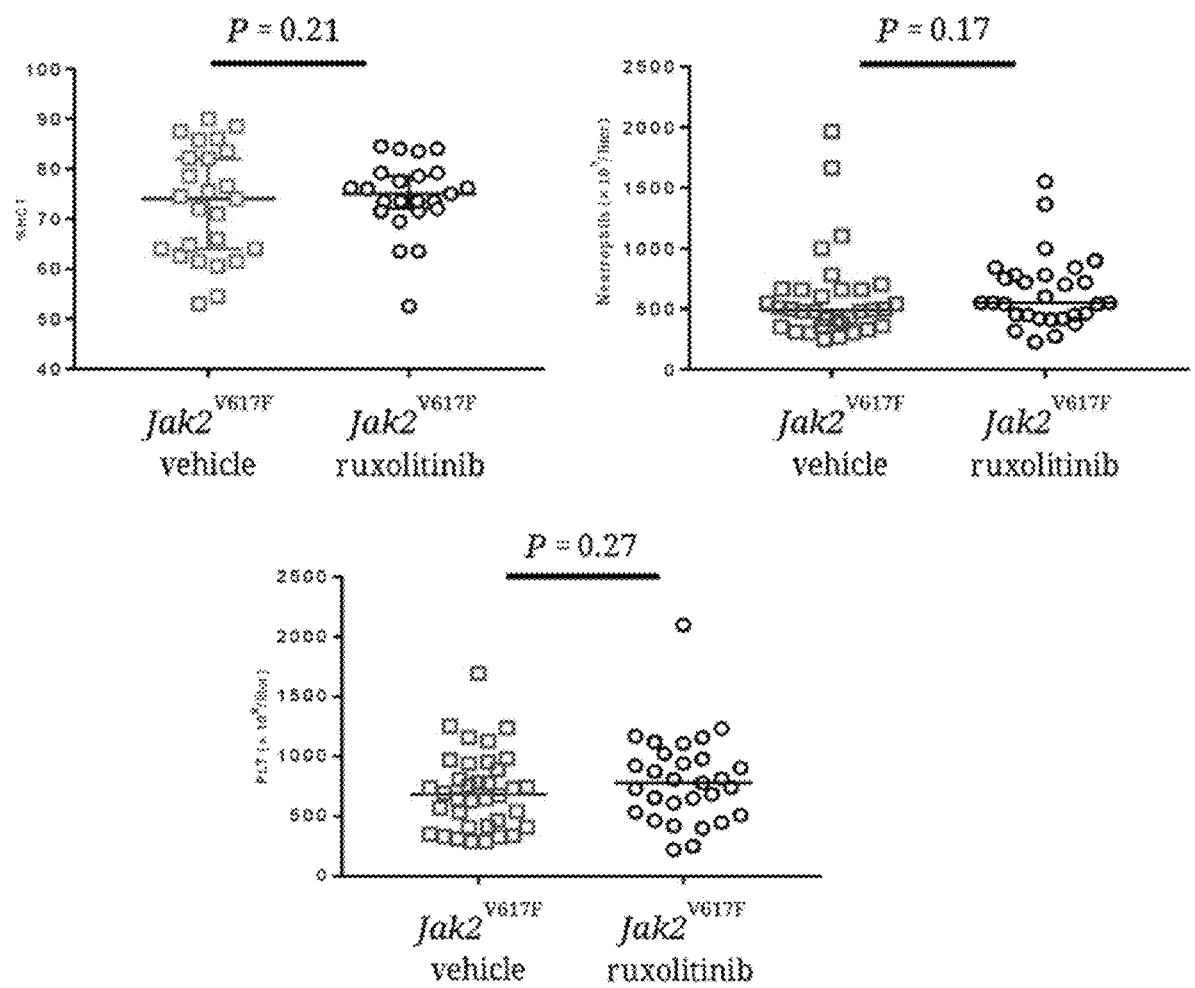

Ruxolitinib decreased the rate of thrombosis in Jak2$^{V617F}$ mice after IVC stenosis. At 2 hours post-IVC ligation, following 72 hours of ruxolitinib treatment, the ruxolitinib-treated mice had significantly lower thrombosis rates compared to vehicle-treated Jak2$^{V617F}$ mice (FIG. 2A; 0% vs. 45%, respectively; p=0.04). At 4 hours, ruxolitinib treatment significantly reduced thrombosis in Jak2$^{V617F}$ mice (FIG. 2A; 21% vs. 71%; p=0.02). Furthermore, the amount of H3$^{cit}$ as well as neutrophil content within the thrombi were significantly reduced in ruxolitinib-treated Jak2$^{V617F}$ as compared to vehicle-treated mice (FIGS. 2D and 2E, p=0.009; FIG. 7B, p=0.001, respectively). Ruxolitnib treatment did not significantly affect the HCT, platelet, or neutrophil counts, all potential contributors to a thrombotic phenotype (FIG. 2F).

To further investigate the contribution of NETs to the thrombotic tendency in the partial ligation model, we assessed clot formation rate after treatment with vehicle or deoxyribonuclease (DNase; Pulmozyme®, Genentech). DNase has been previously shown to disrupt NET structures and protects mice from thrombus formation in NET-dependent models (20, 21). Mice treated with DNase had lower thrombus formation rates for both Jak2$^{WT}$ (5/8 clots and 1/7 clots in the vehicle and DNase treated mice, respectively; p=0.06, non-significant) and Jak2$^{V617F}$ (5/7 clots and 0/8 clots in the vehicle and DNase treated mice, respectively; p=0.007) (FIG. 8A).

We repeated our thrombosis experiments in a full ligation (stasis') model that was previously shown to be associated with NET-independent thrombi formation (22, 23). At 4 hours, no difference in clotting rate was noted between vehicle and ruxolitinib treated Jak2$^{WT}$ mice (4/6 and 5/6 clots for vehicle and ruxolitinib treated, respectively; p=0.33). Furthermore, no differences in the patterns of platelet and citrullinated H3 staining were noted on immunofluorescence studies or in the measurements of plasma dsDNA (p=0.48) (FIG. 10A-C). No clots were observed in any of the Jak2$^{V617F}$ mice treated with vehicle or ruxolitinib (0/4 and 0/5 respectively).

To further evaluate aspects of neutrophil activation, we assessed the formation of reactive oxygen species (using dihydrorhodamine (DHR)) and CD11 b expression in Jak2$^{WT}$ and Jak2$^{V617F}$ mice. No differences were observed between Jak2$^{WT}$ and Jak2$^{V617F}$ mice at baseline or after IO treatment and there was no evidence of decreased baseline concentrations or post-stimulation concentrations in neutrophils from mice treated for 72 hours with ruxolitinib (FIG. 11A-B).

To assess a potential impact of genotype or treatment on platelet function in our model we performed platelet aggregometry. Platelets from Jak2$^{V617F}$ were hyporeactive as compared to Jak2$^{WT}$ mice with reduced maximal aggregation responses for activation after stimulation with adenine di-phosphate (ADP), collagen, or thrombin. To assess whether this reflected Jak2$^{V617F}$ platelets that were already maximally activated, we performed assays of activation at baseline and after thrombin stimulation, as assessed by measurement of surface expression of P-selectin and αIIb/βIII. There was no evidence that platelets from Jak2$^{V617F}$ had increased baseline activation, and reduced activation after stimulation was again demonstrated (FIG. 12). These findings are in line with previous reports of hyporeactive platelets in Jak2$^{v617F}$ mice (24).

PAD4 is Over Expressed in MPNs and is Essential for the NET-Driven Prothrombotic Phenotype in Jak2$^{v617F}$-Driven MPN Mouse Models.

Chromatin decondensation is an essential step for NET formation. One mechanism by which this occurs is the activation and nuclear localization of peptidyl-arginine deiminase (PAD4), resulting in the citrullination of histones. Inhibition of this pathway abrogates NET formation in murine models (25, 26). To determine the role of PAD4 in Jak2$^{V617F}$-driven NET formation and thrombosis, we used an established Jak2$^{V617F}$ retroviral bone marrow transplant model (27). We transduced c-Kit positive bone marrow cells from Pad4 null (Pad4$^{-/-}$) mice (26) with Jak2$^{V617F}$ retrovirus and transplanted the cells into lethally irradiated Jak2$^{WT}$ recipients. As in other models with Pad4 inactivation (19), neutrophils from mice engrafted with Jak2$^{V617F}$-expressing Pad4 null cells were unable to form NETs (FIG. 13). Lungs from mice with engrafted with Jak2$^{V617F}$-expressing Pad4$^{+/+}$ cells showed thrombus formation, whereas Jak2$^{V617F}$-expressing Pad4$^{-/-}$ mice showed no evidence of thrombosis despite evidence of gross vessel engorgement in the context of an increased HCT (FIG. 3A, FIG. 13). In addition there was no evidence of H3$^{cit}$ tin the lungs of Jak2$^{V617F}$-expressing Pad4$^{-/-}$ mice (FIG. 3B). These findings demonstrate that Jak2$^{V617F}$-driven NET formation and thrombosis is dependent on PAD4. These findings also provide further evidence of a role for neutrophils in causing thrombosis in Jak2$^{V617F}$-driven MPN and are consistent with a previously reported finding that isolated polycythemia in mice (induced with exogenous erythropoietin administration) is insufficient for thrombus formation (24).

Because high expression of PAD4 expression has previously been linked to an increased propensity for NET formation (28, 29), we examined PAD4 expression in MPN patients. Analysis of published gene expression profiling data from neutrophils derived from MPN patients and healthy controls revealed that neutrophils from patients with homozygous JAK2$^{V617F}$ MPN had 2.4 fold higher PAD4 RNA expression (30). We also found that PAD4 protein expression is increased in neutrophils from patients with JAK2$^{V617F}$ PV as compared to healthy controls (FIG. 3C).

JAK2$^{V617F}$ Positive Clonal Hematopoiesis is Associated with Increased Thrombosis Rates.

Recent studies have demonstrated that clonal somatic mutations, including JAK2$^{V617F}$, can be present in the blood of otherwise healthy individuals, a state that has been termed clonal hematopoiesis of indeterminate potential (CHIP) (31, 32). We hypothesized that individuals with JAK2$^{V617F}$-positive CHIP, without MPN or other hematologic malignancy, may also have an increased propensity for venous thrombosis due to the presence of a population of clonal neutrophils that is primed to produce NETs.

To test this hypothesis, we examined the association between JAK2$^{V617F}$ positive CHIP and venous thrombosis in a previously described large case-control cohort that included healthy controls and patients with schizophrenia who had already been sequenced as part of another study (31). After excluding patients with a diagnosis of a myeloid blood disorder, including MPN, 10,893 individuals had both clinical and exome sequencing data available (FIG. 4A). Excluding those with a diagnosis of MPN, JAK2$^{V617F}$ mutant CHIP was powerfully associated with major venous thrombotic events, including deep venous thrombosis and pulmonary embolus, which occurred in 25% of such cases (n=4/16, p=0.0003 as compared to non-CHIP) a rate much higher than in Individuals with CHIP bearing other somatic mutations (n=11/250, p=0.02; FIG. 4B, FIG. 14). This association was not significant in the schizophrenic group considered in isolation (n=4946), potentially because of an increased baseline incidence of thrombosis in the schizophrenia vs control cohort without CHIP (2.5% v 1.8%. p=0.02) that masks an effect (Table 1; FIG. 14).

TABLE 1

| Analysis groups *# | Control P value $ | Schizophrenia P value $ | All P value $ |
|---|---|---|---|
| Non-CHIP vs. CHIP | 0.0006 (0.003) | 0.11 | 0.0004 (0.002) |
| Non-CHIP vs. Non-JAK2$^{V617F}$ CHIP | 0.008 (0.04) | 0.57 | 0.025 (0.125) |

TABLE 1-continued

| Analysis groups *# | Control P value $ | Schizophrenia P value $ | All P value $ |
|---|---|---|---|
| Non-CHIP vs. JAK2$^{V617F}$ CHIP | 0.0009 (0.0045) | 0.12 | 0.0003 (0.0015) |

*Individuals with one or more mutations of unknown significance were excluded from further analysis.
Rates of thrombosis compared between groups by Fishers' exact test
$ Nominal P values are given first. Adjusted P values following Bonferroni correction are given in parentheses.

Thrombotic events occurred even in individuals with JAK2$^{V617F}$ positive CHIP and a lower variant allele frequency (VAF) (range 7-26%) (FIG. 4C). In 3 patients, DNA sampling post-dated the initial documented thrombotic event, suggesting that thrombosis cannot be attributed to a subsequent large clonal expansion. It is noteworthy that patients with CHIP were older at the time of DNA sampling than those without CHIP (median 65 v 55 p<0.0001) however this age difference was seen in both those with thrombosis (65.5 v 58.5, p=0.0002) and those without (65 v 55, p<0.0001) (FIG. 15). These data suggest that JAK2$^{V617F}$ mutations, even at a low VAF and in the absence of demonstrable MPN or other hematologic malignancy, are associated with increased risk of major venous thrombotic events. These cases might provide a basis for some cases of spontaneous thrombosis in the general population.

REFERENCES

1. T. Klampfl, H. Gisslinger, A. S. Harutyunyan, H. Nivarthi, E. Rumi, J. D. Milosevic, N. C. Them, T. Berg, B. Gisslinger, D. Pietra, D. Chen, G. I. Vladimer, K. Bagienski, C. Milanesi, I. C. Casetti, E. Sant' Antonio, V. Ferretti, C. Elena, F. Schischlik, C. Cleary, M. Six, M. Schalling, A. Schonegger, C. Bock, L. Malcovati, C. Pascutto, G. Superti-Furga, M. Cazzola, R. Kralovics, Somatic mutations of calreticulin in myeloproliferative neoplasms. N Engl J Med 369, 2379-2390 (2013).
2. T. Barbui, G. Finazzi, A. Falanga, Myeloproliferative neoplasms and thrombosis. Blood 122, 2176-2184 (2013).
3. A. M. Vannucchi, P. Guglielmelli, JAK2 mutation-related disease and thrombosis. Semin Thromb Hemost 39, 496-506 (2013).
4. T. Barbui, A. Masciulli, M. R. Marfisi, G. Tognoni, G. Finazzi, A. Rambaldi, A. Vannucchi, White blood cell counts and thrombosis in polycythemia vera: a subanalysis of the CYTO-PV study. Blood 126, 560-561 (2015).
5. R. Landolfi, L. Di Gennaro, T. Barbui, V. De Stefano, G. Finazzi, R. Marfisi, G. Tognoni, R. Marchioli, Leukocytosis as a major thrombotic risk factor in patients with polycythemia vera. Blood 109, 2446-2452 (2007).
6. P. J. Campbell, C. MacLean, P. A. Beer, G. Buck, K. Wheatley, J. J. Kiladjian, C. Forsyth, C. N. Harrison, A. R. Green, Correlation of blood counts with vascular complications in essential thrombocythemia: analysis of the prospective PT1 cohort. Blood 120, 1409-1411 (2012).
7. A. Carobbio, E. Antonioli, P. Guglielmelli, A. M. Vannucchi, F. Delaini, V. Guerini, G. Finazzi, A. Rambaldi, T. Barbui, Leukocytosis and risk stratification assessment in essential thrombocythemia. J Clin Oncol 26, 2732-2736 (2008).
8. T. Barbui, A. Carobbio, F. Cervantes, A. M. Vannucchi, P. Guglielmelli, E. Antonioli, A. Alvarez-Larran, A. Rambaldi, G. Finazzi, G. Barosi, Thrombosis in primary myelofibrosis: incidence and risk factors. Blood 115, 778-782 (2010).
9. V. Buxhofer-Ausch, H. Gisslinger, J. Thiele, B. Gisslinger, H. M. Kvasnicka, L. Mullauer, S. Frantal, A. Carobbio, F. Passamonti, E. Rumi, M. Ruggeri, F. Rodeghiero, M. L. Randi, I. Bertozzi, A. M. Vannucchi, E. Antonioli, G. Finazzi, N. Gangat, A. Tefferi, T. Barbui, Leukocytosis as an important risk factor for arterial thrombosis in WHO-defined early/prefibrotic myelofibrosis: an international study of 264 patients. Am J Hematol 87, 669-672 (2012).
10. M. Hurtado-Nedelec, M. J. Csillag-Grange, T. Boussetta, S. A. Belambri, M. Fay, B. Cassinat, M. A. Gougerot-Pocidalo, P. M. Dang, J. El-Benna, Increased reactive oxygen species production and p47phox phosphorylation in neutrophils from myeloproliferative disorders patients with JAK2 (V617F) mutation. Haematologica 98, 1517-1524 (2013).
11. A. Falanga, M. Marchetti, Thrombosis in myeloproliferative neoplasms. Semin Thromb Hemost 40, 348-358 (2014).
12. M. Kushnir, H. W. Cohen, H. H. Billett, Persistent neutrophilia is a marker for an increased risk of venous thrombosis. J Thromb Thrombolysis 42, 545-551 (2016).
13. B. D. Vadher, S. J. Machin, K. G. Patterson, C. Sukhu, H. Walker, Life-threatening thrombotic and haemorrhagic problems associated with silent myeloproliferative disorders. Br J Haematol 85, 213-216 (1993).
14. V. Brinkmann, U. Reichard, C. Goosmann, B. Fauler, Y. Uhlemann, D. S. Weiss, Y. Weinrauch, A. Zychlinsky, Neutrophil extracellular traps kill bacteria. Science 303, 1532-1535 (2004).
15. K. Martinod, D. D. Wagner, Thrombosis: tangled up in NETs. Blood 123, 2768-2776 (2014).
16. A. Barnado, L. J. Crofford, J. C. Oates, At the Bedside: Neutrophil extracellular traps (NETs) as targets for biomarkers and therapies in autoimmune diseases. J Leukoc Biol 99, 265-278 (2016).
17. Y. Wang, M. Li, S. Stadler, S. Correll, P. Li, D. Wang, R. Hayama, L. Leonelli, H. Han, S. A. Grigoryev, C. D. Allis, S. A. Coonrod, Histone hypercitrullination mediates chromatin decondensation and neutrophil extracellular trap formation. J Cell Biol 184, 205-213 (2009).
18. A. Mullally, S. W. Lane, B. Ball, C. Megerdichian, R. Okabe, F. Al-Shahrour, M. Paktinat, J. E. Haydu, E. Housman, A. M. Lord, G. Wernig, M. G. Kharas, T. Mercher, J. L. Kutok, D. G. Gilliland, B. L. Ebert, Physiological Jak2V617F expression causes a lethal myeloproliferative neoplasm with differential effects on hematopoietic stem and progenitor cells. Cancer Cell 17, 584-596 (2010).
19. K. Martinod, M. Demers, T. A. Fuchs, S. L. Wong, A. Brill, M. Gallant, J. Hu, Y. Wang, D. D. Wagner, Neutrophil histone modification by peptidylarginine deiminase 4 is critical for deep vein thrombosis in mice. Proc Natl Acad Sci U S A 110, 8674-8679 (2013).
20. A. Brill, T. A. Fuchs, A. S. Savchenko, G. M. Thomas, K. Martinod, S. F. De Meyer, A. A. Bhandari, D. D. Wagner, Neutrophil extracellular traps promote deep vein thrombosis in mice. J Thromb Haemost 10, 136-144 (2012).
21. T. A. Fuchs, A. Brill, D. Duerschmied, D. Schatzberg, M. Monestier, D. D. Myers, Jr., S. K. Wroblski, T. W. Wakefield, J. H. Hartwig, D. D. Wagner, Extracellular DNA traps promote thrombosis. Proc Natl Acad Sci U S A 107, 15880-15885 (2010).
22. H. Meng, S. Yalavarthi, Y. Kanthi, L. F. Mazza, M. A. Elfline, C. E. Luke, D. J. Pinsky, P. K. Henke, J. S. Knight, In Vivo Role of Neutrophil Extracellular Traps in Antiphospholipid Antibody-Mediated Venous Thrombosis. Arthritis Rheumatol 69, 655-667 (2017).

23. O. M. El-Sayed, N. A. Dewyer, C. E. Luke, M. Elfline, A. Laser, C. Hogaboam, S. L. Kunkel, P. K. Henke, Intact Toll-like receptor 9 signaling in neutrophils modulates normal thrombogenesis in mice. J Vasc Surg 64, 1450-1458 e1451 (2016).

24. L. Lamrani, C. Lacout, V. Ollivier, C. V. Denis, E. Gardiner, B. Ho Tin Noe, W. Vainchenker, J. L. Villeval, M. Jandrot-Perrus, Hemostatic disorders in a JAK2V617F-driven mouse model of myeloproliferative neoplasm. Blood 124, 1136-1145 (2014).

25. H. D. Lewis, J. Liddle, J. E. Coote, S. J. Atkinson, M. D. Barker, B. D. Bax, K. L. Bicker, R. P. Bingham, M. Campbell, Y. H. Chen, C. W. Chung, P. D. Craggs, R. P. Davis, D. Eberhard, G. Joberty, K. E. Lind, K. Locke, C. Mailer, K. Martinod, C. Patten, O. Polyakova, C. E. Rise, M. Rudiger, R. J. Sheppard, D. J. Slade, P. Thomas, J. Thorpe, G. Yao, G. Drewes, D. D. Wagner, P. R. Thompson, R. K. Prinjha, D. M. Wilson, Inhibition of PAD4 activity is sufficient to disrupt mouse and human NET formation. Nat Chem Biol 11, 189-191 (2015).

26. P. Li, M. Li, M. R. Lindberg, M. J. Kennett, N. Xiong, Y. Wang, PAD4 is essential for antibacterial innate immunity mediated by neutrophil extracellular traps. J Exp Med 207, 1853-1862 (2010).

27. G. Wernig, T. Mercher, R. Okabe, R. L. Levine, B. H. Lee, D. G. Gilliland, Expression of Jak2V617F causes a polycythemia vera-like disease with associated myelofibrosis in a murine bone marrow transplant model. Blood 107, 4274-4281 (2006).

28. M. Leshner, S. Wang, C. Lewis, H. Zheng, X. A. Chen, L. Santy, Y. Wang, PAD4 mediated histone hypercitrullination induces heterochromatin decondensation and chromatin unfolding to form neutrophil extracellular trap-like structures. Front Immunol 3, 307 (2012).

29. S. L. Wong, M. Demers, K. Martinod, M. Gallant, Y. Wang, A. B. Goldfine, C. R. Kahn, D. D. Wagner, Diabetes primes neutrophils to undergo NETosis, which impairs wound healing. Nat Med 21, 815-819 (2015).

30. R. Rampal, F. Al-Shahrour, O. Abdel-Wahab, J. P. Patel, J. P. Brunel, C. H. Mermel, A. J. Bass, J. Pretz, J. Ahn, T. Hricik, O. Kilpivaara, M. Wadleigh, L. Busque, D. G. Gilliland, T. R. Golub, B. L. Ebert, R. L. Levine, Integrated genomic analysis illustrates the central role of JAK-STAT pathway activation in myeloproliferative neoplasm pathogenesis. Blood 123, e123-133 (2014).

31. G. Genovese, A. K. Kahler, R. E. Handsaker, J. Lindberg, S. A. Rose, S. F. Bakhoum, K. Chambert, E. Mick, B. M. Neale, M. Fromer, S. M. Purcell, O. Svantesson, M. Landen, M. Hoglund, S. Lehmann, S. B. Gabriel, J. L. Moran, E. S. Lander, P. F. Sullivan, P. Sklar, H. Gronberg, C. M. Hultman, S. A. McCarroll, Clonal hematopoiesis and blood-cancer risk inferred from blood DNA sequence. N Engl J Med 371, 2477-2487 (2014). 32. S. Jaiswal, P. Fontanillas, J. Flannick, A. Manning, P. V. Grauman, B. G. Mar, R. C. Lindsley, C. H. Mermel, N. Burtt, A. Chavez, J. M. Higgins, V. Moltchanov, F. C. Kuo, M. J. Kluk, B. Henderson, L. Kinnunen, H. A. Koistinen, C. Ladenvall, G. Getz, A. Correa, B. F. Banahan, S. Gabriel, S. Kathiresan, H. M. Stringham, M. I. McCarthy, M. Boehnke, J. Tuomilehto, C. Haiman, L. Groop, G. Atzmon, J. G. Wilson, D. Neuberg, D. Altshuler, B. L. Ebert, Age-related clonal hematopoiesis associated with adverse outcomes. N Engl J Med 371, 2488-2498 (2014).

33. C. P. Marin Oyarzun, A. Carestia, P. R. Lev, A. C. Glembotsky, M. A. Castro Rios, B. Moiraghi, F. C. Molinas, R. F. Marta, M. Schaffner, P. G. Heller, Neutrophil extracellular trap formation and circulating nucleosomes in patients with chronic myeloproliferative neoplasms. Sci Rep 6, 38738 (2016).

34. A. M. Vannucchi, J. J. Kiladjian, M. Griesshammer, T. Masszi, S. Durrant, F. Passamonti, C. N. Harrison, F. Pane, P. Zachee, R. Mesa, S. He, M. M. Jones, W. Garrett, J. Li, U. Pirron, D. Habr, S. Verstovsek, Ruxolitinib versus standard therapy for the treatment of polycythemia vera. N Engl J Med 372, 426-435 (2015).

35. S. Verstovsek, R. A. Mesa, J. Gotlib, R. S. Levy, V. Gupta, J. F. DiPersio, J. V. Catalano, M. Deininger, C. Miller, R. T. Silver, M. Talpaz, E. F. Winton, J. H. Harvey, Jr., M. O. Arcasoy, E. Hexner, R. M. Lyons, R. Paquette, A. Raza, K. Vaddi, S. Erickson-Viitanen, I. L. Koumenis, W. Sun, V. Sandor, H. M. Kantarjian, A double-blind, placebo-controlled trial of ruxolitinib for myelofibrosis. N Engl J Med 366, 799-807 (2012).

36. K. Martinod, T. Witsch, K. Farley, M. Gallant, E. Remold-O'Donnell, D. D. Wagner, Neutrophil elastase-deficient mice form neutrophil extracellular traps in an experimental model of deep vein thrombosis. J Thromb Haemost 14, 551-558 (2016).

37. M. Demers, D. S. Krause, D. Schatzberg, K. Martinod, J. R. Voorhees, T. A. Fuchs, D. T. Scadden, D. D. Wagner, Cancers predispose neutrophils to release extracellular DNA traps that contribute to cancer-associated thrombosis. Proc Natl Acad Sci U S A 109, 13076-13081 (2012).

38. D. Simon, H. U. Simon, S. Yousefi, Extracellular DNA traps in allergic, infectious, and autoimmune diseases. Allergy 68, 409-416 (2013).

39. A. S. Gonzalez, B. W. Bardoel, C. J. Harbort, A. Zychlinsky, Induction and quantification of neutrophil extracellular traps. Methods Mol Biol 1124, 307-318 (2014).

40. A. Quintas-Cardama, K. Vaddi, P. Liu, T. Manshouri, J. Li, P. A. Scherle, E. Caulder, X. Wen, Y. Li, P. Waeltz, M. Rupar, T. Burn, Y. Lo, J. Kelley, M. Covington, S. Shepard, J. D. Rodgers, P. Haley, H. Kantarjian, J. S. Fridman, S. Verstovsek, Preclinical characterization of the selective JAK1/2 inhibitor INCB018424: therapeutic implications for the treatment of myeloproliferative neoplasms. Blood 115, 3109-3117 (2010).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing risk of recurrence of a cardiovascular event in a subject who has had at least one cardiovascular event, the method comprising:
identifying the subject who has had at least one cardiovascular event;
determining the JAK2 genotype of the subject;
selecting the subject who has a Jak2$^{V617F}$ genotype comprising the Jak2$^{V617F}$ single nucleotide polymorphism in one or both alleles of the JAK2 (rs77375493) gene; and administering to the subject an effective amount of an inhibitor of JAK-STAT signaling, wherein the inhibitor of JAK-STAT signaling is selected from the group consisting of Tofacitinib (CP690,550); Baricitinib (INCB028050); Ruxolitinib (INCB018424); TG101348 (SAR302503); Lestaurtinib (CEP-701); AZD1480; R348; VX-509; GLPG0634; GSK2586184; AC-430; Pacritinib (SB1518); NS-018; CHZ868; INCB039110; Filgotinib (G-146034, GLPG-0634); Cerdulatinib (PRT062070); Gandotinib (LY-2784544); Momelotinib (GS-0387, CYT-387); PF-04965842); Upadacitinib (ABT-494); Peficitinib (ASP015K, JNJ-54781532); Fedratinib (SAR302503); and BMS-911543, and wherein the subject has Clonal Hematopoiesis of Indeterminate Potential (CHIP).

2. The method of claim 1, wherein the cardiovascular event is thrombosis or myocardial infarction (MI).

3. The method of claim 1, wherein determining the JAK2 genotype of the subject comprises determining a sequence of a portion of the subject's genome comprising a sequence encoding amino acid 617 of JAK2, and determining whether the sequence encodes a valine or a phenylalanine.

4. The method of claim 3, wherein determining a sequence of a portion of the subject's genome comprises amplifying and/or sequencing a portion of the subject's genome comprising SEQ ID NO:1, and determining the identity of the nucleotide at position 26 of SEQ ID NO:1, and/or using a probe that hybridizes to the nucleotide at position 26 of SEQ ID NO:1.

5. The method of claim 1, wherein the inhibitor of JAK-STAT signaling is Ruxolitinib (INCB018424).

6. A method of reducing risk of occurrence or recurrence of a cardiovascular event in a subject, the method comprising determining the JAK2 genotype of the subject; selecting the subject who has a Jak2$^{V617F}$ genotype comprising the Jak2$^{V617F}$ single nucleotide polymorphism in one or both alleles of the JAK2 (rs77375493) gene; and administering to the subject an effective amount of an inhibitor of JAK-STAT signaling; wherein the inhibitor of JAK-STAT signaling is selected from the group consisting of Tofacitinib (CP690, 550); Baricitinib (INCB028050); Ruxolitinib (INCB018424); TG101348 (SAR302503); Lestaurtinib (CEP-701); AZD1480; R348; VX-509; GLPG0634; GSK2586184; AC-430; Pacritinib (SB1518); NS-018; CHZ868; INCB039110; Filgotinib (G-146034, GLPG-0634); Cerdulatinib (PRT062070); Gandotinib (LY-2784544); Momelotinib (GS-0387, CYT-387); PF-04965842); Upadacitinib (ABT-494); Peficitinib (ASP015K, JNJ-54781532); Fedratinib (SAR302503); and BMS-911543; and wherein the subject has Clonal Hematopoiesis of Indeterminate Potential (CHIP).

7. The method of claim 6, wherein the cardiovascular event is thrombosis or myocardial infarction (MI).

8. The method of claim 6, wherein determining the JAK2 genotype of the subject comprises determining a sequence of a portion of the subject's genome comprising a sequence encoding amino acid 617 of JAK2, and determining whether the sequence encodes a valine or a phenylalanine.

9. The method of claim 8, wherein determining a sequence of a portion of the subject's genome comprises amplifying and/or sequencing a portion of the subject's genome comprising SEQ ID NO:1, and determining the identity of the nucleotide at position 26 of SEQ ID NO:1, and/or using a probe that hybridizes to the nucleotide at position 26 of SEQ ID NO:1.

10. The method of claim 6, wherein the inhibitor of JAK-STAT signaling is Ruxolitinib (INCB018424).

* * * * *

UNITED STATES PATENT AND TRADEMARK OFFICE
CERTIFICATE OF CORRECTION

| | | |
|---|---|---|
| PATENT NO. | : 11,426,405 B2 | Page 1 of 1 |
| APPLICATION NO. | : 16/209698 | |
| DATED | : August 30, 2022 | |
| INVENTOR(S) | : Rob Sellar et al. | |

It is certified that error appears in the above-identified patent and that said Letters Patent is hereby corrected as shown below:

In the Specification

In Column 1, Line 16 (approx.), delete "No. HL082945" and insert -- Nos. HL082945 and HL135765 --

Signed and Sealed this
Sixth Day of January, 2026

John A. Squires
*Director of the United States Patent and Trademark Office*

SEQUENCE LISTING

<160> NUMBER OF SEQ ID NOS: 1

<210> SEQ ID NO 1
<211> LENGTH: 51
<212> TYPE: DNA
<213> ORGANISM: Artificial Sequence
<220> FEATURE:
<223> OTHER INFORMATION: primer of JAK2V617F

```
<220> FEATURE:
<221> NAME/KEY: misc_feature
<222> LOCATION: (26)..(26)
<223> OTHER INFORMATION: n=A, G or T

<400> SEQUENCE: 1
tttggtttta aattatggag tatgtntctg tggagacgag agtaagtaaa a          51
```